(12) United States Patent
Norderhaug et al.

(10) Patent No.: US 9,011,772 B2
(45) Date of Patent: Apr. 21, 2015

(54) APPARATUS FOR AND METHOD OF AUTOMATED PROCESSING OF BIOLOGICAL SAMPLES

(75) Inventors: Lars Norderhaug, Nesodtangen (NO); Morten Egeberg, Blaker (NO); Tommy Rivrud, Bekkesstua (NO); Lars Nokleby, Stabekk (NO); Espir Kahatt, Carlsbad, CA (US); Jamie Hogan, San Diego, CA (US); Kornelija Zgonc, Carlsbad, CA (US); Norman Trolson, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 135 days.

(21) Appl. No.: 13/147,084

(22) PCT Filed: May 11, 2010

(86) PCT No.: PCT/EP2010/056510
§ 371 (c)(1),
(2), (4) Date: Jan. 6, 2012

(87) PCT Pub. No.: WO2010/130762
PCT Pub. Date: Nov. 18, 2010

(65) Prior Publication Data
US 2011/0287447 A1   Nov. 24, 2011

Related U.S. Application Data

(60) Provisional application No. 61/309,371, filed on Mar. 1, 2010, provisional application No. 61/177,628, filed on May 12, 2009.

(30) Foreign Application Priority Data

Sep. 28, 2009   (GB) .................................. 0916965.7

(51) Int. Cl.
*G01N 30/04*   (2006.01)
*G01N 27/00*   (2006.01)
(Continued)

(52) U.S. Cl.
CPC ...... *B01L 3/0275* (2013.01); *G01N 2035/00227* (2013.01); *B01L 2300/0819* (2013.01);
(Continued)

(58) Field of Classification Search
CPC ................ G01N 35/0098; G01N 2035/00227; G01N 2035/0436; G01N 2035/1039; B01L 2300/0819
See application file for complete search history.

(56) References Cited

U.S. PATENT DOCUMENTS 4,118,280 A   10/1978   Charles
5,779,868 A    7/1998   Parce et al.
(Continued)

FOREIGN PATENT DOCUMENTS

CN   201094106   7/2008
EP     0763739   3/1997
(Continued)

OTHER PUBLICATIONS

GB 0916965.7, Amendment Search Report mailed Jan. 26, 2010.
(Continued)

*Primary Examiner* — P. Kathryn Wright
(74) *Attorney, Agent, or Firm* — Life Technologies Corporation

(57) ABSTRACT

Provided herein is a bioprocessing device, bioprocessing card, and fluidics cartridge for performing automated bioprocessing of a sample. The bioprocessing card may include a plurality of pipette tips; and at least one pump in fluid communication with the plurality of pipette tips. In some embodiments, the pumps and the pipette tips are in fluid communication through a processing channel which may be a microscale channel. Also provided herein is an automated bioprocessing device comprising: at least one bioprocessing card; at least one fluidic cartridge; and an automated control system configured to control automated bioprocessing of a sample. Further provided herein are methods of use of the device, card, and cartridge.

19 Claims, 33 Drawing Sheets

(51) Int. Cl.
*G01N 1/10* (2006.01)
*B01L 3/02* (2006.01)
*G01N 35/00* (2006.01)
*B01L 3/00* (2006.01)
*B01L 9/00* (2006.01)
*G01N 35/04* (2006.01)
*G01N 35/10* (2006.01)

(52) U.S. Cl.
CPC ........... *B01L3/0293* (2013.01); *B01L 3/50273* (2013.01); *B01L 3/563* (2013.01); *B01L 9/543* (2013.01); *B01L 2400/0481* (2013.01); *B01L 2400/0487* (2013.01); *B01L 2400/0655* (2013.01); *G01N 2035/00237* (2013.01); *G01N 2035/0436* (2013.01); *G01N 2035/0498* (2013.01); *G01N 2035/103* (2013.01); *G01N 2035/1039* (2013.01); *G01N 35/0098* (2013.01)

(56) References Cited

U.S. PATENT DOCUMENTS

| | | | |
|---|---|---|---|
| 5,990,301 | A | 11/1999 | Colpan et al. |
| 6,066,243 | A | 5/2000 | Anderson et al. |
| 6,242,220 | B1 | 6/2001 | Wahle et al. |
| 6,297,371 | B1 | 10/2001 | Colpan et al. |
| 6,767,733 | B1 | 7/2004 | Green |
| 6,914,137 | B2 | 7/2005 | Baker |
| 7,105,225 | B2 | 9/2006 | Birkholz et al. |
| 7,109,322 | B2 | 9/2006 | Colpan et al. |
| 7,214,508 | B2 | 5/2007 | Hucklenbroich et al. |
| 7,479,256 | B1 | 1/2009 | Gruhler et al. |
| 7,723,099 | B2 | 5/2010 | Miller et al. |
| 2001/0051377 | A1 | 12/2001 | Hammer et al. |
| 2002/0039783 | A1 | 4/2002 | McMillan et al. |
| 2002/0051737 | A1 | 5/2002 | Sollböhmer et al. |
| 2003/0224523 | A1 | 12/2003 | Thornberg et al. |
| 2003/0230488 | A1 | 12/2003 | Lee et al. |
| 2004/0166504 | A1 | 8/2004 | Rossier et al. |
| 2004/0203055 | A1 | 10/2004 | Kennedy et al. |
| 2004/0208794 | A1 | 10/2004 | Karg et al. |
| 2005/0016852 | A1 | 1/2005 | Amirkhanian et al. |
| 2005/0047963 | A1 * | 3/2005 | Safar et al. .................. 422/63 |
| 2006/0154247 | A1 | 7/2006 | Baker et al. |
| 2006/0257993 | A1 | 11/2006 | McDevitt et al. |
| 2007/0048188 | A1 | 3/2007 | Bigus |
| 2007/0092410 | A1 | 4/2007 | Ricker et al. |
| 2007/0117972 | A1 | 5/2007 | Halaka |
| 2007/0263046 | A1 | 11/2007 | Iwasa et al. |
| 2008/0083263 | A1 | 4/2008 | Philipp et al. |
| 2008/0182301 | A1 | 7/2008 | Handique et al. |
| 2008/0200343 | A1 | 8/2008 | Clemens et al. |
| 2008/0217246 | A1 | 9/2008 | Benn et al. |
| 2009/0155123 | A1 | 6/2009 | Williams et al. |
| 2010/0120129 | A1 | 5/2010 | Amshey et al. |

FOREIGN PATENT DOCUMENTS

| | | |
|---|---|---|
| EP | 0802413 | 10/1997 |
| EP | 0865824 | 9/1998 |
| EP | 0965842 | 12/1999 |
| EP | 1385006 | 1/2004 |
| JP | 2002065242 | 3/2002 |
| JP | 2006003145 | 1/2006 |
| JP | 2006149215 | 6/2006 |
| JP | 2006308428 | 11/2006 |
| JP | 2007187674 | 7/2007 |
| KR | 100710122 | 4/2007 |
| KR | 2020080000828 | 5/2008 |
| WO | WO93/20440 | 10/1993 |
| WO | WO94/18565 | 8/1994 |
| WO | WO96/12958 | 5/1996 |
| WO | WO00/76663 | 12/2000 |
| WO | WO2004/032044 | 4/2004 |
| WO | WO2004/092721 | 10/2004 |
| WO | WO2006/065598 | 6/2006 |
| WO | WO2006/099255 | 9/2006 |
| WO | WO2008/030631 | 3/2008 |
| WO | WO2009/108260 | 9/2009 |
| WO | WO2010/025302 | 3/2010 |
| WO | WO2010/130762 | 11/2010 |

OTHER PUBLICATIONS

GB 0916965.7, Search Report mailed May 6, 2010.
PCT/EP2010/056510, International Search Report mailed Mar. 24, 2011.
PCT/EP2010/056510, Written Opinion mailed Dec. 22, 2010.
Invitrogen, "BenchPro (TM) 4100 Western Processing System Product Literature", Invitrogen Website: http://www.invitrogen.com/site/us/en/home/Products-and-Services/Applications/Protein-Expression-and-Analysis/Western-Blotting/BenchPro4100.html, Oct. 23, 2008, 2 pages.

* cited by examiner

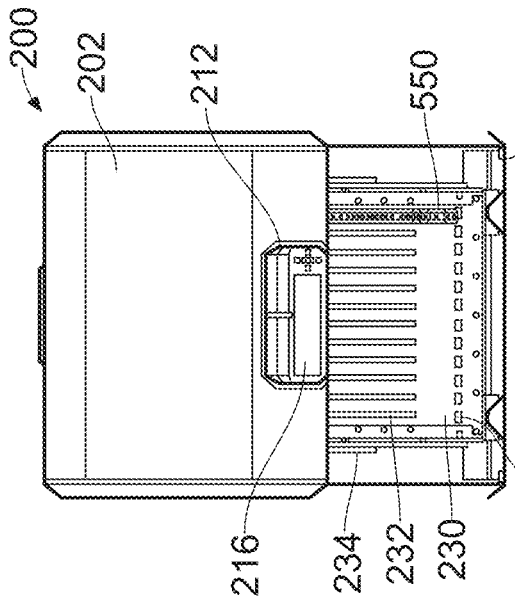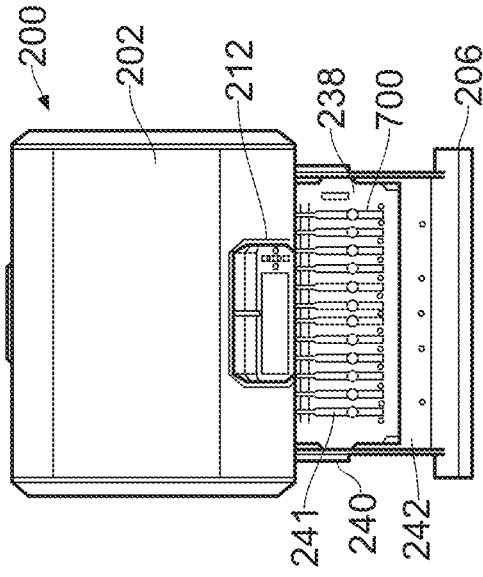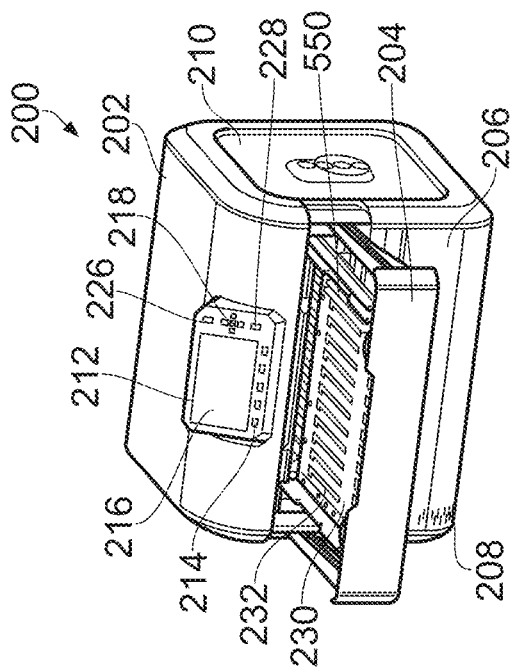

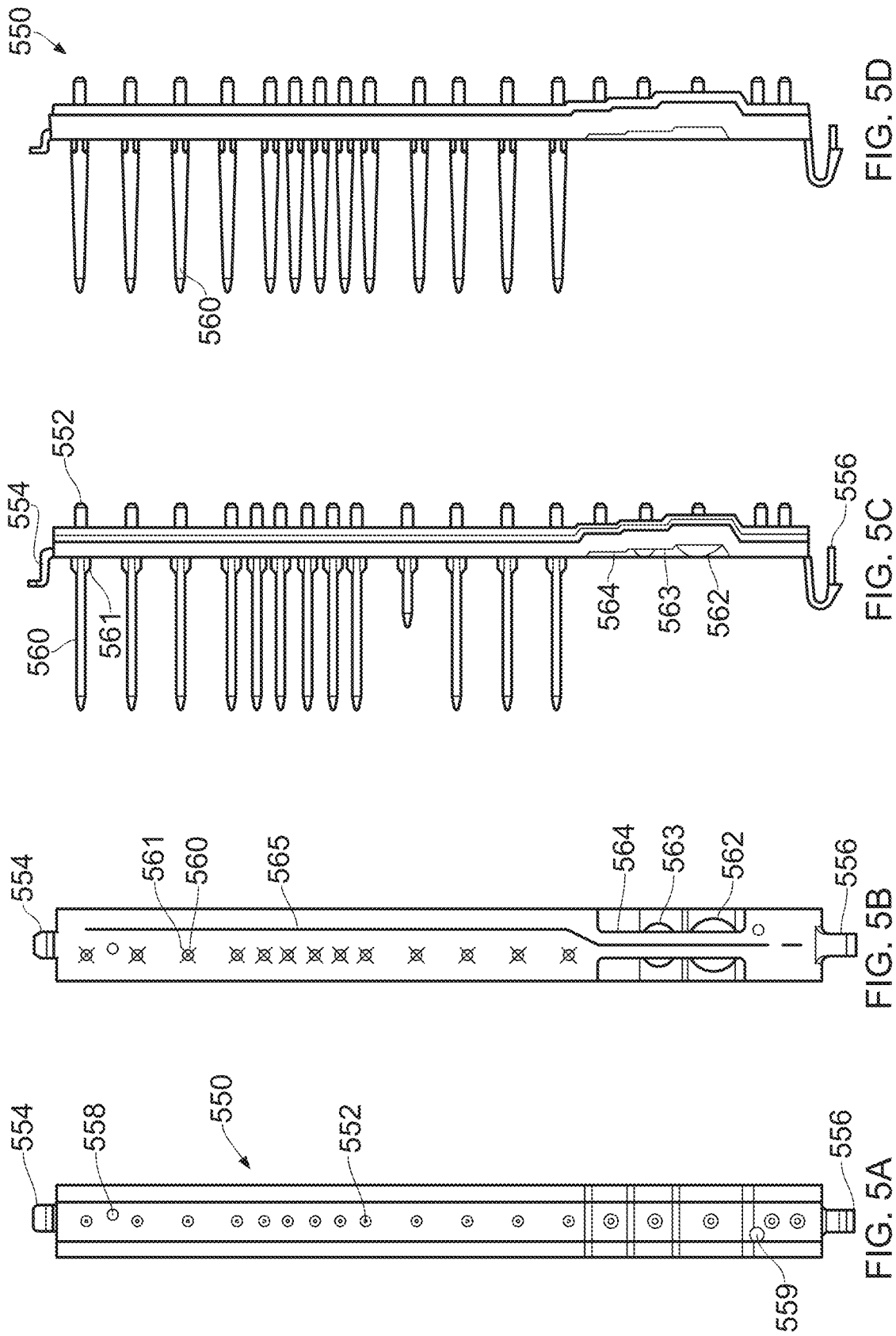

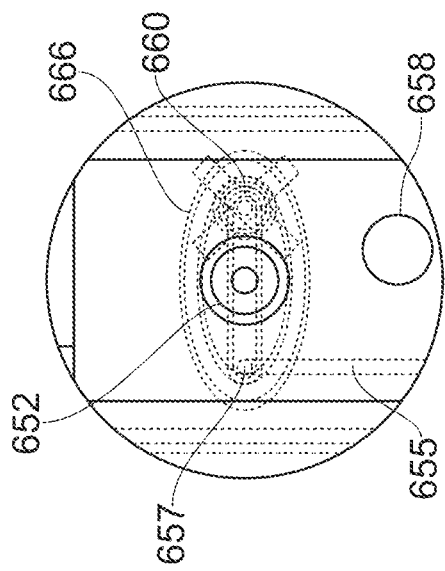
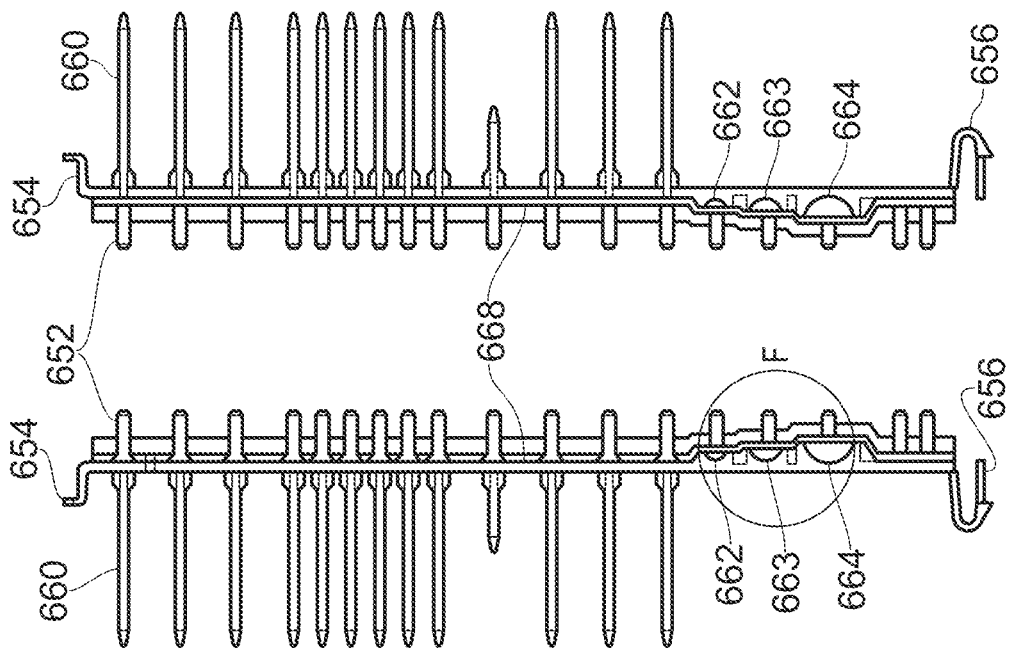
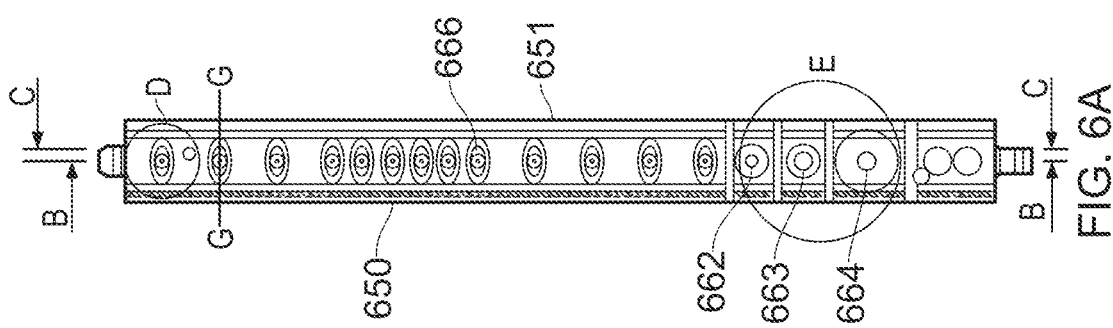

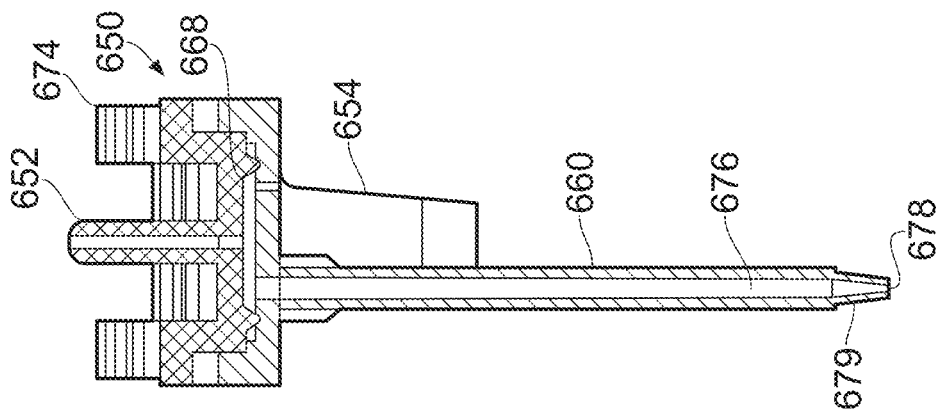
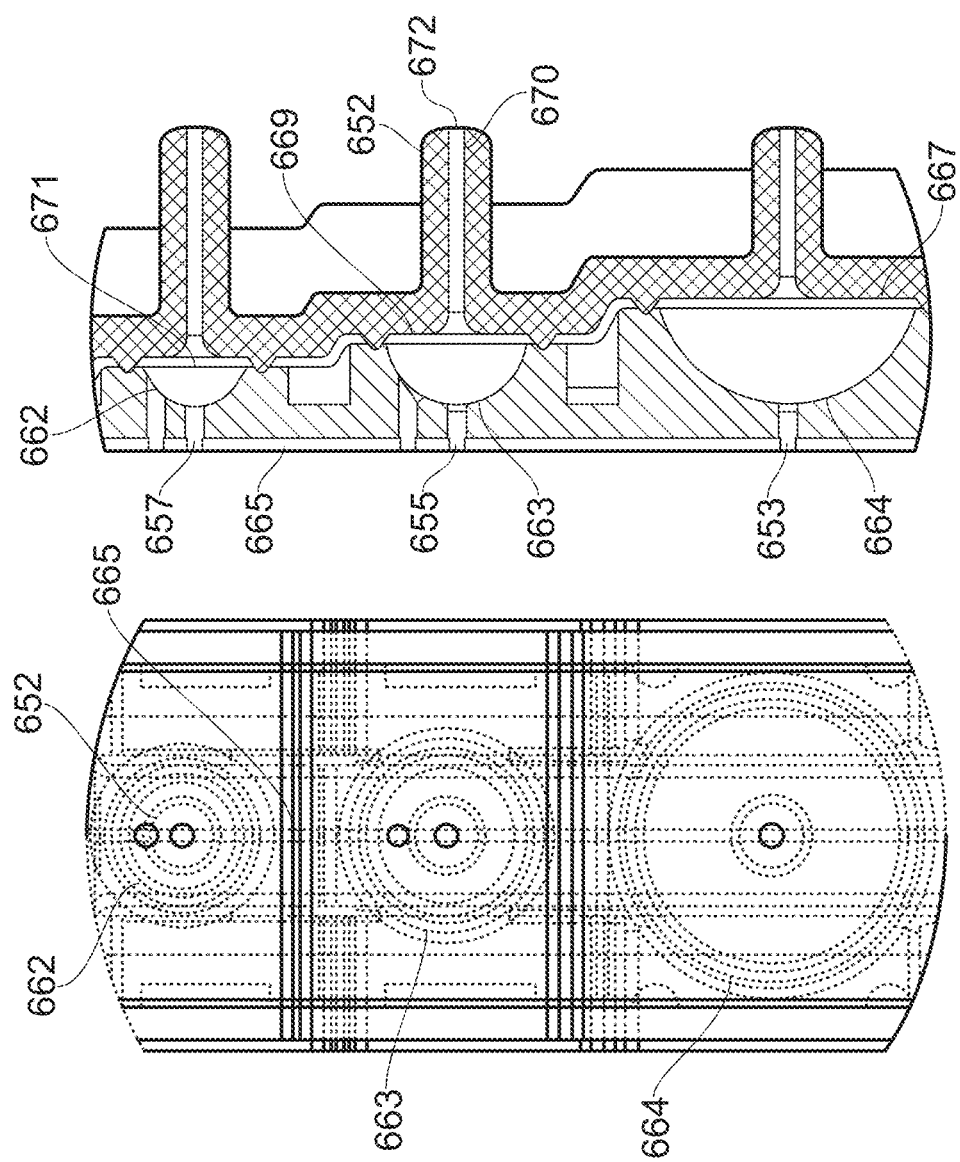
FIG. 6G
FIG. 6F
FIG. 6E

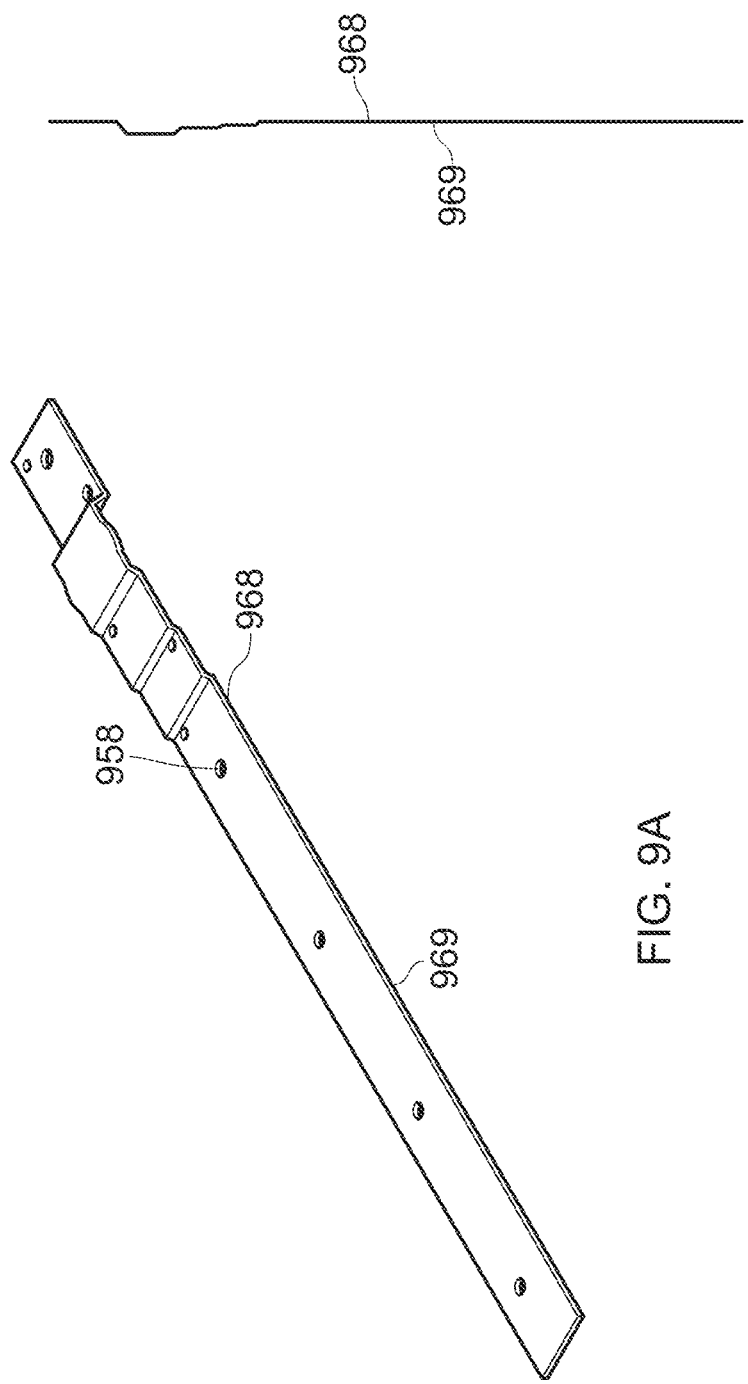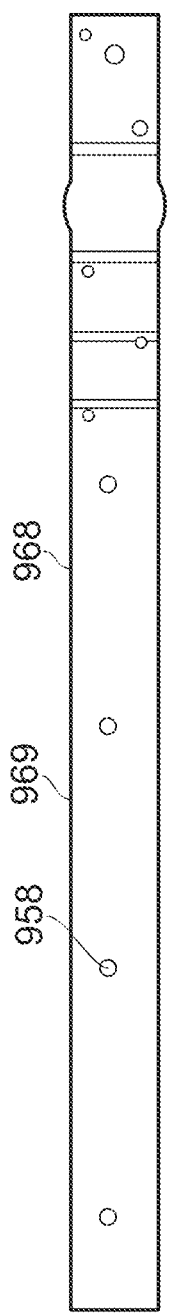
FIG. 9A
FIG. 9B
FIG. 9C

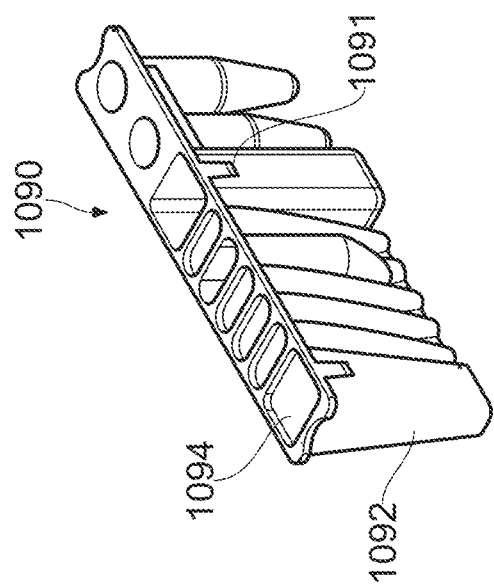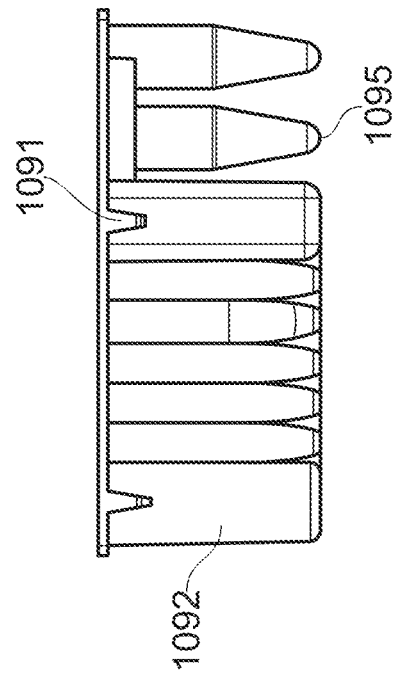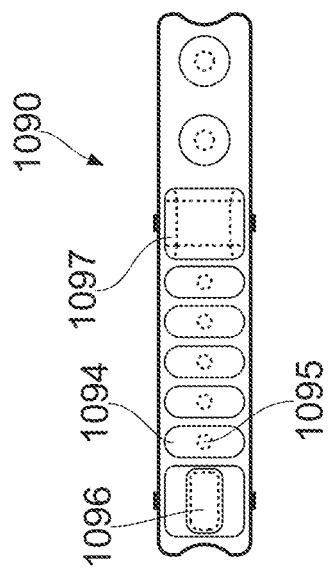

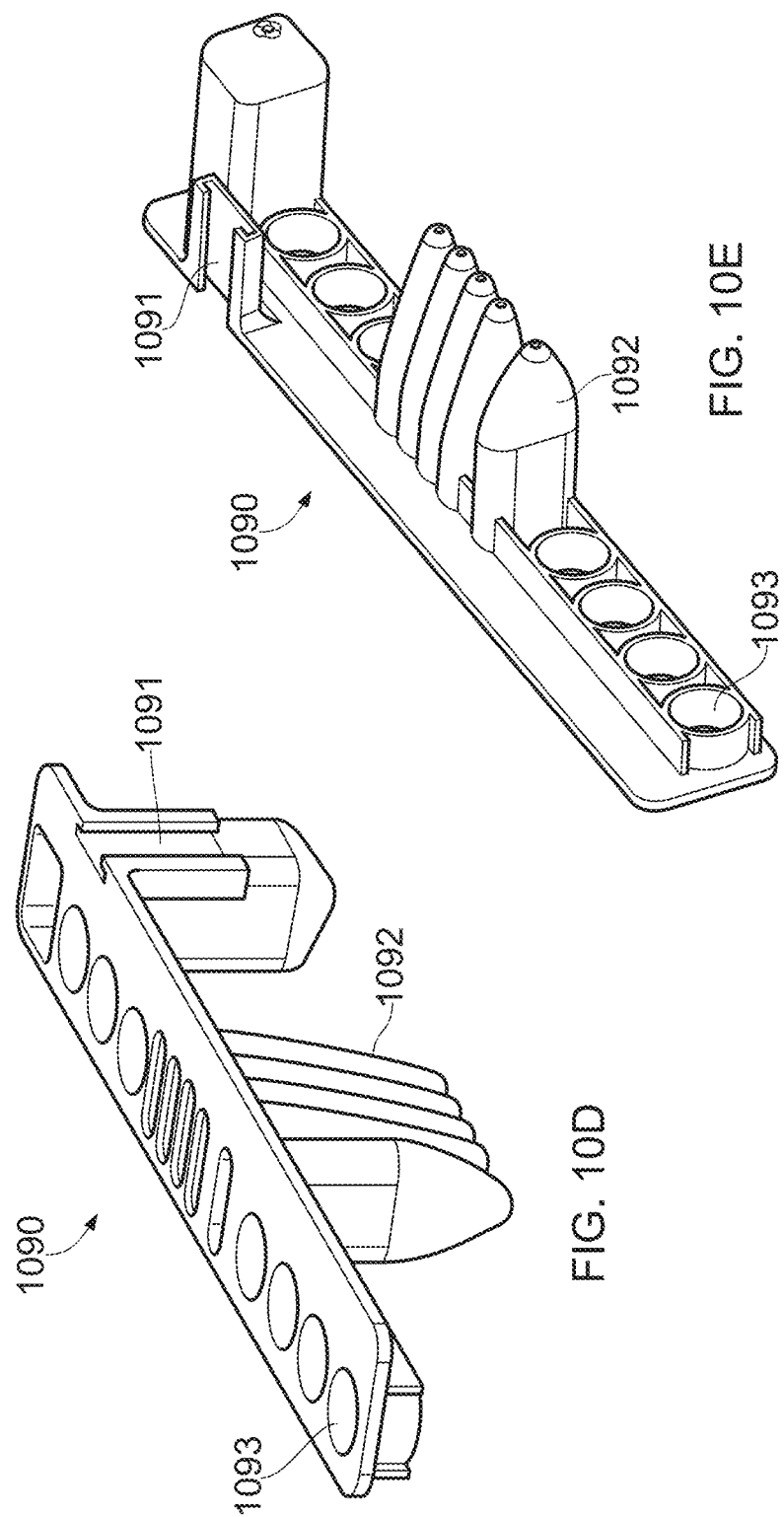

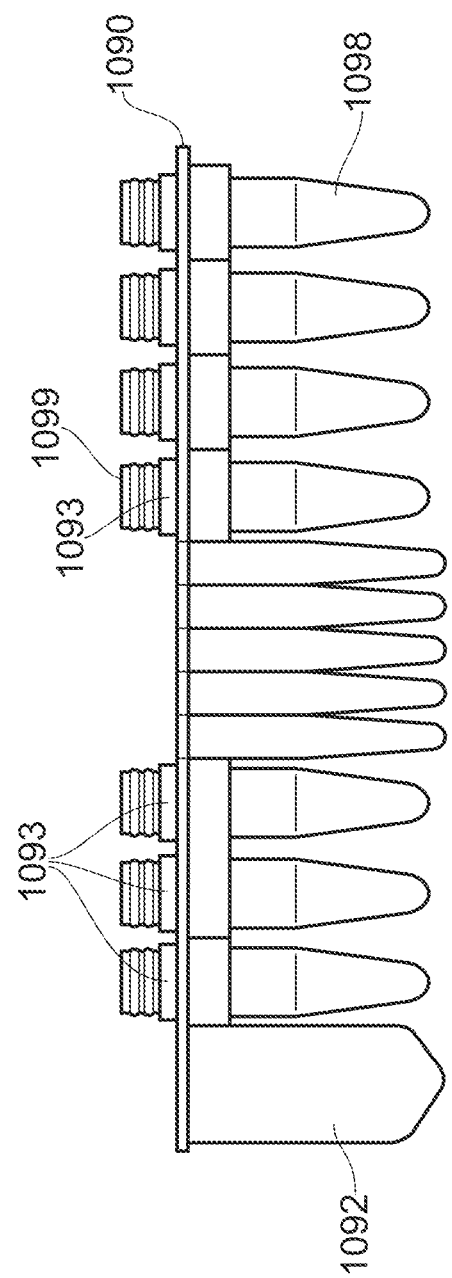

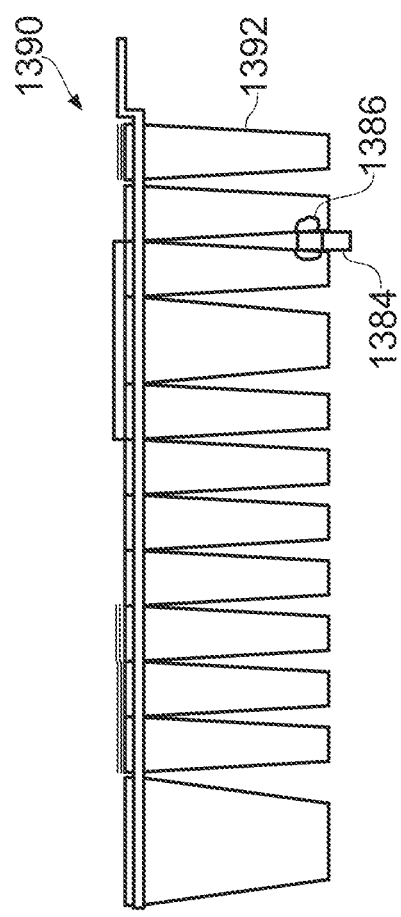
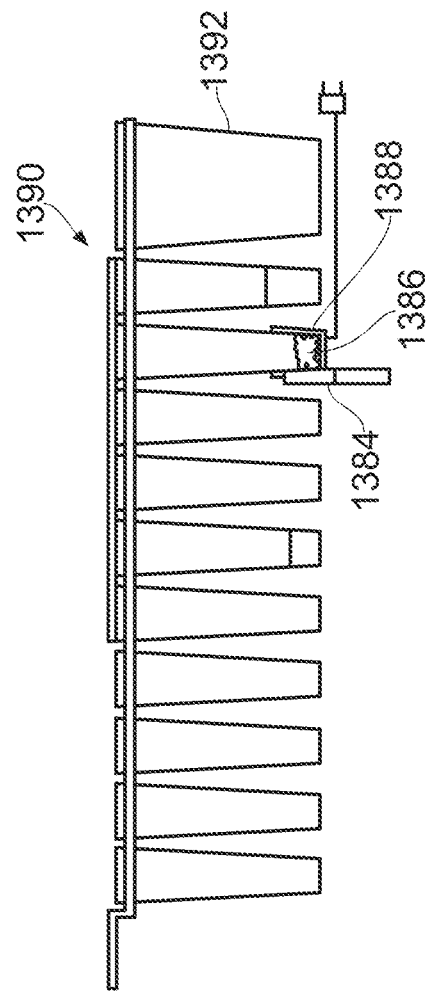

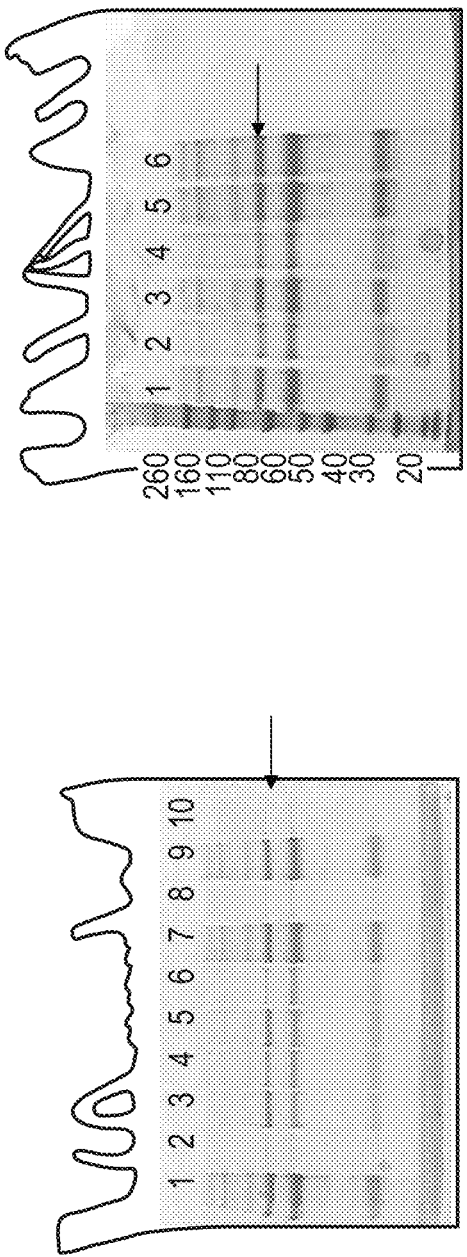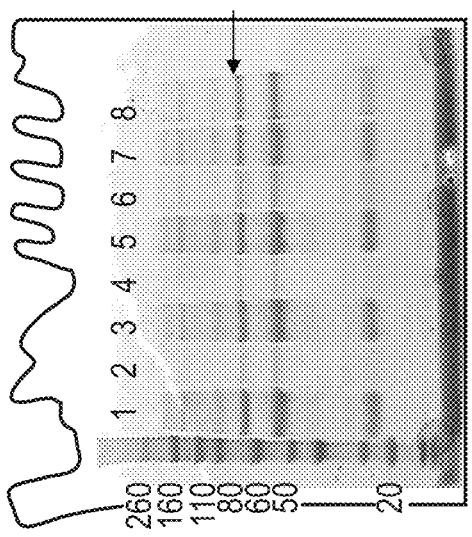
FIG. 16A
FIG. 16B
FIG. 16C

APPARATUS FOR AND METHOD OF
AUTOMATED PROCESSING OF
BIOLOGICAL SAMPLES

CROSS-REFERENCE TO RELATED APPLICATIONS

This application is a 371 U.S. national phase of International Application No. PCT/EP2010/056510 filed May 10, 2010, which claims priority to U.S. Provisional Application No. 61/309,371 filed Mar. 1, 2010 and U.S. Provisional Application No. 61/177,628 filed May 12, 2009, the disclosures of which are incorporated herein by reference in their entirety. This application also claims priority to United Kingdom Application No. 0916965.7, filed Sep. 28, 2009, which disclosure is incorporated herein by reference in its entirety.

FIELD OF THE INVENTION

The present invention relates to devices, methods and systems for processing biomolecules and more specifically to automated methods, systems and devices for processing biomolecules using magnetic particles.

BACKGROUND OF THE INVENTION

Magnetic particles may be employed as a solid phase in various methods for isolation and purification of biomolecules. The majority of such procedures are either carried out using inefficient manual methods which require individual attention by the scientist or lab technician performing the procedure, or they are automated for use with large and complex robotic instruments.

Manual methods may be time-consuming and may suffer from human error and lack of reproducibility inherent in manually intensive procedures. Automated methods are hampered by the need for bench space for large and more costly instruments.

The method of operation for the existing systems may be based on three different platforms. One platform is the standard liquid handling robots used for high-throughput methods which has been modified for work with magnetic particles. On such instruments the magnetic separation is either performed on an integrated magnet station, or the microtiter-plates or tube-trays containing the beads are moved by a robotic arm to an external magnet. Typical examples of such robots are the Tecan Genesis® and Tecan Freedom EVO™ (Tecan AG, Switzerland) and the Biomek® FX and Biomek® 2000 (Beckman Coulter Inc., USA). Other robots are designed specifically for use with magnetic beads. WO 94/18565 and WO 96/12958 disclose technologies where the robot uses elongated removers with either longer magnetic rods or short magnetic tips covered with elongated disposable plastic sheaths to move beads from one solution to the next. As the remover is introduced into a mixture with the magnet in lower position inside the sheath, the particles adhere to the surface of the remover and can thus be removed from the mixture. When the magnet is pulled into upper position, the particles are detached from the surface of the remover. The device may include multiple removers operating in parallel so as to allow simultaneous treatment of multiple samples. Such separating techniques have also been commercially implemented in the KingFisher® separating devices of Thermo Electron Oy, Finland. The robots based on the Magtration® technology (Precision Systems Science Co., Ltd., Japan) as described in EP 0763739, are equipped with unique pipette heads with magnets positioned directly behind the pipette tips. The pipette tip system is further described EP 0965842. The magnetic separation is performed inside the pipette tips. Another type of magnetic particle or bead processing instruments are those used for in-vitro diagnostic reactions. Such instruments are for example described in WO93/20440 and WO2006/099255.

What is needed, and what is provided herein is a small, affordable, user-friendly and flexible instrument for reactions performed on solid supports like magnetic particles or beads. This instrument differs from existing robotic instruments in its simplicity with a low number of movable parts while still being fully automatic. This makes the instrument cheaper in production and less prone to hardware failure. The instrument is meant to work with several different bead sizes and for a multitude of different protocols. Typical reactions would be pre-proteomics sample preparation, nucleic acid applications, and cell separation applications, all with increased convenience of use, reduced labor time and increased reproducibility.

In addition, what is needed, and what is provided herein are systems and methods for operating a small, affordable, user-friendly and flexible instrument for reactions performed on solid supports like magnetic particles or beads.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

Provided herein is a bioprocessing device and bioprocessing card for automated processing of a biological sample. In some embodiments, the device may be used for protein or nucleic acid sample preparation, other protein or nucleic acid applications, and cell separation applications using magnetic beads. In some embodiments, the device and bioprocessing card provided herein may be used to perform automated immunoprecipitation, chromatin immunoprecipitation, recombinant protein isolation, nucleic acid separation and isolation, protein separation and isolation, cell separation and isolation, automatic bead based separation, any combination thereof, or any other suitable bioprocessing of a sample.

Further provided herein is a bioprocessing card comprising a plurality of pipette tips; and at least one pump in fluid communication with the plurality of pipette tips. In some embodiments, the plurality of pipette tips may be at least two pipette tips, at least three pipette tips, at least 4 pipette tips, at least five pipette tips, at least seven pipette tips, at least ten pipette tips, at least 12 pipette tips. The plurality of pipette tips and the at least one pump may be in fluid communication through a processing channel. In some embodiments, the processing channel may be a microscale channel. In some embodiments, the processing channel may be a mesoscale channel. In some embodiments, the bioprocessing card may include at least three pumps. Additionally, the bioprocessing card may include a plurality of control fluid connectors. The individual control fluid connectors may be configured to be in communication with the individual pipette tips. In some embodiments the control fluid connector may be configured to be in communication with the at least one pump. The plurality of control fluid connectors may be configured to be in communication with an air supply source. In some embodiments, the bioprocessing card may include a plurality of valves wherein each valve is in communication with a pipette tip. In some embodiments, the bioprocessing card may include a membrane such as, for example, a silicone membrane. In some embodiments, the bioprocessing card may further include a sealing foil.

Further provided herein is an automated bioprocessing device comprising at least one bioprocessing card; at least one fluidic cartridge; and an automated control system configured to control automated bioprocessing of a sample. In some embodiments, the device may include more than one bioprocessing card and more than one fluidics cartridge. In some embodiments, the device may include a manifold in communication with the bioprocessing card, wherein the manifold is configured to apply atmospheric pressure, vacuum, and/or pressure to the bioprocessing, card. In some embodiments, the manifold may be external to the device. In some embodiments, the manifold may be internal to the device. In some embodiments of the device, the device may further include a heating and/or cooling block. In some embodiments, the device may further include a magnetic assembly. In some embodiments, the device may further include a graphical user interface (GUI). In some embodiments, the device may further include a control panel. The fluidics cartridge of the device may, in some embodiments, include at least one cartridge well. The fluidics cartridge may further include an opening configured to receive a container configured to contain and confine a liquid. The cartridge well may include a solid support, such as, for example, a magnetic particle, magnetic bead, or any other suitable solid support. In some embodiments, the bioprocessing card may be any embodiment of a bioprocessing card described previously. In some embodiments, the bioprocessing card may include a plurality of pipette tips; and at least one pump in fluid communication with the plurality of pipette tips.

Further provided herein is a method for processing a sample comprising: providing an automated bioprocessing device comprising: a bioprocessing card; and a fluidics cartridge containing the sample; selecting a protocol; and running the protocol. The fluidics cartridge may include at least two cartridge wells and in some embodiments, a magnetic particle may be located in at least one of the cartridge wells. In some embodiments, each cartridge well may be configured to hold a fluid. The bioprocessing card may include a plurality of pipette tips; and at least one pump in fluid communication with the plurality of pipette tips. In some embodiments of the method, running the protocol may include aspirating a fluid from a first cartridge well located on the fluidics cartridge using a first pipette tip; transporting the fluid through a processing channel to a second pipette tip; and expelling the fluid through the second pipette tip into a second well located on the fluidics cartridge. The aspirating, transporting, and expelling may be repeated any number of times as desired. In some embodiments, the processing channel may be a mesoscale channel. In some embodiments, the processing channel may be a microscale channel. In some embodiments the fluid may be selected from at least one of a buffer, reagent, wash, proteinase, antibody, sample, or eluate. In some embodiments, the bioprocessing device may include a magnetic assembly. In some embodiments, the method includes applying a magnetic field to at least a portion of the fluidics cartridge; attracting at least one magnetic particle located in the fluid in a cartridge well; removing the fluid from the cartridge well. In some embodiments, the method further includes resuspending the magnetic particle in a fluid. In some embodiments, the bioprocessing device includes a heating/cooling block. The method may include heating and/or cooling at least a portion of the fluidics cartridge.

Further provided herein is an automated method of bioprocessing comprising: a) inserting at least one fluidics cartridge into a bioprocessing device, said fluidics cartridge comprising at least one cartridge well containing at least one fluid; b) inserting at least one bioprocessing card into the bioprocessing device, said bioprocessing card comprising: i) a plurality of pipette tips; and ii) at least one pump in fluid communication with the plurality of pipette tips; c) initiating a bioprocessing protocol on the bioprocessing device, the protocol comprising one or more of the following: i) controlling pumps and valves on the bioprocessing card to transfer fluids, reagents and/or samples between one or more cartridge wells, ii) controlling pumps and valves on the bioprocessing card to mix fluids, reagents and/or samples in a cartridge well; and/or iii) controlling pumps and valves on the bioprocessing card to remove fluids, reagents and/or samples from the at least one cartridge well.

Also provided herein is a method of applying one or more fluids to a solid support comprising the steps of: a) inserting at least one fluidics cartridge into a bioprocessing device, the fluidics cartridge comprising one or more cartridge wells containing a solid support therein; b) inserting at least one bioprocessing card into the bioprocessing device, the bioprocessing card comprising: i) a plurality of pipette tips; ii) at least one pump in communication with the plurality of pipette tips; and c) performing a pumping sequence on said card, wherein said pumping sequence comprises entering one or more processing cycles wherein fluid is pumped between the one or more cartridge wells through the processing channel of the bioprocessing card.

In some embodiments, provided herein is a system for sample bioprocessing, comprising: a. a fluidics cartridge that includes a first well and a second well, wherein the first well holds a fluid sample that includes one or more magnetic particles; b. a bioprocessing card that includes a first pipette tip, a second pipette tip, and a pump that are in fluid communication along a processing channel and that is placed in proximity to the fluidics cartridge so that the first pipette tip is in fluid communication with the first well and the second pipette tip is in fluid communication with the second well; c. a manifold that is in physical communication with the bioprocessing card; d. a magnetic assembly that is placed in proximity to the fluidics cartridge; e. a memory that includes instructions for a sample preparation protocol; and f. a processor that is in electronic communication with the manifold, the magnetic assembly, and the memory, that reads the instructions from the memory, and that according to the instructions: i. activates the magnetic assembly to apply a magnetic field to the first well so that at least one magnetic particle of the one or more magnetic particles of the fluid sample is attracted; and ii, signals the manifold to apply pressure and/or vacuum to the bioprocessing card activating fluid valves of the first pipette tip, the second pipette tip, and the pump to move a portion of the fluid sample from the first well through the processing channel, to the second well producing a bioprocessed sample in the first well. In some embodiments, a system further comprises a heat/cooling block that is placed in proximity to the fluidics cartridge, that is in electronic communication with the processor, and that receives a signal from the processor to heat or cool of the fluidics cartridge according to the instructions.

In some embodiments, a system for sample bioprocessing as provided herein further comprises a card actuator to move the bioprocessing card with respect to the fluidics cartridge so that the depths of the first pipette tip and the second pipette tip in the first well and the second well can be varied, wherein the card actuator is in electronic communication with the processor and receives a signal from the processor to move the bioprocessing card according to the instructions. In some embodiments, a system for sample bioprocessing as provided herein can further comprise a cartridge actuator to move the fluidics cartridge with respect to the bioprocessing card so that the first pipette tip can be moved from the first well to the second, wherein the cartridge actuator is in electronic communication with the processor and receives a signal from the processor to move the fluidics cartridge according to the instructions. In some embodiments, the processor uses the card actuator and the cartridge actuator in concert to move fluid from the first well to the second well using the first pipette tip.

In some embodiments, a system for sample bioprocessing as provided herein further comprises an input/output device from which the processor can also read the instructions, wherein the input/output device is in electronic communication with the processor. In some embodiments, the bioprocessing card comprises a check valve.

In some embodiments, a system for sample bioprocessing as provided herein can comprise: a. the processor signals the manifold to apply pressure and/or vacuum to the bioprocessing card to close the check value and open all other card valves, b. the processor signals the manifold to increase the pressure of the bioprocessing card to a system pressure, c. the processor signals the manifold to open the check value, and d. if the processor receives a system pressure from the manifold at the check value, then the processor determines that the bioprocessing card is present.

In some embodiments, a system for sample bioprocessing as provided herein can further comprise a user interface device from which the processor receives a protocol selection from a user, wherein the input/output device is in electronic communication with the processor. In some embodiments, the processor receives a protocol parameter from the user interface device that indicates a parameter selected by the user. In some embodiments, the processor sends a system status to the user interface device.

In some embodiments, the instructions comprise a scripting language format. A non-limiting exemplary scripting language format comprises a bioprocessing sequence. hi some embodiments, a bioprocessing sequence comprises a step and the processor translates the step into a processing device signal.

In some embodiments of a system for sample bioprocessing as provided herein, the manifold applies pressure and/or vacuum to the bioprocessing card by activating one or more manifold valves of a plurality of manifold valves on the manifold. For example, the manifold activates the one or more manifold values using a matrix of address lines to allow more than one bioprocessing card to perform the sample preparation protocol at substantially the same time. In some embodiments, each manifold valve of the plurality of manifold valves can be addressed using two address lines of the matrix of address lines.

In some embodiments, provided is a method for sample bioprocessing, comprising: a. reading instructions for a sample preparation protocol from a memory using a processor; b. activating a magnetic assembly to apply a magnetic field to a first well of a fluidics cartridge so that at least one magnetic particle of one or more magnetic particles of a fluid sample is attracted using the processor, wherein the fluidics cartridge includes the first well and a second well, wherein the first well holds the fluid sample that includes the one or more magnetic particles, and wherein the magnetic assembly is in proximity to the fluidics cartridge; and c. signaling a manifold to apply pressure and/or vacuum to a bioprocessing card activating fluid valves of a first pipette tip, a second pipette tip, and a pump to move a portion of the fluid sample from the first well through a processing channel, to the second well producing a bioprocessed sample in the first well using the processor, wherein the bioprocessing card includes the first pipette tip, the second pipette tip, and the pump that are in fluid communication along a processing channel, wherein the bioprocessing card is in proximity to the fluidics cartridge so that the first pipette tip is in fluid communication with the first well and the second pipette tip is in fluid communication with the second well, and wherein the manifold is in physical communication with the bioprocessing card.

In some embodiments, provided herein is a computer program product, comprising a tangible computer-readable storage medium whose contents include a program with instructions being executed on a processor so as to perform a method for sample bioprocessing, comprising: a. providing a system, wherein the system comprises distinct software modules, and wherein the distinct software modules comprise a protocol translation module, a magnetic assembly module, and a liquid transfer module; b. reading instructions for a sample preparation protocol using the protocol translation module; c. activating a magnetic assembly to apply a magnetic field to a first well of a fluidics cartridge so that at least one magnetic particle of one or more magnetic particles of a fluid sample is attracted using the magnetic assembly module, wherein the fluidics cartridge includes the first well and a second well, wherein the first well holds the sample that includes the one or more magnetic particles, and wherein the magnetic assembly is in proximity to the fluidics cartridge; and d. signaling a manifold to apply pressure and/or vacuum to a bioprocessing card activating fluid valves of a first pipette tip, a second pipette tip, and a pump to move a portion of the fluid sample from the first well through a processing channel, to the second well producing a bioprocessed card includes the first pipette tip, the second pipette tip, and the pump that are in fluid communication along a processing channel, wherein the bioprocessing card is in proximity to the fluidics cartridge so that the first pipette tip is in fluid communication with the first well and the second pipette tip is in fluid communication with the second well, and wherein the manifold is in physical communication with the bioprocessing card.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2D shows various views of the drawers of the device;

FIGS. 5A-5C show various views of the exterior of an embodiment of a card for use with the device;

FIG. 5D shows an alternate embodiment of a card for use with the device;

FIGS. 6A-6G shows various views of an embodiment of a card for use with the device;

FIGS. 9A-9C illustrate an embodiment of a membrane for use with the card;

FIGS. 10A-10C illustrate various views of an embodiment of a fluidics cartridge; FIGS. 10D-10F illustrate various views of another embodiment of a fluidics cartridge;

FIGS. 13A & 13B shows various embodiments of a magnetic assembly interacting with the fluidics cartridge;

FIGS. 16A-16C show results generated using the device compared;

DETAILED DESCRIPTION OF THE INVENTION

Figure 1B:
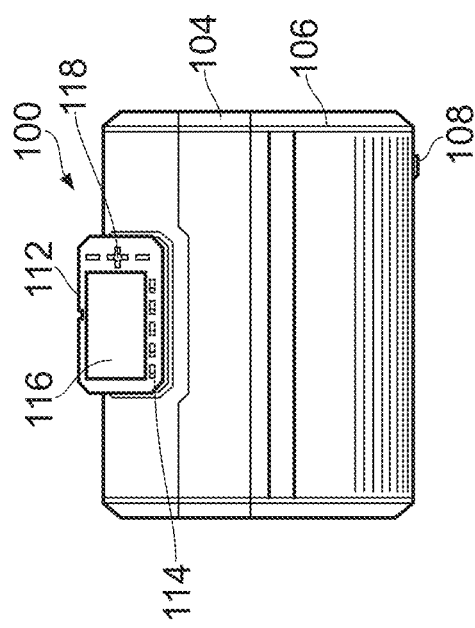
FIGS. 1A-1H shows various exterior views of the device.

Provided herein are bioprocessing devices and bioprocessing cards and fluidic cartridges for use with bioprocessing devices, and also systems and methods for operating bioprocessing devices that include bioprocessing cards and fluidics cartridges. In some embodiments, automated bioprocessing devices comprise automated devices for performing one or more protocols for processing biomolecules. In some embodiments, bioprocessing devices may be configured to run protocols and bioprocessing procedures selected from: immunoprecipitation, chromatin immunoprecipitation, recombinant protein isolation, nucleic acid separation and isolation, protein labeling, separation and isolation, cell separation and isolation, utilizing automatic bead based separation, preferably magnetic particle or bead based separation.

I. Device

Provided herein is a bioprocessing device for automated processing of a sample. The bioprocessing device may have a housing that may include separate panels for the front, back, top and side panels. The housing may be made of metal, plastic, a combination thereof, or any other suitable material. In some embodiments, the device may have a single drawer or multiple drawers, for example, a top drawer and a bottom drawer. The drawers may be pull-out drawers or may include doors on hinges capable of allowing access to the interior of the device. In some embodiments, vents may be located along at least a portion of the housing to provide heat dispersion from the components on the inside of the device. The vents may be located on either the front, back, sides of the device or on at least one of these areas. The device may further include a computer control system comprising a control panel with which the user may interact with the device. The control panel may include control buttons and a graphical user interface (GUI). The top drawer may be used to load a card for bioprocessing a sample and the bottom drawer may be used to load tubes or cartridges for samples and reagents used for bioprocessing.

The housing of the device may be attached to the device with any suitable attachment mechanism including screws or welding. In some embodiments, a power switch and a power supply connector may be located at the back of the device. The control panel may include selection or control buttons and directionality keys for selecting items or increasing or decreasing parameters. In some embodiments, the control panel may be a touch panel. Additionally, the control panel may be powered by a separate power button on the control panel or may be powered by the main power switch on the device. In some embodiments, the control panel may include an interface which may provide for upload of information onto the device or download of the process parameters used for any run directly onto a computer via a direct connection, such as an Ethernet port, a Personal Computer Memory Card International Association (PCMCIA) slot or a universal serial bus (USB) port. In some embodiments, the upload or download of information may be done using a wireless connection, a portable storage medium such as a flash drive or thumb drive, a writable CD-ROM, or DVD or the device may be connected to a network, such as a LAN or WAN or to an internet-based application. The steps of a protocol and the time required for each step of a protocol being performed by the device may be shown on the GUI. Additional steps may also be shown with the user option of selecting or deselecting one or more of the steps for the protocol.

The computer control system through the control panel may be used to control the actuation of one or more process valves on the bioprocessing card and thus the amount of one or more process fluids transported through the mesoscale or microscale fluid flow channel in connection with the pipettes on the card, mixing of one or more process fluids, determine the exposure time of one or more solid supports to one or more process fluids, pumping and flow paths of one or more process fluids, circulation of one or more process fluids, pumping flow rates, sequence and volume of process fluid addition and/or purging from one or more cartridge wells on the fluid container cartridge.

The computer control system through the control panel may interface with an external operator input system which may include any appropriate input system, such as a keyboard, keypad, mouse, touch-screen or any other suitable device used by users to interact with computer systems and to run software or firmware. The software or firmware used in the bioprocessing device may be application specific or may be commercial off the shelf software. In some embodiments, the bioprocessing device may include sensors for monitoring the progress of one or more protocols running on the device. For example, the device may include pressure and vacuum sensors for measuring the pressure and vacuum supplied during various steps of the protocol, flow rate sensors, temperature sensors, time lapse sensors, sensors for measuring any parameters associated with one or more steps of processes performed on the device. The sensors may provide passive measurement of various parameters that may be recorded in the control system or may provide active measurement that may be used for control of the progress and conduct of the process. Such control may occur using any suitable control procedure, including, but not limited to proportional, integral, proportional-integral or proportional-integral-derivative control.

In some embodiments the computer control system may control the movement of the magnetic assembly and the time a magnetic bead based solid phase is exposed to a magnetic field. The magnetic assembly may include a magnet or any other suitable mechanism for creating a magnetic field. In some embodiments the computer control system is configured to either turn on and off an electromagnet on the magnetic assembly or is able to control the lift of the magnetic assembly up towards the bottom of a cartridge well when permanent magnets are used. In some embodiments, the device may include a manifold for supplying atmospheric pressure, pressure and/or vacuum to the bioprocessing cards. In some embodiments, the computer control system may also control the movement of the manifold towards bioprocessing card plate, and the further movement of these two components towards the heating/cooling block. Such horizontal movements of the magnetic assembly, the manifold, and the manifold together with the bioprocessing card plate may be done either by the use of pumps driven by pressurized air or by motorized pumps. In some embodiments, the device includes a heating/cooling block for heating and/or cooling a fluid contained in at least one well of a microfluidics cartridge. In some embodiments the computer control system is configured to regulate and control the temperature of the heating/cooling block by regulating the current applied to the Peltier elements.

In some embodiments, the automated control system is able to perform the same or different protocols on multiple bioprocessing cards in the device using the same types or different types of sets of fluid container cartridge having the same type or different types of wells, reagents and samples for each protocol. During processing, the GUI may provide for the user to observe the progress of the one or more protocols being performed and the computer control system may provide for alarms to indicate completion of the processing or errors or other problems that may occur during processing. In some embodiments, the bioprocessing device and/or the computer control system also includes safety interlocks that prevent the device from running a protocol if the device is in one or more unsafe or unprepared states, such as, by way of non-limiting example, any tray or rack is not fully inserted into the slots on the device, one or more cartridges or cards are not properly inserted into the slots on the device or on any tray or rack, or the bioprocessing card are not properly connected to the air and/or vacuum supply, the air or vacuum supply is inadequate, the air or vacuum supply exceeds safety limits and/or the electrical supply is inadequate or exceeds safe limits.

The top drawer of the device may include a plate with at least one card slot into which a bioprocessing card for use with the device may be placed. In some embodiments, the plate has at least one card slot, at least two card slots, at least three card slots, at least ten card slots, at least twelve card slots. At least one bioprocessing card may be positioned in one of the card slots and may further be supported by the plate. In some embodiments, from 1 to 20 cards, such as 1 to 15, 1 to 14, 1 to 12, 1 to 10, 1 to 5, or at least one card, at least two cards, at least five cards, at least ten cards, at least twelve cards may be loaded on the plate. In some embodiments, the plate may include notches to lock the card in place in a card slot. Slides attached to the plate may be included to facilitate drawing out and pushing in the drawer after the card or cards are loaded onto the plate. In some embodiments, the slides may be attached at the sides of the plate or under the plate.

In some embodiments, the bottom drawer may include a heating/cooling block. In some embodiments, the heating/cooling block may be directly attached to the bottom drawer. In some embodiments, a plate may be attached to the bottom drawer and the heating/cooling block may be attached to the plate. The heating/cooling block may further include at least one cartridge slot, at least two cartridge slots, at least three cartridge slots, at least ten cartridge slots, at least twelve cartridge slots. The number of cartridge slots of the heating/cooling block may correspond to the number of cartridge slots in the plate of the top drawer. A fluidics cartridge may be positioned in a cartridge slot of the heating/cooling block.

A frame may be located under the housing. The top drawer may be attached to the frame via slides that may be located at the sides or bottom surface of the drawer. A suitable number of card slots may be located on the plate of the drawer to hold at least one card, at least two cards, at least five cards, at least ten cards, at least twelve cards. The card may be locked into place on the plate by interacting the card with a notch on the plate. In some embodiments, a manifold may be located in the frame which comes in contact with the top surface of the card when the top drawer has been retracted back into the frame. The heating/cooling block may be directly attached to the frame using slides positioned under the heating/cooling block. A suitable number of cartridge slots may be located on the heating/cooling block to hold at least one fluidics cartridge, at least two cartridges, at least five cartridges, at least ten cartridges, at least twelve cartridges. The number of fluid cartridges positioned in the heating/cooling block may equal the number of cards positioned in the top drawer. A height adjustment system may control movement of the plate of the top drawer relative to the heating/cooling block or movement of the heating/cooling block with respect to the top plate. In some embodiments, the slides may be attached to a support bar which may raise and lower the card plate following support guides. A connector attached to the support bar may then raise and lower the card plate. In some embodiments, the heating/cooling block may be raised and lower relative to the card plate. In some embodiments the temperature of the heating/cooling block may be regulated by the use of one or more Peltier elements.

In some embodiments, a manifold may be used to supply vacuum and/or pressure to the card. In some embodiments, the manifold may supply vacuum and/or pressure to the locations where a card is located or may supply vacuum and/or pressure regardless if a card is located in a position under the manifold. In some embodiments the manifold may supply pressure and/or suction to locations on the manifold corresponding to positions where a card is located. For example, the manifold may be mechanically sealed by a barrier that is displaced when a card is in communication with the manifold. In some embodiments, the system can be programmed so that portions of the manifold under which cards are located can be activated.

In some embodiments, the device may further include a manifold with valves/diaphragms to control which locations or cards receive pressure and/or suction. In some embodiments, there may be one single silicone membrane on the manifold per card as opposed to individual diaphragms for each valve/pump. Air, pressure and/or vacuum may be applied to control the state of the valves/pumps in the card. Air pressure to control each individual card may be introduced to the manifold as indicated by the solid line in FIG. 12B. This air pressure may be applied to individual diaphragms in communication with the control fluid connectors on the card. Each valve in the manifold in communication with a control fluid connector may further include a diaphragm which may be used to override the control fluid represented by the dashed line in FIG. 12B. In some embodiments, the manifold may further include air flow restrictors, such as tubing with narrow inner diameters or any other suitable air flow restrictor.

In some embodiments, the manifold may be constructed in layers. The first or top layer may have valves and pumps to supply the individual valves on the card. The second and third layer of the manifold may house the valves for supplying vacuum/pressure to the card by the manifold. The manifold may include a single silicone membrane strip per card located in between the second and third manifold instead of individual diaphragms per valve/pump on cards. The bottom layer of the manifold may then interact with the cards.

In some embodiments of the manifold, vacuum and/or pressure may be supplied to the manifold using different connectors or may be supplied using the same connector. In some embodiments, the suction and/or pressure may be supplied by a house source or may be supplied by an air pressure source located in the device. Valves, which may or may not be electronic controlled valves may be located along the manifold and positioned above an area in communication with a card. The electronic valve may be in further communication with an air channel in the manifold. The air channel may have valves to supply air, pressure, and/or vacuum to the control valves on the card. Vacuum may be applied to suck liquid and/or materials into the card through an open valve. Vacuum or air may be used to first open a valve associated with an individual pipette tip. A pump may then be actuated to draw a sample into the card. The valve is then closed and another valve opened. The pump is then actuated again to expel the drawn in fluid from the pipette tip associated with a second pipette tip. The suction then switches to atmospheric pressure to stop suction. Pressure may then be applied to expel any liquid in the card through an open valve.

In some embodiments, the bioprocessing device may also include one or more magnetizing portions or magnetic assemblies localized underneath the removable fluid cartridges. The magnetic assemblies may provide a magnetic field, such as a high-gradient magnetic field that may attract and separate magnetic particles from a non-magnetic medium in which they are contained. The magnets assemblies may include electromagnets or permanent magnets. When electromagnets are used the device will include electronic supplies, such as cables needed for operation of such magnets. When permanent magnets are used the magnets may be movable relative to the cartridge well localized on the fluid container cartridge in order to apply or remove a magnetic field from a fluidic cartridge by placing the magnet adjacent to (or within) the fluidic cartridge or by moving the magnet away from (or out of) the fluidic cartridge. In one embodiment the magnets may be localized on one or more lift-able devices or magnetic assemblies where the one or more magnets may be moved simultaneously.

The magnets of the at least one magnetic assembly may be made of a ferrous magnetic material such as iron, steel or any other suitable ferrous material that may be temporarily or permanently magnetized. The magnets may alternatively be made from a permanent magnetic material such as ferrite, samarium cobalt or any other suitable permanent material. Preferably, the permanent magnets may be formed from a high performance rare earth alloy such as neodymium iron boron (NdFeB).

Figure 19:
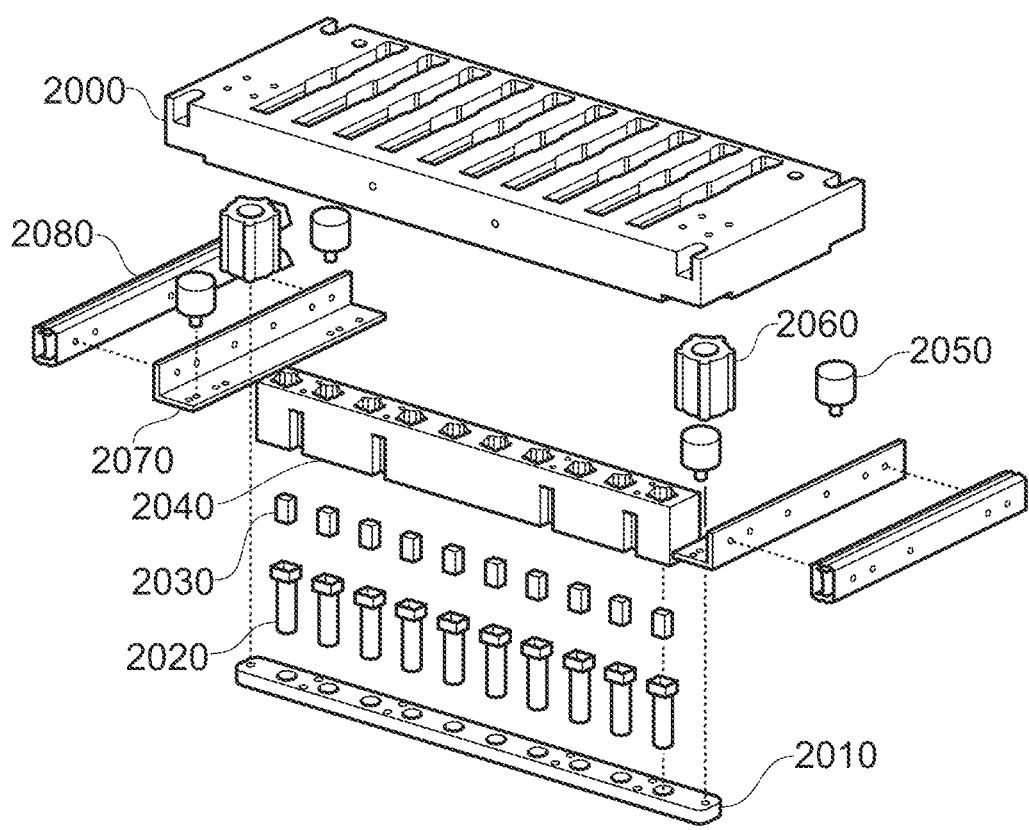
FIG. 19 illustrates an embodiment of the magnetic assembly

The ferromagnetic or permanent magnets may be rod, plate, bar or cube shaped and have a first pole end face (or surface) and a second pole end face (or surface). The ferromagnetic or permanent magnets preferably have substantially flat pole end faces (FEF) as shown in FIG. 19. However, the pole end face may be shaped to follow the contour of the cartridge well. For example, the pole end face of a magnet may be inclined end face (IEF) to follow the contour of the cartridge well. It has been found that the effects of a high-gradient magnetic field are further enhanced if the magnets are shaped to follow the contour of the cartridge wells, particularly smaller cartridge wells.

The magnets may be single magnets or composite magnets as described in International Patent Application No PCT/EP20081056650. The number, size and type of magnets on a magnetic assembly can be selected in accordance with the high-gradient magnetic field required to isolate the magnetically labeled particles from a non-magnetic medium, the size of the cartridge well and the region of the cartridge well to be subjected to the high-gradient magnetic field.

II. Bioprocessing Card

Provided herein is a bioprocessing card for automated processing of a sample. In some embodiments the bioprocessing card may include at least a body, at least two pipette tips located on the body in fluid communication with each other, and at least lone pump located in the body of the card. In some embodiments, the bioprocessing card may include one or more integrated mesoscale or microscale fluid flow channels for connection of one or more control fluid connectors to the bioprocessing card for operation of the integrated control valves localized above each individual pipette. As used herein, the term "microscale" refers to flow channels or other structural elements, having at least one cross-sectional dimension on the order of 0.1 μm to 1000 μm, such as 0.1 μm to 500 μm, 10 μm to 250 μm or 100 μm to 250 μm, and the term "mesoscale" refers to flow channels or other structural elements, having at least at least one cross-sectional dimension on the order of 1000 μm to 4 mm, such as greater than 1000 μm, greater than 1100 μm, greater than 1250 μm or greater than 1500 μm. Such connections, may, for example, include connection of a manifold in communication with each of the bioprocessing cards inserted in each card slot on the card plate. In some embodiments, the manifold may be configured to form a sealed connection with the control fluid connectors on each bioprocessing card within each slot. In some embodiments, the manifold may be connected or sealed to the bioprocessing card, in part, by using a gasket or O-ring. The manifold may include individual supply connectors for interacting with each of the control fluid connectors on the bioprocessing card. In some embodiments, the manifold may be urged onto or connected to the control fluid connectors on a bioprocessing card using a pressurizable, inflatable, flexible container, such as a sack or a bladder which, upon inflation, causes the supply connectors to move towards and to be connected, such as sealably connected, to the control fluid connectors on the bioprocessing card. In other embodiments, mechanical means such as spring loaded mechanisms or automatic or manual locking mechanisms may be used to connect the control fluid manifold to the control fluid connectors.

In some embodiments, the card may include a body, control fluid connectors located along the length of the body, a foot and notch for aligning and locking the card in place on the card plate of a bioprocessing device and at least one pump. In some embodiments, alignment holes may be located on the body of the card for aligning the parts of a card. At least one pipette tip may be located along the length of the body of the card and in some embodiments, may be located on the bottom surface of the card. In some embodiments the pipette tip lengths may vary with respect to each other, depending on the depth the pipette tip needs to extend. In some embodiments, the pipette tip lengths may be the same length. The pipette tips may be spaced uniformly along the length of the body of the card, or, alternatively the distance between pipette tips may be varied. In some embodiments, supports extend radially from the base of the pipette tip to provide extra support to the pipette tip. In addition to the pipette tips, pumps may be integrated with the card. A processing channel may transport fluid/solution/materials between the different individual positions along the length of the card. In some embodiments, the fluid/solution/material may be a sample, reagent, buffer, wash, a combination thereof, or any other suitable fluid/solution/material. In some embodiments, the material may be a magnetic particle including, but not limited to, magnetic beads.

In some embodiments, a card may have individual valves in communication, preferably fluid communication, with the pipette tips and control fluid connectors. In some embodiments, the pipette tips may be offset with respect to the control fluid connectors. A single membrane may be positioned along the length of the card or alternatively individual membranes may be positioned at the position of individual valves. In some embodiments, the membrane or membranes is/are a silicone membrane or membranes or any other suitable membrane may be used provided that the material is sufficiently flexible to serve as a valve/pump and sufficiently robust to withstand the relevant operating conditions. The membrane or membranes may have a length that may or may not be predetermined prior to assembling the card. The membrane or membranes may either have a predetermined shape to fit the contours of the card or may conform to the contours of the card after being inserted into the card. In some embodiments, the membrane or membranes may have a predetermined length and/or width substantially similar to the length of the card. Alternatively the membrane or membranes may be modified prior to or after assembly to the desired shape to fit the card.

In some embodiments, a single membrane may span the length of the card or individual membranes may be positioned in the card over the locations forming the individual valves and/or pumps. In some embodiments, the membrane may be a silicone membrane. Where the control fluid connectors and the pipette tips are located on two separate pieces, the membrane or membranes may be placed between the top and bottom parts of the card before the two parts are assembled together. In some embodiments, the membrane, the card, or both the membrane and the card may include fixtures, markers, alignments guides to aid in the correct placement of the silicone membrane between the card pieces before the card it welded together.

The pipette tip and control fluid connector may be offset relative to each other to facilitate the opening and closing of the valve or membrane located between the pipette tip and the control fluid connector. The offset nature of the fluid connector and the pipette tip allows the valve to be open and allow fluid to enter the valve above the pipette tip and move into the processing channel. An opening located at the end of the processing channel facilitates the transfer of materials and/or fluids between the different valves. In some embodiments, an alignment hole may be located on the card to align the parts of the card before assembly.

The processing channel may transfer fluid the volume of fluid pumped through each of the individual valves. Each pump on the card may be in communication with a control fluid connector each of which has an opening and a center through which suction or pressure can be supplied to facilitate the functioning of the pumps. Each pump may further have a connector which connects the pump to the processing channel. Each pump may also have a membrane that expands and contracts during pump operation.

In some embodiments of the card, the card may further include an edge. The edge may interact with a manifold for supplying suction and/or pressure to the card. The at least two pipette tips may extend from the bottom of the card and in some embodiments supports extending radially from the base of the pipette tip may offer support for the connection between the card and the pipette tip. In some embodiments, the diameter of the pipette tip may remain constant along the length of the pipette tip or alternatively, the diameter of the pipette tip may vary along the length of the pipette tip. The interior diameter of the pipette tip which forms the center portion of the pipette tip may remain constant along the length of the pipette tip or may vary along the length of the pipette tip. In some embodiments, the end of the pipette tip may taper. An opening may be located at the end of the pipette tip into which fluid may be aspirated and from which fluid may be expelled.

In some embodiments, the card may be a constructed as a single piece. In some embodiments, the fluid connectors may be located on one part of the card and the pipette tips on another card part and then the two card parts assembled together. As used herein, the use of the term card shall mean either a card constructed as a single piece or a card constructed from two or more pieces. Where the card is made from two pieces, the pieces may be assembled together using ultrasonic welding, welding, glue, adhesives, thermal sealing or thermal adhesives, any combination thereof, or any other suitable mechanism for assembling the two pieces together. In some embodiments, the length of the first piece and the second piece are substantially the same length or the lengths may vary with respect to each other. The edge of one piece may fit together with the edge of the second piece. In some embodiments, control fluid connectors may be located on the card that provide communication with atmospheric pressure to equilibrate the pressure inside the valves/pumps or channels of the card. In some embodiments, a membrane strip may be inserted between the supply connector layer and the pipette tip layer or individual membranes may be placed in the location of valves located between the control fluid connectors and/or pumps.

Where ultrasonic welding is used to assemble the card, the ultrasonic welding may be performed by any suitable ultrasonic welder (such as a Herrmann Computer Numberic Controlled (CNC) Ultrasonic Welding System, Serial Number SM9132/08).

The card or card pieces may be made from any suitable plastic, polypropylene, a nucleated polymer, any combination thereof, or any other suitable material for injection molding. In some embodiments, the card or card pieces may be a polypropylene homopolymer (for example, Metocene X50109 Polypropylene Homopolymer).

Further provided herein is a card that may further including a sealing foil for sealing the card. The sealing foil may have a length that may or may not be substantially the same length as the card. In some embodiments, the length of the sealing foil may be a predetermined length based on the length of the card. In some embodiments, the sealing foil may differ in length from the card and may be sized to fit the card either before or after sealing the card. The sealing foil may seal the card so that the seal is air tight or substantially air tight. In some embodiments, the sealing foil may further include alignment holes for aligning the sealing foil with the card. After the card has been assembled, a sealing foil may be attached to the assembled card.

In some embodiments, the sealing foil may be attached to the card using glue, adhesives, heat sealing, or any other suitable mechanism for attaching the sealing foil to the card. In some embodiments, the sealing foil may be attached to the card using heat sealing. The sealing material may first be placed in position over the card. Heat is then applied, preferably evenly, over the card for several seconds to weld the sealing foil to the card. The sealing foil may be attached to the bottom of the card. In some embodiments, the sealing foil, the card, or both the sealing foil and the card may be equipped with markers or alignment features to aid in the correct placement of the sealing foil with respect to the card. A thermal press (such as C-Frame Precision Thermal Press C-25MM, Serial number C25MM08122901 from Thermal Press International Inc.) may be used to attach the foil to the card. In some embodiments, the sealing foil may be, for example purposes only, REMP Peircable Thermo-Seal, Removable Thermo-Seal, Extra-Durable Removable Thermo-Seal, Clear Thermo-Seal, any combination thereof, or any other suitable sealing foil.

In some embodiments, after the card has been assembled, the functionality of the card may be verified and/or assessed.

III. Fluidics Cartridge

In some embodiment a fluidics cartridge is also provided. The fluidics cartridge may have at least one, at least two, at least five, at least ten, at least twelve, or more than twelve cartridge wells, such as reagent, waste, and/or sample wells. The number of cartridge wells may or may not be the same as the number of pipette tips located on a card for manipulating fluids in the fluidics cartridge. Each cartridge well may have an opening in communication, preferably fluid communication, with the pipette tips of the card. In some embodiments, the fluidics cartridge may include features for aligning, positioning, and/or retaining the fluidics cartridge with respect to the heating/cooling block. The feature may be a notch, groove, physical structure, or any other suitable feature for aligning, positioning, and/or retaining the fluidics cartridge with respect to the heating/cooling block of the device. In some embodiments, the fluidics cartridge may be constructed with a predetermined number of cartridge wells. In some embodiments, the cartridge wells of the cartridge may or may not be of the same shape, volume and/or size relative to the other cartridge wells on the same cartridge. In some embodiments, the cartridge wells may all be the same shape, volume, size, and/or length relative to each other. In some embodiments, the cartridge may be constructed so that some of the cartridge wells are prefabricated with the cartridge while other positions are constructed so that wells can be added to the cartridge or tubes or other fluid containers that may be inserted into the cartridge. The bottoms of the wells may be any suitable configuration to facilitate aspiration of the fluid out of the wells when necessary. The fluidics cartridge may be constructed as a single piece, at least two pieces, or more than two pieces. The card or card pieces may be made from any suitable plastic, polypropylene, nucleated polymer, any combination thereof, or any other suitable material for injection molding. In some embodiments, the card or card pieces may be a polypropylene homopolymer (for example, Metocene X50109 Polypropylene Homopolymer). In some embodiments, the shape of the cartridge wells may be configured so that it is easy to aspirate all liquid. In some embodiments, the shape of one or more of the well next to the magnet may be configured to accommodate a magnetic assembly. In some embodiments, the cartridge wells of the fluidics cartridge may be configured so that the ends of the pipette tip tips may be very close relative to the bottom of the cartridge wells of the cartridge in order to get full transfer of solution/liquid/materials without interfering with the opening of the pipette tips.

In some embodiments, the cartridge wells of the fluidics cartridge may contain, for example purposes only, samples, reagents and antibodies, buffers including elution and resuspension buffers, washes, magnetic particles or other materials, solutions, or any other suitable liquid/material/solution. In some embodiments, the liquid/material/solution may be added to an empty, non-sealed cartridge well, or to a microcentrifuge tube that may then be placed into the cartridge, or the cartridge well may be preloaded with a liquid/material/solution. In some embodiments, the cartridge well may be sealed after adding the liquid/material/solution to the well.

In some embodiments, the one or more of the cartridge wells may contain a solid support. The solid support may be any suitable support or matrix for immobilization and/or separation of materials from solution. Examples of solid support include, but are not limited to, particles, sheets, gels, filters, membranes (e.g. nylon membranes), fibers, or any other suitable solid support material. In some embodiments, the solid support may be made of glass, silica, latex, plastic or any suitable polymeric material. The surface of the solid support may be hydrophobic or hydrophilic and in some embodiments the solid support may be a material presenting a high surface area for binding, for example porous or particulate e.g. particles, fibers, webs, sinters or sieves. In some embodiments, the particulate material may be beads, such as, for example, polymeric beads/particles. In some embodiments, the particulate solid support used according to the invention may comprise a plurality of spherical beads such as coated beads, coated glass beads, glass beads, magnetic beads or coated magnetic beads.

In some embodiments, the volume of the cartridge well should be suitable to allow for fluid to freely flow across the surface of a solid support. In some embodiments, the cartridge wells may have a fluid volume with or without the solid support present of between 1 µl and 10 ml, such as between 10 µl and 10 ml, between 20 µl and 10 ml, between 50 µl and 10 ml, between 100 µl and 10 ml, between 150 µl and 10 ml, between 200 µl and 10 ml, between 250 µl and 10 ml, between 300 µl and 10 ml, between 500 µl and 10 ml, between 750 µl and 10 ml, or between 1 ml and 10 ml. For example, in some embodiments, the cartridge wells may be sized to provide additional space at the top of the well to prevent overflow of foam that may be formed during the bioprocessing. In addition, in some embodiments, the cartridge wells may include additional space to accommodate foaming during processing.

In some embodiments, the fluidics cartridge may be designed for multiple uses. In some embodiments, the cartridges may be disposable and/or are designed for a specific or limited number of uses, such as 20 uses or less, 15 uses or less, 10 uses or less, 9 uses or less, 7 uses or less, 5 uses or less, or 3 uses or less. In some embodiments, protocols are provided on the automated control system to provide for cleaning of the multiple use cartridges prior to re-use. Accordingly in some embodiments, the cartridges may be consumable products. In some embodiments, the fluidic cartridge may be single use cartridges.

IV. Methods

The device, card, and cartridge may be used as follows. In some embodiments, a device is provided into which a fluidics cartridge and a bioprocessing card may be inserted. A bioprocessing card may be loaded into the top drawer of the device. The bioprocessing card may be inserted into a card slot located in a plate located in the drawer. A sample may then be loaded into a preloaded fluidics cartridge with cartridge wells containing any suitable fluid including reagents and buffers. The fluidics cartridge may then be inserted into a cartridge slot located in a heating/cooling block located in the bottom drawer of the device. In some embodiments the fluidic cartridge may be inserted into slots in a separate cartridge tray which will be inserted into a heating/cooling block. In some embodiments, multiple cards and cartridges may be used and inserted into the device. After the card and cartridge are inserted into the device, a manifold may come in communication with the bioprocessing card, forming a seal with the card through the process fluid connectors on the card and thereby being capable of supplying atmospheric pressure, pressure, or vacuum to the card. A protocol may then be selected by the user using the GUI and the control panel. Once the protocol has been started, fluid may be transferred between different cartridge wells located on the cartridge.

The device operates by supplying vacuum to a process fluid connector located on the card. The process fluid connector opens a valve in communication with the process fluid connector by moving a membrane located in the valve. The open valve is in communication with a pipette tip which is in fluid communication with the contents of one cartridge well. Vacuum is then applied to one of the process fluid connectors in communication with a pump located on the card. The vacuum causes the membrane in the pump to move. The movement of the membrane causes fluid to be drawn from the cartridge well into the card through the pipette tip and the open valve. The fluid then passes into a process channel that runs between the valves located on the card. Once the fluid is drawn into the card, atmospheric pressure is applied through the process fluid connector located above the pump to deactivate the pump and thereby retain the fluid in the process channel. Atmospheric pressure is then applied to the process fluid connector located above the open valve to return the valve to its resting position. Pressure can then be applied to the same valve to prevent any fluid passing from the process channel into the now closed valve. Suction may then be applied to a valve in communication with another pipette tip which is in fluid communication with a second cartridge well to open the valve. The pump may then be activated by introducing pressure to the membrane in the pump through the control fluid connector. The application of pressure causes the membrane to be displaced, which thereby moves the fluid in the processing channel out of the channel through the open valve, through the pipette tip associated with the open valve and into a cartridge well in fluid communication with the pipette tip with open valve. Atmospheric pressure may be applied to the pump to deactivate the pump. Additionally, pressure may be applied to the open valve to close the valve. This process may be repeated as many times as necessary.

In some embodiments, methods of bioprocessing include: providing a fluidic cartridge, where the cartridge comprises at least one cartridge well containing a solid support, and providing a bioprocessing card having a processing channel in communication with a plurality of pipette tips, and pumping at least one process fluid through the processing channel between the plurality of pipette tips. In some embodiments, the pumping includes pumping one or more process fluids and/or a sample into a cartridge well and, in some embodiments, into contact with the solid support. The process fluids delivered to the solid support in the well may be any suitable solvent, solution or reagent for use in the desired bioprocess, including but not limited to liquid reagents used for chemical reactions, solvents or solutions used for washing, antibody solutions, buffer solutions, blocking buffer solutions and solutions containing fluorescent labeling reagents. The process fluids also may include samples that are to be processed such as proteins, nucleic acids and other macromolecules, cells, cell lysates, and any combination thereof. In some embodiments, the at least one processing fluid includes at least one blocking buffer. In some embodiments, the at least one processing fluid includes at least one antibody. In some embodiments, the at least one processing fluid includes at least one washing fluid.

In some embodiments, the pumping at least one process fluid through at least one of the pipettes and into at least one well includes pumping the at least one process fluid through a flow channel accessing the bottom portion of the well.

Further provided herein is a method of using the system, card, and cartridge provided herein. The pipette tips and individual valves of the card may be in communication, preferably fluid communication, with each other through the processing channel. The processing channel may further be in communication with the atmosphere through a valve. Pumps located on the card may be selected by the protocol and/or user to move fluid through the card. The pumps may be the same volume or different volumes with respect to one another. In some embodiments, the pumps may manipulate volumes of at least 10 µL, at least 20 µL, at least 50 µL, at least 100 µL, at least 150 µL, at least 200 µL, at least 300 µL.

A fluidics cartridge is aligned in the device with the card so that, in some embodiments, each pipette tip corresponds to one cartridge well. The fluidics cartridge may include a base from which cartridge wells may be fabricated or from which they may be supported. In some embodiments, either some or all of the openings of the cartridge wells may be sealed with a material, such as a film including but not limited to parafilm, aluminum foil, or any other suitable material for sealing the openings, prior to the protocol being run on the system. The material may either be removed prior to insertion of the cartridge into the device or may be broken by the pipette tips or some other mechanism within the device prior to the insertion of the pipette tips into their respective cartridge wells.

In some embodiments, a protocol may require the use of magnetic particles and a magnetic assembly to process a sample. The magnetic assembly of the device should interact with the cartridge wells so that the magnet forms a magnetic particle pellet. In some embodiments, the magnetic particle pellet should be located not too close to the bottom of a well so that it may be possible to aspirate off all of the supernatant, nor should the magnetic particle pellet be too located far away from the bottom which may interfere with resuspension of the magnetic particle pellet. In some embodiments, the magnetic assembly may be able to form bead pellets in multiple cartridge wells adjacent to the magnetic assembly.

Figure 1D:
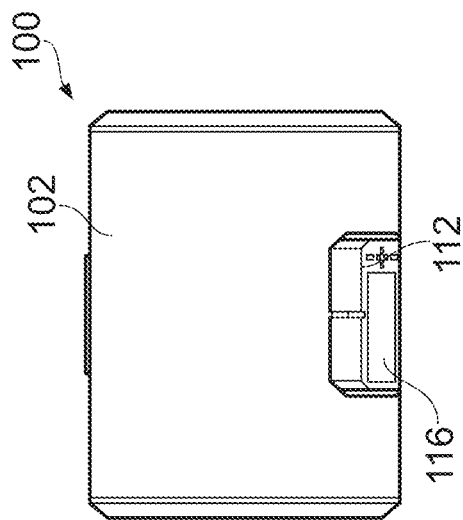
Figure 1A:
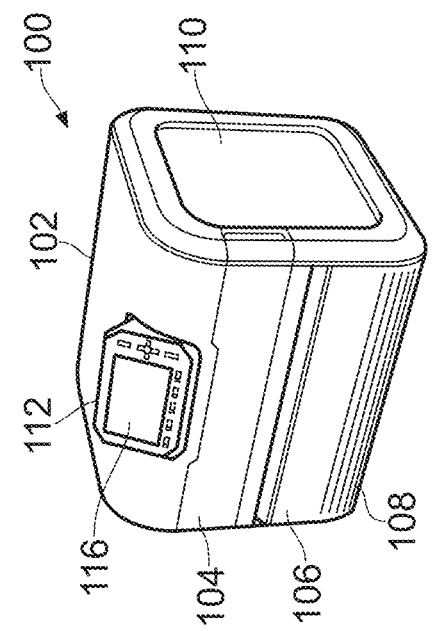
Figure 1C:
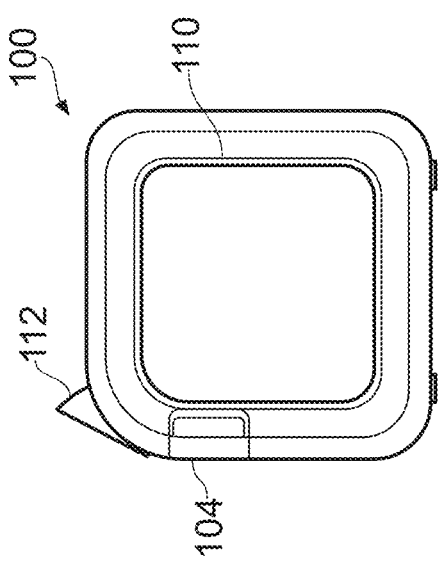

Referring now to FIGS. 1A-1G, various views of an embodiment of a device 100 is shown. FIG. 1A is a perspective view of an embodiment of a bioprocessing device 100. The bioprocessing device 100 may have a housing 102 that may include separate panels for the front, back, top and side panels 110. In some embodiments, the device 100 may have a single drawer or multiple drawers, for example, a top drawer 104 and a bottom drawer 106, as shown in FIG. 1A. The drawers 104, 106 may be pull-out drawers. In some embodiments, the doors may be flaps attached to the housing on hinges that swing open thereby giving access to the interior of the device 100. In some embodiments, vents 108 may be located along at least a portion of the housing 102 to provide heat dispersion from the components on the inside of the device 100. The vents 108 may be located on either the front, back, sides of the device or on at least one of these areas. The device 100 may further include a control panel 112 with which the user may interact with the device 100. The control panel 112 may include control buttons 114 and a graphical user interface (GUI) 116. FIG. 1B shows an embodiment of a device 100 as viewed from the front. Additionally, a top drawer 104 and a bottom drawer 106 can be seen. The top drawer 104 may be used to load a card for bioprocessing a sample and the bottom drawer 106 may be used to load samples and reagents used for bioprocessing. In some embodiments, a single drawer may be opened into which both the card and the cartridge may be loaded. The device 100 may also include vents 108 and a control panel 112 including control or selection buttons 114, directionality keys 118, and a GUI 116. FIG. 1C is a side view of an embodiment of a device 100 showing a side panel 110, a portion of the top drawer 104, and the control panel 112. FIG. 1D shows an embodiment of a device 100 as viewed from the top showing the housing 102, the control panel 112, and the GUI 116.

Figure 1F:
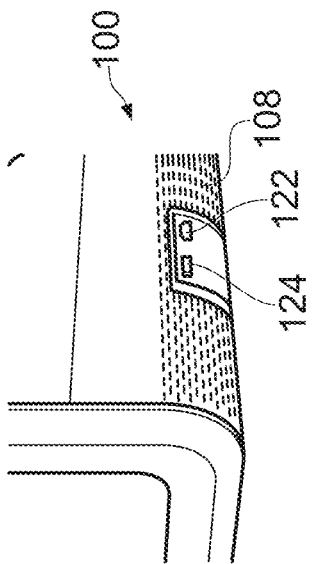
Figure 1H:
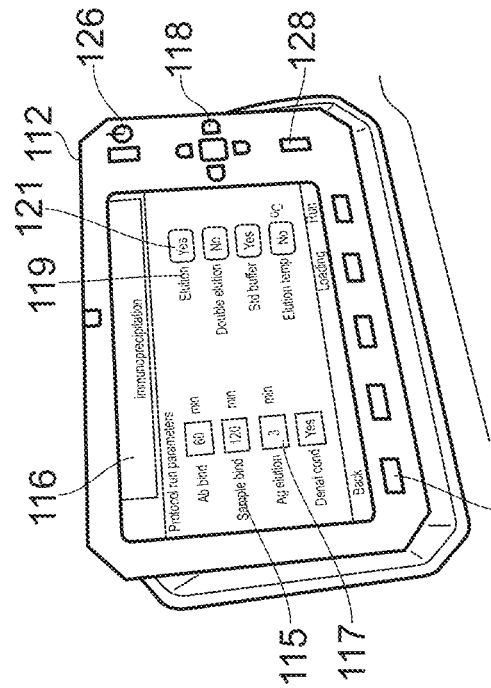
Figure 1E:
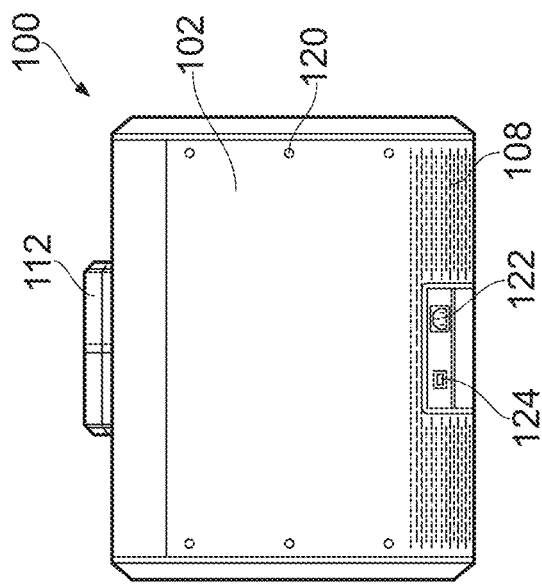

An embodiment of a back view of a device 100 is shown in FIG. 1E. The housing 102 of the device 100 may be attached to the device 100 with any suitable attachment mechanism including screws 120 or welding. As shown in FIG. 1E, vents 108 may be located along the back of the device 100. The top portion of the control panel 112 can also be seen. In some embodiments, a power switch 124 and a power supply connector 122 may be located at the back of the device 100 as shown in FIG. 1E. The power switch may be a switch, knob, button, or any other suitable mechanism for turning the system on and/or off. In some embodiments, the power switch 124 and the power supply connector 122 may be located in the middle of the device 100 or to one side of the back of the device 100 as shown in FIG. 1F. The power supply connector 122 and the power switch 124 may be surrounded by the vents 108 located in the back as shown in FIG. 1F, or may be located above or below the vents.

Figure 1G:
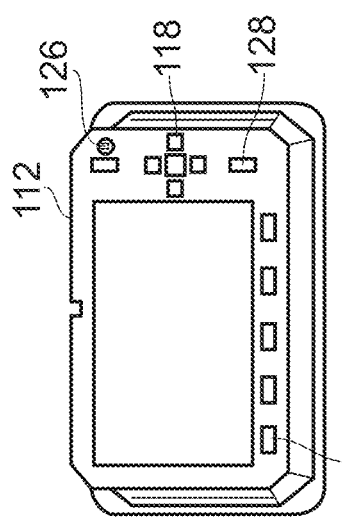

FIG. 1G illustrates an embodiment of a control panel 112 for use with the device 100. The control panel 112 may include selection or control buttons 114 and directionality keys 118 for selecting items or increasing or decreasing parameters. In some embodiments, the control panel 112 may be a touch panel. Additionally, the control panel 112 may be powered by a separate power button 126 on the control panel 112 or may be powered by the main power switch on the device 100. In some embodiments, the control panel 112 may include an interface 128 which may provide for upload of information onto the device or download of the process parameters used for any run directly onto a computer via a direct connection, such as an Ethernet port, a Personal Computer Memory Card International Association (PCMCIA) slot or an universal serial bus (USB) port 128. In some embodiments, the upload or download of information may be done using a wireless connection, a portable storage medium such as a flash drive or thumb drive, a writable CD-ROM, or DVD or the device may be connected to a network, such as a LAN or WAN or to an internet-based application. FIG. 1H shows a control panel 112 with a GUI 116, control or selection buttons 114, directionality keys 118, power switch 126, and interface 128. In FIG. 1H a GUI 116 for an immunoprecipitation protocol is shown. As shown, the steps 115 of the protocol and the time 117 required for each step 115 of the protocol may be shown. Additional steps 119 may also be shown with the user option 121 of selecting or deselecting the step for the protocol.

FIGS. 2A-2D show various embodiments of a device 200 with top 204 and bottom 206 drawers. FIG. 2A shows an embodiment of the device 200 with the top drawer 204 open. The device 200 includes a housing 202, top drawer 204, bottom drawer 206, vents 208, side panel 210, control panel 212 with control buttons 214 directionality keys 218, GUI 216, power switch 226, and interface 228. The top drawer 204 may include a plate 230 with at least one card slot 232 into which a bioprocessing card 550 for use with the device may be placed. In some embodiments, the plate 230 has at least one card slot 232, at least two card slots, at least three card slots, at least ten card slots, at least 12 card slots. At least one bioprocessing card 550 may then be positioned in one of the card slots 232 and may further be supported by the plate 230. In some embodiments, at least one card, at least two cards, at least five cards, at least ten cards, at least 12 cards may be loaded on the plate 230. FIG. 2B is a top view of a device 200 with top drawer 204 in an open position. The device 200 shown has a housing 202 and a control panel 212 and GUI 216. A top view of the plate 230 and card slots 232 may be seen in FIG. 2O. In some embodiments, the plate 230 may include notches 236 to lock the card 550 in place in a card slot 232. Slides 234 attached to the plate 230 facilitate drawing out and pushing in the drawer 204 after the card or cards are loaded onto the plate 230. In some embodiments, the slides may be attached at the sides of the plate or under the plate.

FIG. 2C shows a device 200 with the bottom drawer 206 open. The device 200 includes a housing 202, top drawer 204, bottom drawer 206, vents 208, side panel 210, control panel 212 with control buttons 214 directionality keys 218, GUI 216, power switch 226, and interface 228. In some embodiments, the bottom drawer 206 may include a heating/cooling block 238. In some embodiments, the heating/cooling block 238 may be directly attached to the bottom drawer 206. In some embodiments, a plate 242 may be attached to the bottom drawer 206 and the heating/cooling block 238 may be attached to the plate 242. FIG. 2D is a top view of the device 200 with bottom drawer 206 in an open position. The device 200 shown has a housing 202 and a control panel 212 and GUI 216. A top view of the drawer 206 including plate 242 and heating/cooling block 238 is shown in FIG. 2D with the plate may be attached to the bottom drawer 206 front. The heating/cooling block 238 may further include at least one cartridge slot 241, at least two cartridge slots, at least three cartridge slots, at least ten cartridge slots, at least 12 cartridge slots. The number of cartridge slots 241 of the heating/cooling block 238 may correspond to the number of cartridge slots 232 in the plate 230 of the top drawer 204. A fluidics cartridge 700 may be positioned in a cartridge slot 241 of the heating/cooling block 238, or they may be positioned in the slots of a cartridge tray which is positioned on top of the heating/cooling block.

Figure 3A:
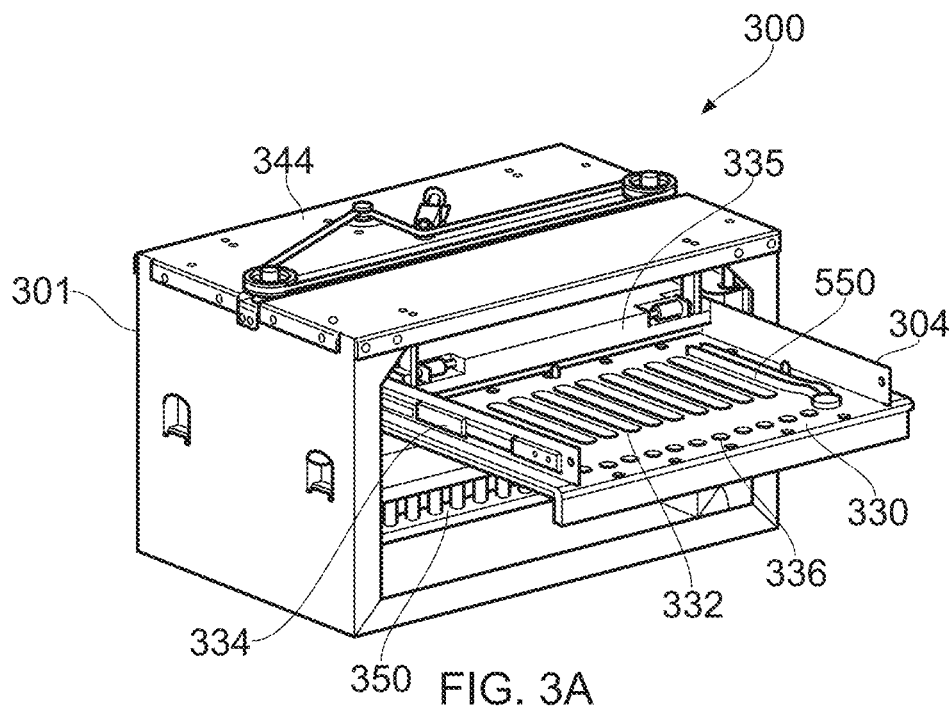
FIGS. 3A & 3B shows the drawers of the device with housing removed.
Figure 3B:
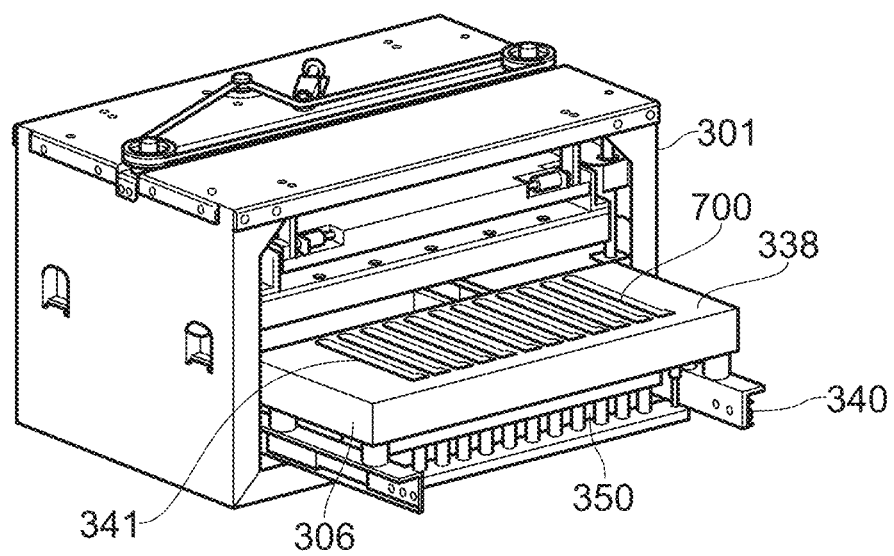

FIGS. 3A & 3B show an embodiment of a device 300 with the outer housing removed. A frame 301 is located under the housing. The top drawer 304 may be attached to the frame 301 via slides 334 that may be located at the sides or bottom surface of the drawer 304. Enough card slots 332 may be located on the plate 330 of the drawer 304 to hold at least one card 550, at least two cards, at least five cards, at least ten cards, at least 12 cards. The card 550 may be locked into place on the plate 330 by inserting the notch on the card 550 with a card notch 336 on the plate. FIG. 3A further shows a manifold 335 located in the frame 301 that comes in contact with the top surface of the card 550 when the top drawer 304 has been retracted back into the frame, as shown in FIG. 3B. FIG. 3B shows the bottom drawer 306 of the device 300 advanced out of the frame 301. The heating/cooling block 338 is directly attached to the frame 301 using slides 340 positioned under the heating/cooling block 338. Enough cartridge slots 341 may be located on the heating/cooling block 338 to hold at least one fluidics cartridge 700, at least two cartridges, at least five cartridges, at least ten cartridges, at least twelve cartridges. The number of fluid cartridges positioned in the heating/cooling block 338 may equal the number of cards 550 positioned in the top drawer 304. A height adjustment system 344 may control movement of the plate 330 of the top drawer 304 relative to the heating/cooling block 338 or movement of the heating/cooling block 338 with respect to the top plate 330. The bottom drawer with the heating/cooling block may be moved in and out within the frame in a stepwise fashion. A magnetic assembly 350 is localized underneath the heating/cooling block 338.

Figure 4:
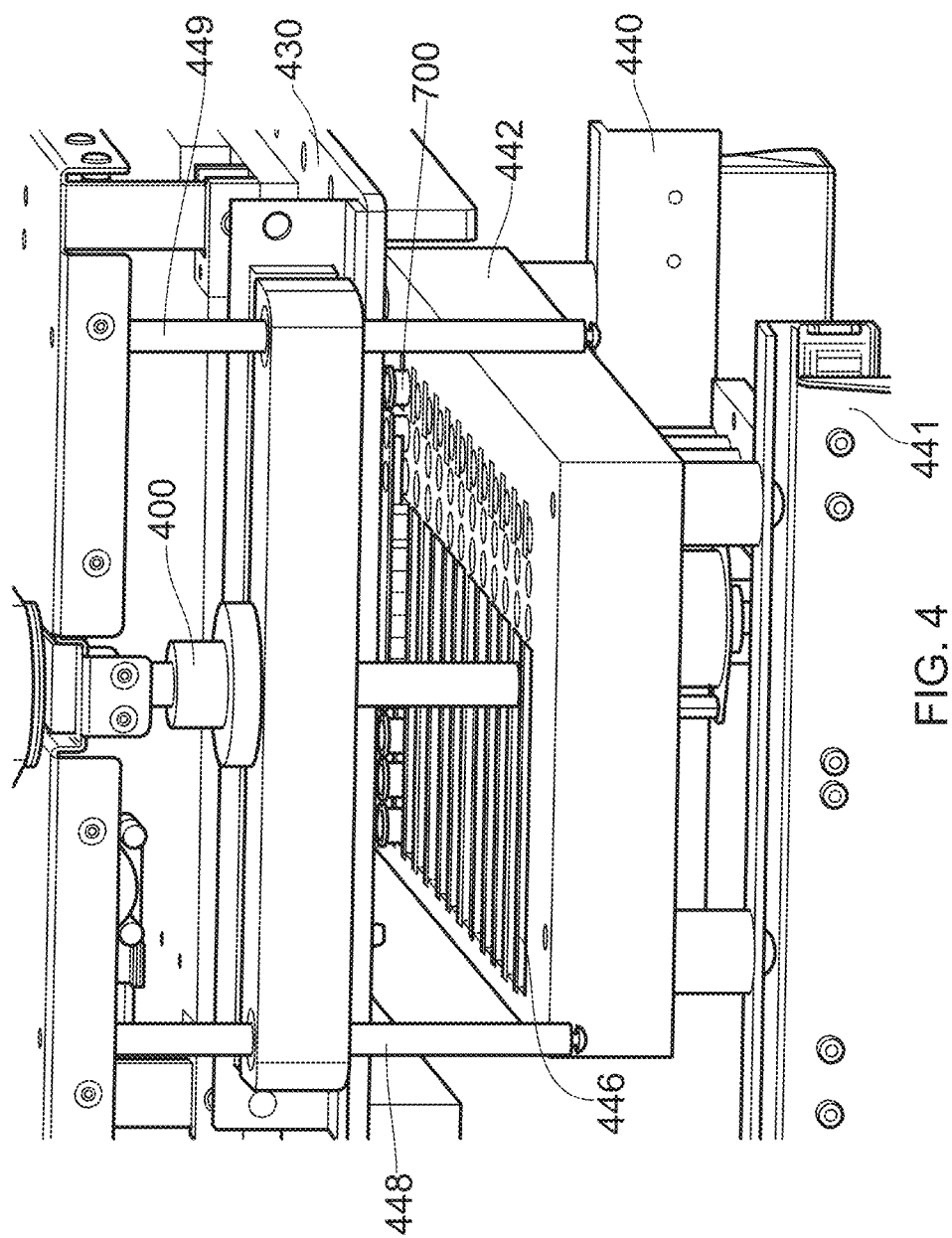
FIG. 4 is a side view of the device with the housing removed.

FIG. 4 shows a side view of the card plate 430 and the heating/cooling block 438 without the frame of an embodiment of a device. The heating/cooling block 438 can be pulled out of frame using slides 440, 441. The heating/cooling block 438 is aligned with the plate 430 which can also be pulled out of the frame using slides 434. The slides 434 may be attached to a support bar 447 which may raise and lower the card plate 430 following support guides 448, 449. A connector 450 attached to the support bar may then raise and lower the card plate 430. In some embodiments, the heating/cooling block may be raised and lower relative to the card plate, and in some embodiments it may be moved in and out within the frame relative to the position of the card.

Referring now to FIGS. 5A-5C, FIGS. 5A-5C show various embodiments of a card 550 for use with a device described herein. FIG. 5A is a view of an embodiment of a card 550 as viewed from the top. The card 550 includes a body 551, control fluid connectors 552 located along the length of the body 551, and a foot 554 and notch 556 for aligning and locking the card 550 in place on the card plate of the device. In some embodiments, alignment holes 558, 559 may be located on the body 551 of the card 550 for aligning the parts of a card 550. FIG. 5B is a view of the bottom of an embodiment of a card 551. At least one pipette tip 560 may be located along the length of the body 551 of the card 550. In some embodiments the pipette tip lengths may vary with respect to each other. In some embodiments, the pipette tip lengths may be the same length. The pipette tips may be spaced uniformly along the length of the body 551 of the card 550, or, alternatively the distance between pipette tips may be varied. In some embodiments, supports 561 extend radially from the base of the pipette tip 560 to provide extra support between the pipette tip and the base of the card. In addition to the pipette tips 560, pumps 562, 563, 564 may be integrated with the card 550. A processing channel 565 transports fluid between the different individual pipette tips 560 along the length of the card 550. FIG. 5C is a side view of and embodiment of a card 550 including the body 551, control fluid connectors 552, foot 554, notch 556, pumps 562, 563, 564, pipette tips 560 and pipette tip supports 561. FIG. 5D shows a side view of an alternate embodiment of the card 550 where the pipette tips 560 are all the same length.

FIG. 6A shows a top view of an embodiment of a card 650 showing the individual valves 666 in communication, preferably fluid communication, with the pipette tips and control fluid connectors. Pumps 662, 663, 664 and their respective membranes can be seen as well. FIG. 6B is a cross-sectional view of the card 650, with foot 654, notch 650, pumps 662, 663, 664, shown in FIG. 6A along the line B-B, illustrating the hollow interior of the control fluid connectors 652 along the body 651 of the card 650. The pipette tips 660 are offset with respect to the control fluid connectors 652. A membrane 668 may be positioned along the length of the card 650 or, alternatively, individual membranes may be positioned at the positions of the individual valves 666. In some embodiments, the membrane or membranes is a silicone membrane or any other suitable material. FIG. 6C is a cross-sectional view of a card 650, foot 654, notch 656, and pumps 662, 663, 664 shown in FIG. 6A along the line C-C. FIG. 6C shows the hollow interior of the pipette tips 660 along the body 651 of the card 650. A membrane 668 may be positioned along the length of the card 650.

FIG. 6D is a close-up view of one of the individual valves 666 shown in FIG. 6A. FIG. 6D illustrates the off-set nature of the pipette tip 660 and the control fluid connector 652 with respect to each other. The pipette tip 660 and control fluid connector 652 are offset to facilitate the opening and closing of the valve or membrane located between the pipette tip 660 and the control fluid connector 652. Further shown is the processing channel 655 that runs between the individual valves 666 on the card 650 and by which fluid is transferred between pipette tips 660. Openings 657 located at the along the processing channel 655 in fluid communication with the valves 666 transfers materials and/or fluids between the different valves 666. An alignment hole 658 located on the card 650 may be present on the card 650 to align the parts of the card, where there are more than one part, and the membrane or membranes.

FIG. 6E is a close up view of the pumps 662, 663, 664 of the card 650 shown in FIG. 6A as viewed from the top. Control fluid connectors 652 located above the pumps 662, 663, 664 facilitate the activation and/or deactivation of the pumps 662, 663, 664. A processing channel 665 is located between the pumps 662, 663, 664 and extends to the individual valves located down the length of the card 650. The processing channel 665 may control the movement of a volume of fluid pumped through each of the individual valves. FIG. 6F shows a close-up side view of the pumps 662, 663, 664 of the card 650 as shown in FIG. 6B. FIG. 5F shows the pumps 662, 663, 664 and the membranes 667, 669, 671 of the pumps 662, 663, 664, respectively. Each pump 662, 663, 664 is in communication with a control fluid connector 652 each of which has an opening 672 and a center 670 through which atmospheric pressure, suction and/or pressure can be supplied to facilitate the actuation or deactivation of the pumps 662, 663, 664. Each pump 662, 663, 664 has a connector 653, 655, 657 which connects the pumps 662, 663, 664 to the processing channel 665. Each pump also has a membrane 667, 669, 671 that expands and contract during pump operation to draw in or expel fluid and/or materials from the card.

FIG. 6G is a cross-sectional view through one of the individual valves 666 along the line G-G, as shown in FIG. 6A. FIG. 6G shows a cross-sectional view through one of the valves 666 including the pipette tip 660 and the control fluid connector 652, showing the offset nature of the pipette tip 660 and the control fluid connector 652. In some embodiments, the card 650 may be constructed as a single piece. In some embodiments, the card 650 may be made from two pieces 675, 677 where the control fluid connectors 652 are located on one piece 675 and the pipette tips 660 are located on the second piece 677. A membrane 668 or membranes may be located between the two pieces 675, 677. An edge 674 located along the length of one piece 675 may interact with a manifold for supplying suction and/or pressure to the card 650. The pipette tip 660 extends from the bottom of the card 650 and in some embodiments supports 651 extending radially from the base of the pipette tip 660 may offer support between the base of the card 650 and the pipette tip 660. In some embodiments, the diameter of the pipette tip 660 remains constant along the length of the pipette tip or alternatively, the diameter of the pipette tip 660 may vary along the length of the pipette tip 660. The interior diameter of the pipette tip 660 which forms the center portion 676 of the pipette tip 660 may remain constant along the length of the pipette tip or may vary along the length of the pipette tip 660. In some embodiments, the end 679 of the pipette tip 660 may taper. An opening 678 located at the end 679 of the pipette tip 660 allows for communication, preferably fluid communication, with fluid or materials. The foot 654 of the card 650 is also shown.

Figure 7A:
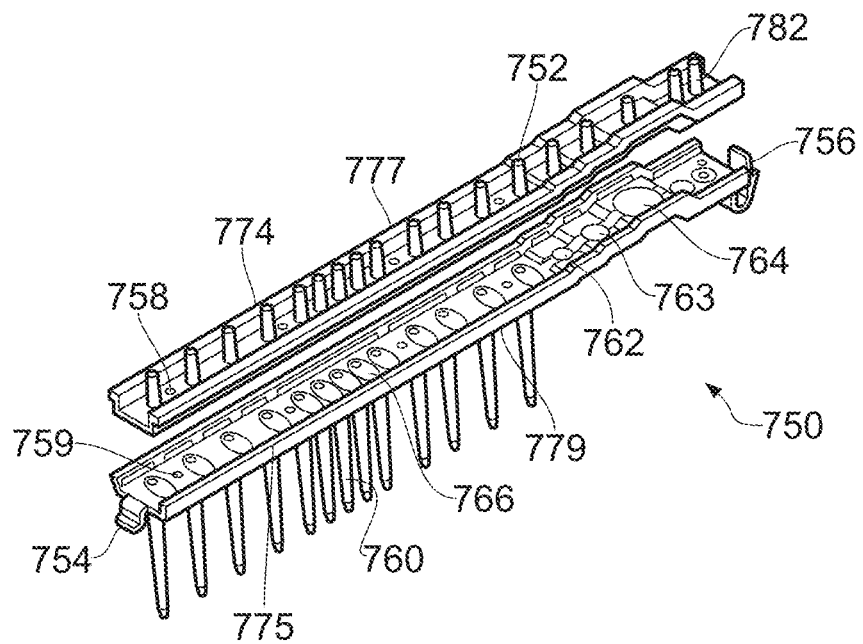
FIGS. 7A & 7B illustrate an embodiment of a card.
Figure 7B:
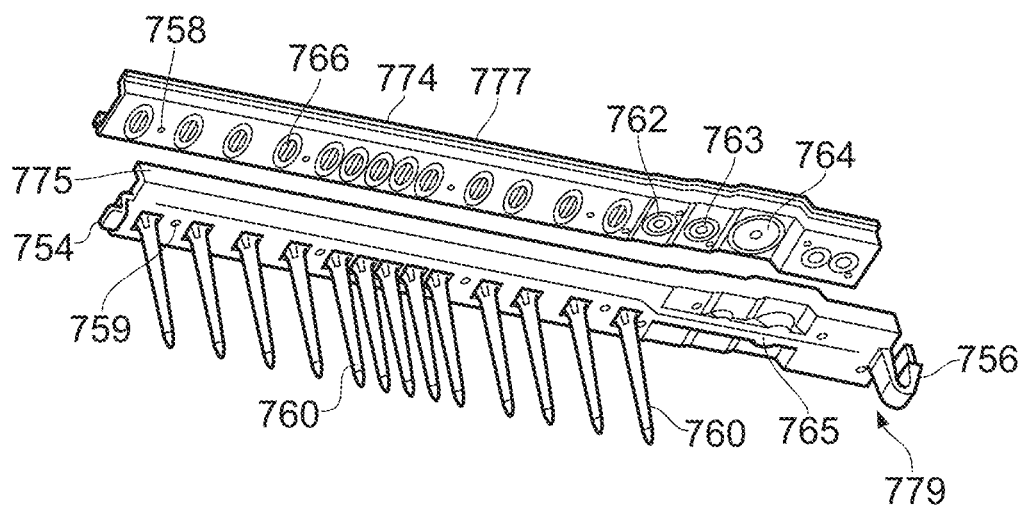

Referring to FIGS. 7A & 7B show a card 750 having a foot 754 and a notch 756, constructed from two pieces 775, 777, aligned with each other for assembly. In some embodiments, the length of the first piece 775 and the second piece 779 are substantially the same length or the lengths may vary with respect to each other. The edge 774 of one piece 775 fits together with the edge 775 of the second piece 779. The control fluid connectors 752 are aligned with the individual valves 766 and the pipette tips 760. Additionally, control fluid connectors 752 may be aligned with the pumps 762, 763, 764. In some embodiments, control fluid connectors 782 may be located on the card 750 that may be used to equilibrate the pressure inside the card. The supply connector 765 may be seen on the bottom surface of the card 750, as shown in FIG. 7B. In some embodiments, a membrane strip may be placed between the first 775 and second 777 piece or individual membranes may be placed in each individual valve 766 and pumps 762, 763, 764.

In some embodiments, the card may be a constructed as a single piece. In some embodiments, the card may be constructed as at least two pieces that are molded separately and then assembled together. Where the card is made from two pieces, the pieces may be assembled together using ultrasonic welding, welding, glue, adhesives, thermal sealing or thermal adhesives, any combination thereof, or any other suitable mechanism for assembling the two pieces together. Where ultrasonic welding is used to assemble the card, the ultrasonic welding may be performed by an ultrasonic welder (such as Herrmann Computer Numberic Controlled (CNC) Ultrasonic Welding System, Serial Number SM9132/08).

The card or card pieces may be made from plastic, polypropylene, a nucleated polymer, any combination thereof, or any other suitable material for injection molding. In some embodiments, the card or card pieces may be a polypropylene homopolymer (for example, Metocene X50109 Polypropylene Homopolymer).

Figure 8A:
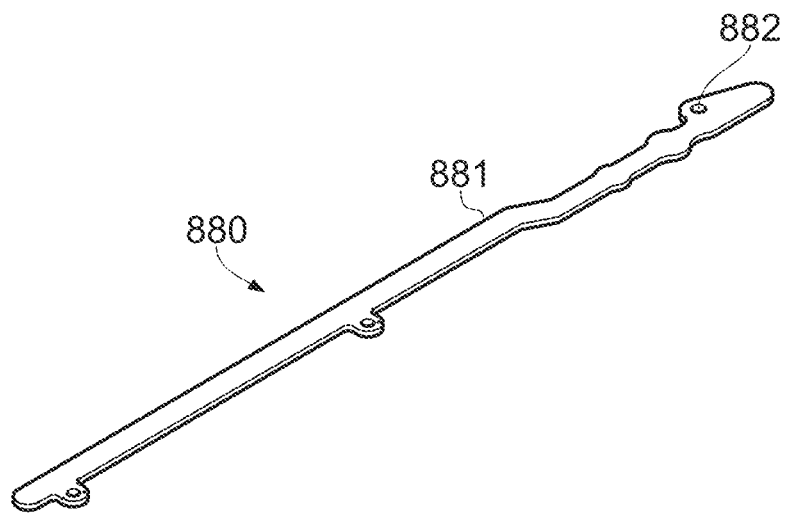
FIGS. 8A & 8B illustrate an embodiment of a sealing foil for use with the card.
Figure 8B:
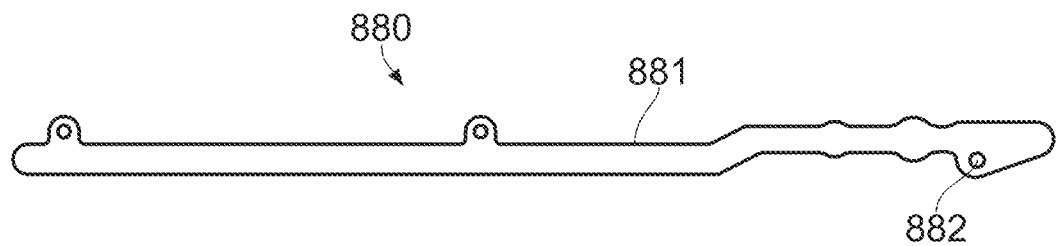

FIGS. 8A & 8B show and embodiment of a sealing foil 880 used to seal the card. The sealing foil 880 has a length that may or may not be substantially the same length as the card. In some embodiments, the length of the sealing foil 880 may be a predetermined length based on the length of the card. In some embodiments, the sealing foil 880 may differ in length from the card and may be sized to fit the card either before or after sealing the card. The sealing foil 880 may seal the card so that the seal is air tight or substantially air tight. In some embodiments, the sealing foil 880 may further include alignment holes 882 for aligning the sealing foil 880 with the card. After the card has been assembled, a sealing foil may be attached to the assembled card.

In some embodiments, the sealing foil may be attached to the card using glue, adhesives, heat sealing, or any other suitable mechanism for attaching the sealing foil to the card. In some embodiments, the sealing foil may be attached to the card using heat sealing. The sealing material may first be placed in position over the card. Heat is then applied, preferably evenly, over the card for several seconds to weld the sealing foil to the card. The sealing foil may be attached to the bottom of the card. In some embodiments, the sealing foil, the card, or both the sealing foil and the card may be equipped with markers or alignment features to aid in the correct placement of the sealing foil with respect to the card. A thermal press (such as C-Frame Precision Thermal Press C-25MM, Serial number C25MM08122901 from Thermal Press International Inc.) may be used to attach the foil to the card. In some embodiments, the sealing foil may be, for example purposes only, REMP Peircable Thermo-Seal, Removable Thermo-Seal, Extra-Durable Removable Thermo-Seal, Clear Thermo-Seal, any combination thereof, or any other suitable sealing foil.

FIGS. 9A-9C show various view of an embodiment of a membrane 968 that may be used with the card. The membrane 968 may have a length 969 that may or may not be predetermined prior to assembling the card. FIG. 9A is a perspective view of an embodiment of a membrane 968 having a length 969 and at least one alignment hole 958 for aligning the membrane with the card. The membrane 968 may either have a predetermined shape to fit the contours of the card as shown in FIG. 9A or may conform to the contours of the card after being inserted into the card. In some embodiments, the membrane 968 may have a predetermined length 969 and/or width substantially similar to the length of the card. Alternatively the membrane 968 may be modified prior to or after assembly to the desired shape to fit the card. FIG. 9B is a side view of a membrane 968 having a length 969 and predetermined shape. FIG. 9C is a top view of an embodiment of a membrane 968 having a length, predetermined shape, and more than one alignment holes 958.

In some embodiments, a single membrane may span the length of the card or individual membranes may be positioned in the card over the individual valves and/or pumps. In some embodiments, the membrane may be a silicone membrane or any other suitable material. Where a two piece card is used, the silicone membrane may be placed between the top and bottom parts of the card. In some embodiments, the membrane, the card, or both the membrane and the card may include fixtures, markers, alignments guides to aid in the correct placement of the silicone membrane between the card pieces before the card it welded together.

In some embodiments, after the card has been assembled, the functionality of the card may be verified and/or assessed.

FIGS. 10A-10C show various views of an embodiment of a fluidics cartridge 1090. FIG. 10A shows a perspective view of an embodiment of the fluidics cartridge 1090. The fluidics cartridge 1090 may have at least one, at least two, at least five, at least 10, at least twelve, or more than twelve cartridge wells 1092 for containing and confining a fluid and/or materials, such as reagent, waste, and/or sample wells. The number of cartridge wells 1092 may or may not be the same as the number of pipette tips located on a card for manipulating fluids in the fluidics cartridge 1090. Each cartridge well 1092 has an opening 1094 in communication, preferably fluid communication, with the pipette tips of the card. In some embodiments, the fluidics cartridge 1090 may include features 1091 for aligning, positioning, and/or retaining the fluidics cartridge 1090 with respect to the heating/cooling block. The feature may be a notch, groove, physical structure, or any other suitable feature for aligning, positioning, and/or retaining the fluidics cartridge 1090 with respect to the heating/ cooling block of the device. In some embodiments, the fluidics cartridge 1090 may be constructed with a predetermined number of cartridge wells 1092, as shown in FIG. 10A. In some embodiments, the cartridge wells 1092 of the cartridge 1090 may or may be of the same shape and/or size relative to the other cartridge wells 1092 on the same cartridge 1090. In some embodiments, the cartridge wells 1092 may all be the same shape, size, and/or length relative to each other. FIG. 10B shows an embodiment of a fluidics cartridge 1090 as viewed from the top. The bottoms 1095, 1096, 1097 of the cartridge wells may be seen through the openings 1094 of the individual wells. The bottom may be any suitable configuration to ensure that the complete amount of fluid may be aspirated into the card when necessary. FIG. 10C shows a side view of one embodiment of a fluidics cartridge 1090 with cartridge wells 1092, bottoms 1095, and features for aligning, positioning, and/or retaining the fluidics cartridge 1090 with respect to the heating/cooling block in the device. The fluidics cartridge may be constructed as a single piece, at least two pieces, or more than two pieces. The cartridge or cartridge pieces may be made from any suitable plastic, polypropylene, nucleated polymer, any combination thereof, or any other suitable material for injection molding. In some embodiments, the cartridge or cartridge pieces may be a polypropylene homopolymer (for example, Metocene X50109 Polypropylene Homopolymer).

In some embodiments, the cartridge 1090 may be constructed so that some of the cartridge wells 1092 are prefabricated with the cartridge 1090 while other positions are constructed so that tubes can be added to the cartridge 1090. FIGS. 10D & 10E show an embodiment of a fluidics cartridge 1090 with some wells 1092 prefabricated and some openings 1093 fabricated into the card into which vials, or tubes may then be inserted. FIGS. 10D & 10E further show an embodiment of a feature 1091 for aligning, positioning, and/or fixing the fluidics cartridge 1090 into the device. FIG. 10F shows the an embodiment of a fluidics cartridge 1090 having some prefabricated wells 1092 and openings 1093 into which tubes 1098 have been inserted prior to use. The tops 1099 of the tubes 1098 prevent the tubes 1098 from falling through the openings 1093.

Figure 20:
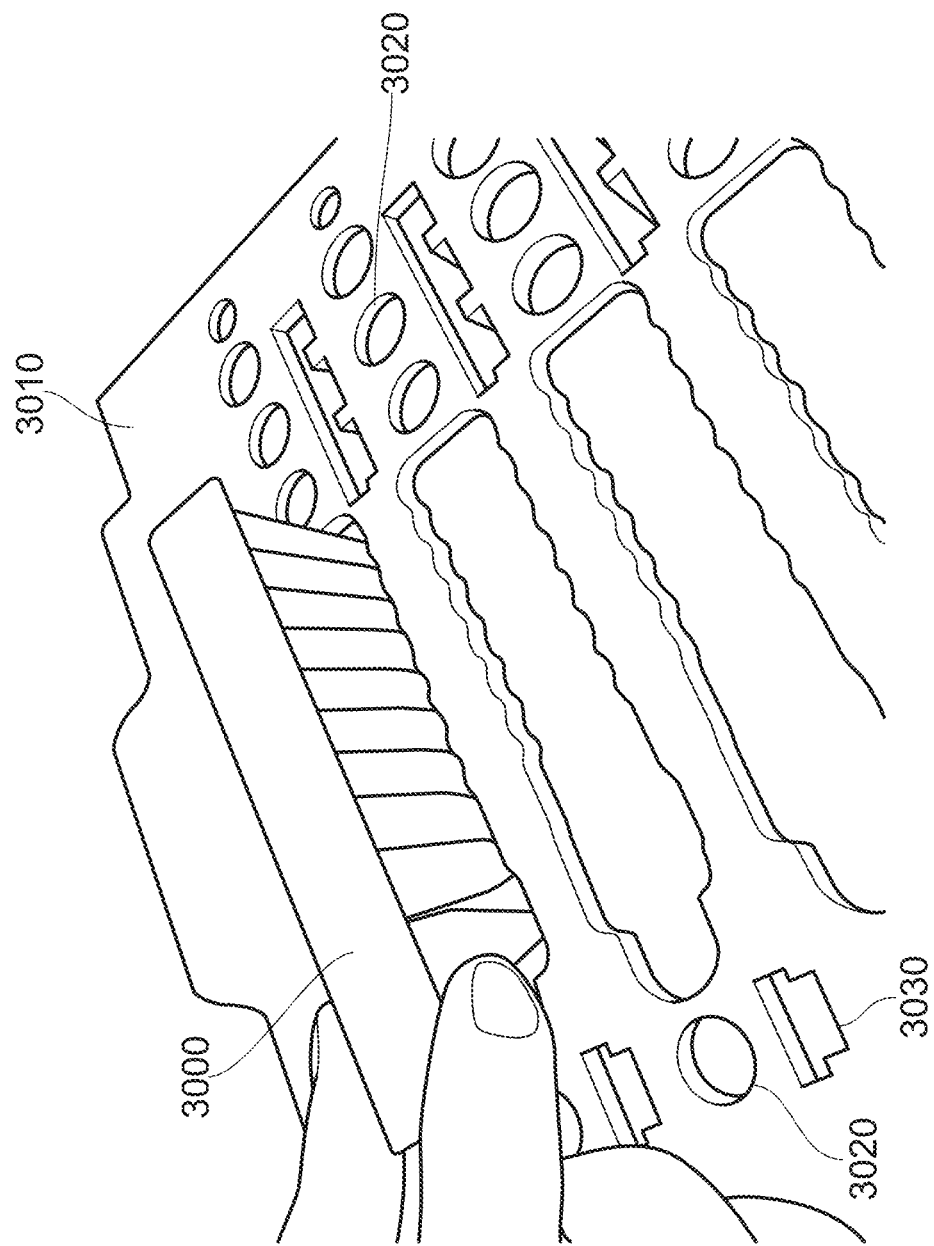
FIG. 20 shows how the fluidics cartridge fits into a cartridge tray

FIG. 20 illustrates how the cartridge 3000 can be slotted into a cartridge tray 3010 where there are openings 3020 into which tubes can be inserted. There are specific holes made in the tray 3030 where the lid of the micro-centrifuge tubes may be fastened during operation.

Figure 21:
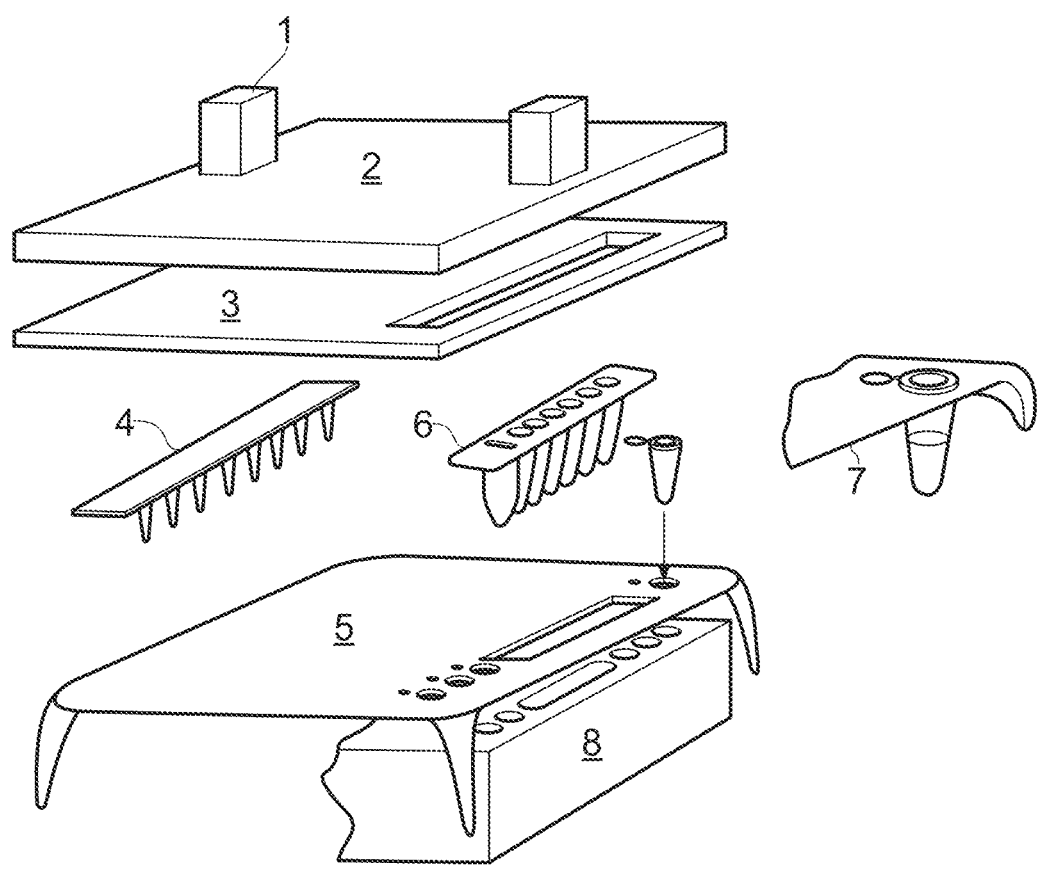
FIG. 21 shows how a card tray, a cartridge and a card try can be deployed together

FIG. 21 shows how a card tray, a cartridge and a card try can be deployed together, and is to be interpreted in conjunction with FIG. 20.

Figure 11:
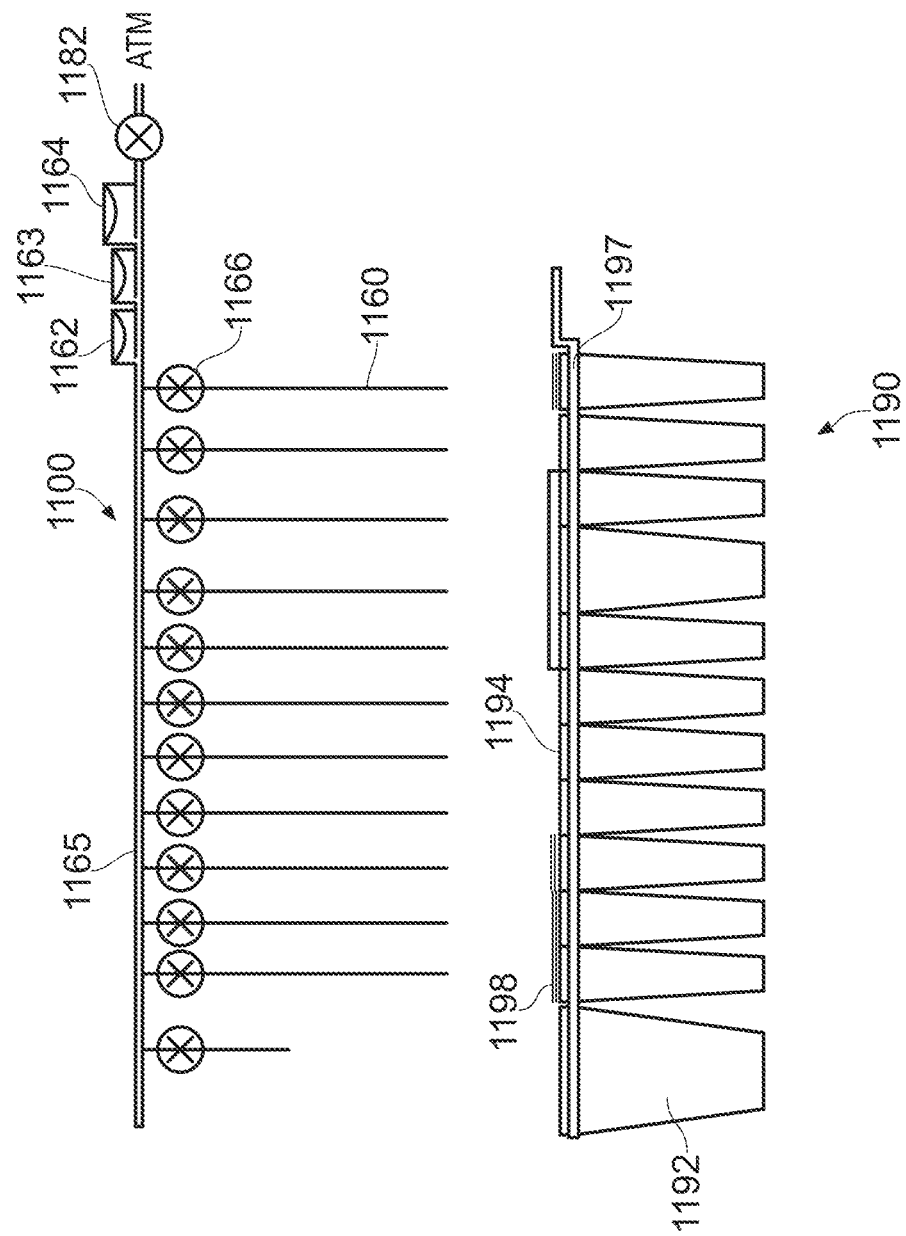
FIG. 11 shows an embodiment of a card and a fluidics cartridge.

FIG. 11 illustrates the how a card 1100 interacts with a fluidics cartridge 1190. The pipette tips 1160 and individual valves 1166 of the card 1100 may be in communication, preferably fluid communication, with each other through the processing channel 1165. The processing channel 1165 may further be in communication with the atmosphere through a valve 1182. Pumps 1162, 1163, 1164 located on the card may be selected by the protocol and/or user to move fluid through the card. The pumps may be the same volume or different volumes with respect to one another. In some embodiments, the pumps may manipulate volumes of at least 10 μL, at least 20 μL, at least 50 μL, at least 100 μL, at least 150 μL, at least 200 μL, at least 300 μL.

A fluidics cartridge 1190 is aligned in the device with the card 1100 so that, in some embodiments, each pipette tip 1160 corresponds to one cartridge well 1192. The fluidics cartridge 1190 may include a base 1197 from which cartridge wells 1192 may be fabricated or from which they may be supported.

In some embodiments, either some or all of the openings 1194 of the cartridge wells 1192 may be sealed with a material 1198 prior to the protocol being run on the system. The material 1198 may either be removed prior to insertion of the cartridge 1190 into the device or may be broken by the pipette tips 1160 or some other mechanism within the device prior to the insertion of the pipette tips 1160 into their respective cartridge wells 1192.

Figure 12A:
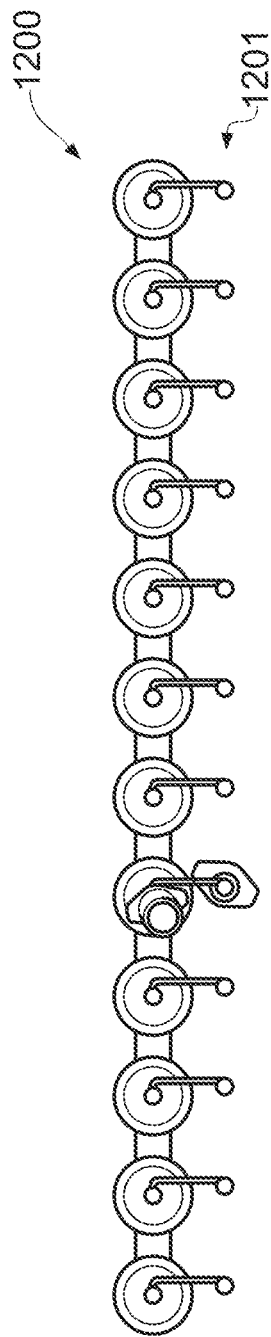
FIGS. 12A & 12B show various views of an embodiment of a manifold for use with the device.
Figure 12B:
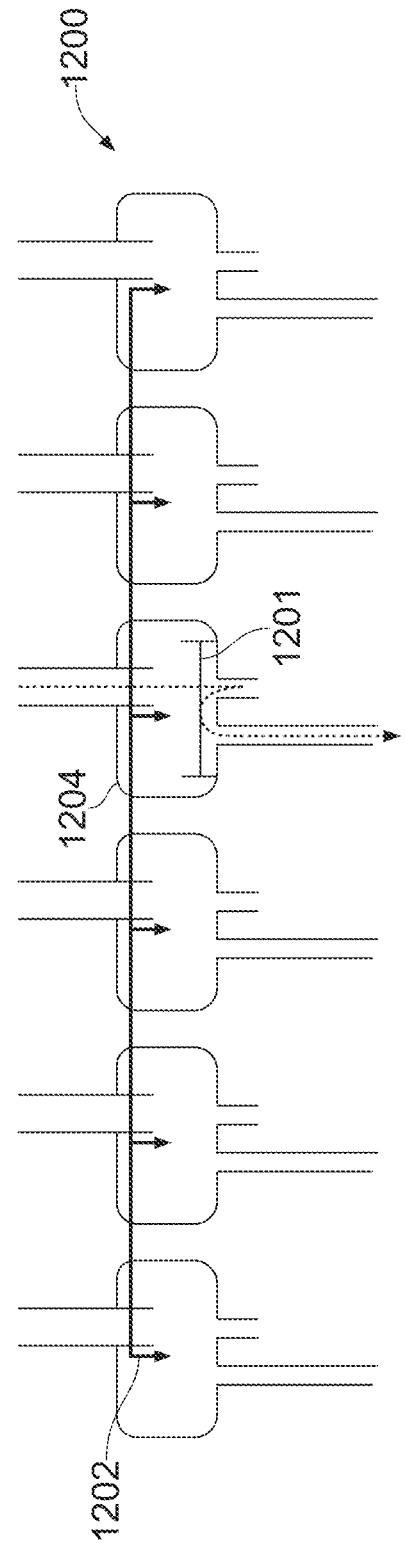
Figure 12C:
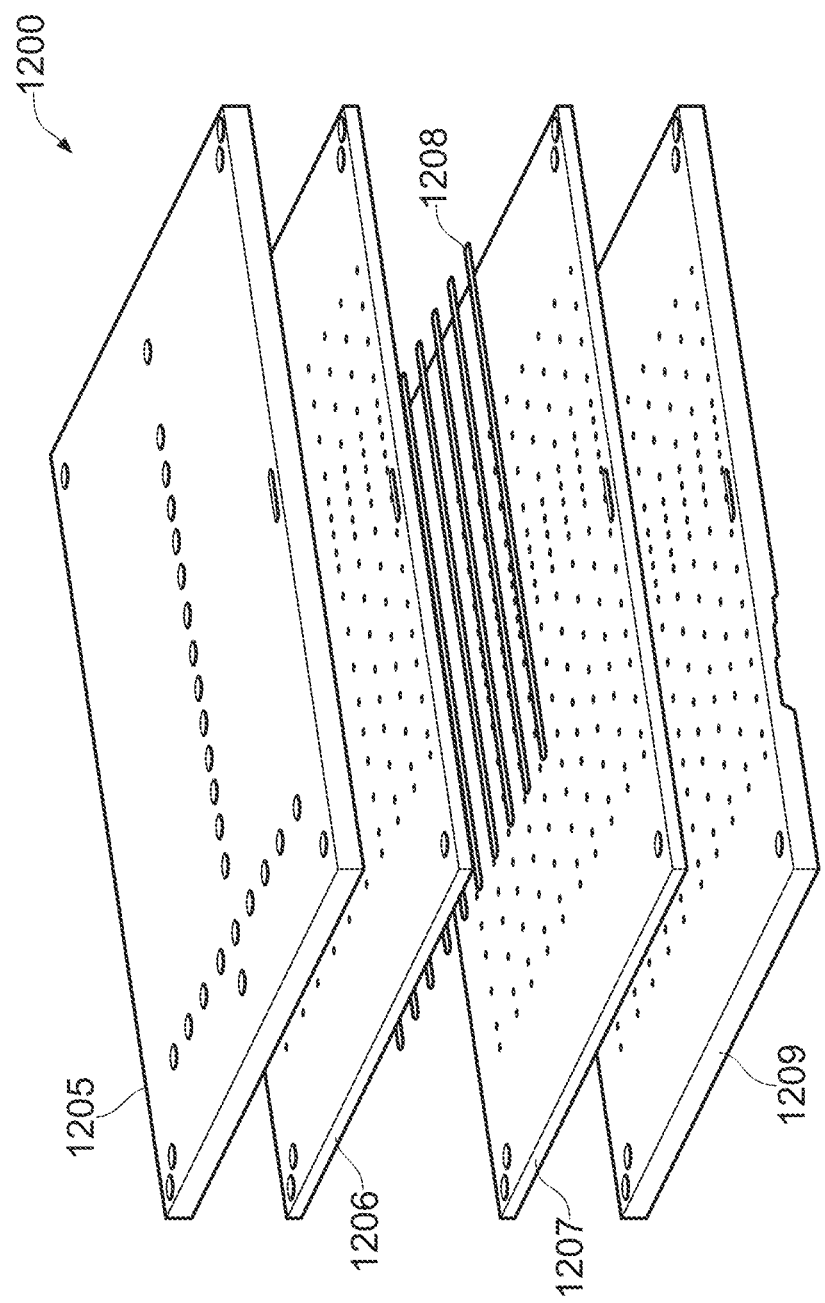
FIGS. 12C & 12D show various embodiments of a manifold.

FIGS. 12A-12C show various embodiments of a manifold 1200 for use with the device, which is in communication with the control fluid connectors on the card. The manifold 1200 may be used to supply vacuum and/or pressure to the card. FIGS. 12A & 12B show one embodiment of a manifold. In some embodiments, the manifold 1200 may supply atmospheric pressure, vacuum and/or pressure to the locations where a card is located or may supply atmospheric pressure, vacuum and/or pressure regardless if a card is located in a position under the manifold. In some embodiments the manifold 1200 may supply pressure and/or suction to locations on the manifold 1200 corresponding to positions where a card is located. For example, the manifold 1200 may be mechanically sealed by a barrier that is displaced when a card is in communication with the manifold. In some embodiments, the system can be programmed so that portions of the manifold under which cards are located can be activated.

FIG. 12A shows a manifold 1200 as viewed from the top where individual valves/diaphragms 1201 control which locations receive pressure and/or suction. In some embodiments, there may be one single silicone membrane per card as opposed to individual diaphragms 1201 for each valve/pump. FIG. 12B shows a portion of the manifold 1200 shown in FIG. 12A as viewed from the side. As indicated by the dashed line in FIG. 12B, air pressure and/or vacuum may be applied to control the state of the valves/pumps in the card. Air pressure to control each individual card may be introduced to the manifold as indicated by the solid line 1203. The air pressure may be applied to individual diaphragms 1201 in communication with the control fluid connectors on the card. Each valve 1204 in the manifold 1200 in communication with a control fluid connector may further include a diaphragm 1201 which may be used to override the control fluid which is represented by the dashed line. In some embodiments, the manifold may further include air flow restrictors, such as tubing with narrow inner diameters or any other suitable air flow restrictor.

In some embodiments, the manifold 1200 may be constructed as shown in FIG. 12C. In such an embodiment, valves and pumps to supply the individual valves on the card would be mounted on the top layer 1205 of the manifold 1200. The second 1206 and third 1207 layer of the manifold 1200 may house the valves for supplying vacuum/pressure to the card by the manifold. The manifold 1200 may include a single silicone membrane strip 1208 per card located in between the second 1206 and third 1207 layers instead of individual diaphragms 1201 per valve/pump 1204 on cards (as shown in FIG. 12B). The bottom layer 1209 of the manifold 1209 may then interact with the cards.

Figure 12D:
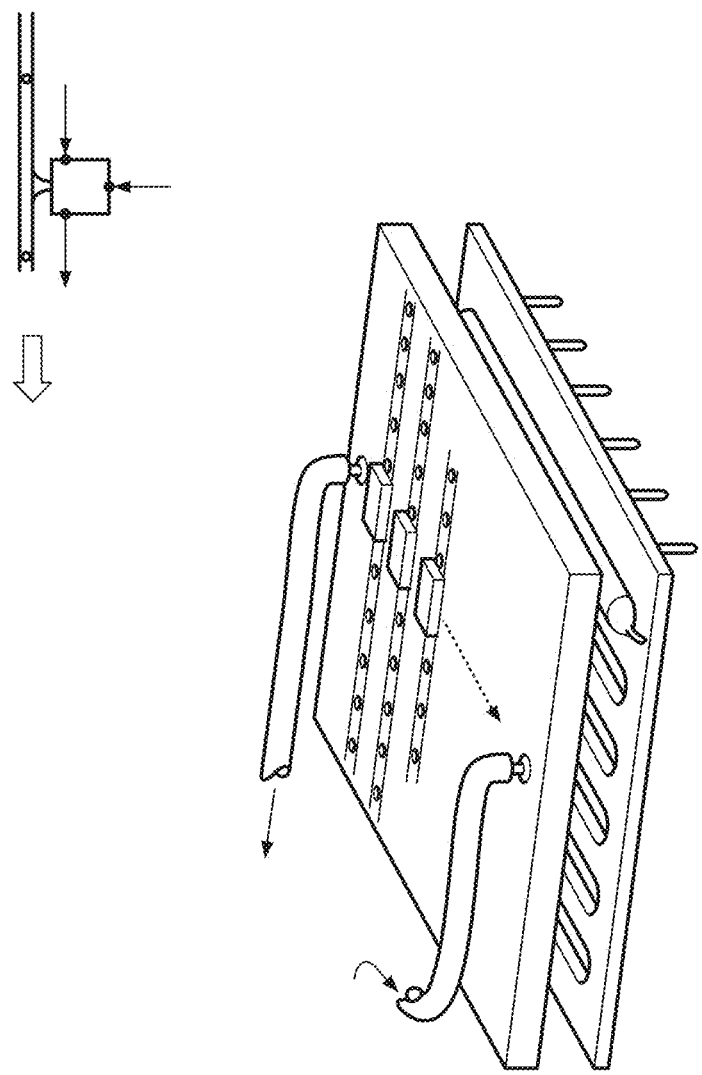

Yet another embodiment of a manifold is shown in FIG. 12D. Vacuum and/or pressure may be supplied to the manifold using different connectors or may be supplied using the same connector. In some embodiments, the suction and/or pressure may be supplied by a house source or may be supplied by an external source. Valves, which may or may not be electronic controlled valves are located along the manifold and positioned above an area in communication with a card. The electronic valve is in further communication with an air channel in the manifold. The air channel may have valves to supply air, pressure, and/or vacuum to the control valves on the card. Vacuum may be applied to suck liquid and/or materials into the card through an open valve. The suction then switches to atmospheric pressure to stop suction. Pressure may then be applied to expel any liquid in the card through an open valve.

In some embodiments, magnetic particles may be used with the device and/or cartridge. FIGS. 13A & 13B show a fluidics cartridge 1390 and magnet assembly 1384 for interacting with the fluidics cartridge 1390. In some embodiments, magnetic beads 1386 may be present in at least one of the cartridge wells 1392 of the fluidics well 1390. The magnetic beads 1386 may be used to separate a component from a fluid in the cartridge well. When a magnet assembly 1384 comes in communication with a cartridge well 1392, any beads or any other suitable magnetic particle may be attracted to the walls of the cartridge well 1392 as shown in FIG. 13A. The magnetic assembly may be located away from the fluidics cartridge and then moved into proximity with the fluidics cartridge by moving the magnetic assembly up to the fluidics cartridge or next to the fluidics cartridge. In some embodiments, the magnetic assembly is constantly in contact with the fluidic cartridge and is turned on and off as needed. In some embodiments, the magnet assembly 1384 comes in contact with one cartridge well 1392 or with more than one cartridge well 1392 as shown in FIG. 13A. In some embodiments, the device may include a heating and/or cooling assembly 1388 in communication with one of the cartridge wells 1392 as shown in FIG. 13B. Any magnetic particles 1386 in the cartridge well 1392 may be attracted to the wall by the magnet assembly 1384.

FIG. 19 shows a more detailed embodiment of a magnetic assembly. The drawing shows how the heating/cooling block 2000 may be attached to slides 2070-2080 and locked into place using notches 2050. The magnetic assembly may consist of a bottom plate 2010 to which is screwed the magnet holders 2020. The magnet holders hold the magnets 2040. The bottom plate has room for at least one magnet holder 2020, at least two magnet holders, at least five magnet holders, at least ten magnet holders, at least twelve magnet holders. The number of magnet holders may equal the number of fluidic cartridge slots in the heating/cooling block. A top block 2040 with as many slots as there are magnet holders is fastened to the bottom plate with movable fastening means 2060. During operation the bottom plate with the attached magnet holders is moved horizontally relative to the top block and in that manner the magnets will be localized close to or away from the wells in the fluidic cartridge By way of example, embodiments of the card and cartridge as disclosed with respect to FIGS. 5-7 and FIGS. 10 &11, respectively, may be used in conjunction with a device described herein to perform any or all of the processing, washing, and antibody binding. Examples of one embodiment of how such a process may be conducted follows. It should be understood that the following procedures are provided by way of example only and that one or more of the steps may be modified and/or deleted and that other types of bioprocessing may be performed using the bioprocessing device, card, and cartridge and other protocols and the same or different bioprocessing cartridge configurations. Each of the steps may be pre-programmed into the automated control system either by a user or as a resident program to run automatically using the automated control system. Each of the fluid mixing or fluid transport steps may involve opening and closing of the relevant valves and pumping using the suitable pump by application of pressure and/or vacuum and/or atmospheric pressure to the relevant valve or pump via the control fluid connectors as well as heating/cooling and application of magnetic fields to one or more wells as necessary:

Immunoprecipitation

Further provided herein are examples of how the device, bioprocessing card, and fluidics cartridge may be used. In some embodiments, the device, card, and cartridge may be used to perform immunoprecipitation. The wells and volumes of the fluidics cartridge may be setup as shown in FIG. 14A as follows:

Processing well, solution, and/or volume:
Waste well;
Antigen-depleted sample (for reuse) 100-1000 µl,
Sample 100-1000 µl,
Ab 1-50 µl in×µl buffer,
PBST 1500 µl (Wash 1),
Elution Buffer 20 µl,
PBS 2000 µl (Wash 2+cleaning),
Magnetic beads in suspension fluid 50 µl, and
Final Antigen eluate 20 µl.

Buffers used may include: Phosphate Buffered Saline (PBS) pH 7.4, PBST—solution of PBS pH 7.4 and 0.02% Tween-20, Elution Buffer pH 2.8—solution including 50 mM glycine, 12.5 mM citric acid, 12.5 mM $NaH_2PO_4$, and 12.5 mM NaCl.

Some of the cartridge wells may remain empty and/or unused.

The processing of the sample may then include the following: Beads are initially suspended with a suspension fluid; a magnetic assembly applied to cartridge well attracts beads to collect them; the supernatant is then removed to the waste well; washing buffer is then transferred from the washing buffer well to the collected beads; beads are resuspended in washing buffer and washed; a magnetic assembly is applied to exterior of the well to attract the beads and to collect them, and the supernatant is then removed from the well to waste; washing buffer is then transferred to the bead well to resuspend and wash the beads again; a magnetic assembly is applied to exterior of the well to attract the beads and to collect them and the supernatant is then removed to waste; antibodies are transferred from the antibody well through the card into the bead well to resuspend the beads; the beads and the antibodies are incubated for 10 minutes with slow pipetting to mix the beads and the antibodies; a magnet is applied to exterior of the well to attract the beads to collect them and the supernatant is then removed to waste; the beads are then washed three times using PBST buffer; between each wash, a magnetic assembly is applied to exterior of the well to attract the beads to collect them and the supernatant is then removed to waste; the sample is then transferred to the bead well to resuspend the beads; the beads and sample are incubated for 10 minutes with slow pipetting the mix the beads and the sample; a magnet is applied to exterior of the well to attract the beads to collect them; the antigen-depleted supernatant is transferred to an empty cartridge well; the beads are then washed three times using PBS; the elution buffer is then transferred to the bead well to resuspend the beads; the beads and resuspension buffer are incubated for 3 minutes with slow pipetting to mix the beads and resuspension buffer; a magnetic assembly is applied to exterior of the well to attract the beads to collect them; the final eluate is removed from the bead well and collected in the eluate well/tube.

Recombinant Protein Isolation

Figure 14B:
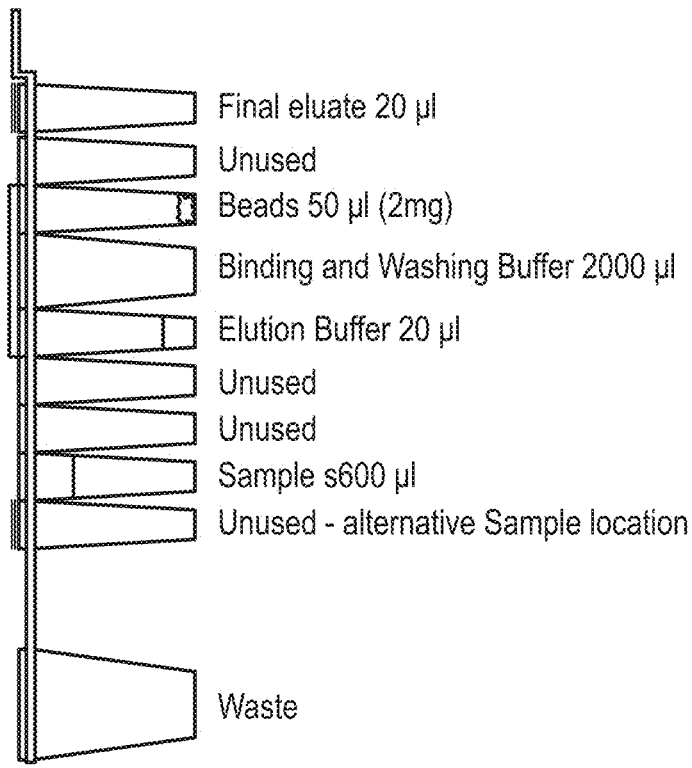
FIGS. 14A-14D show various embodiments of a fluidics cartridge.
Figure 14A:
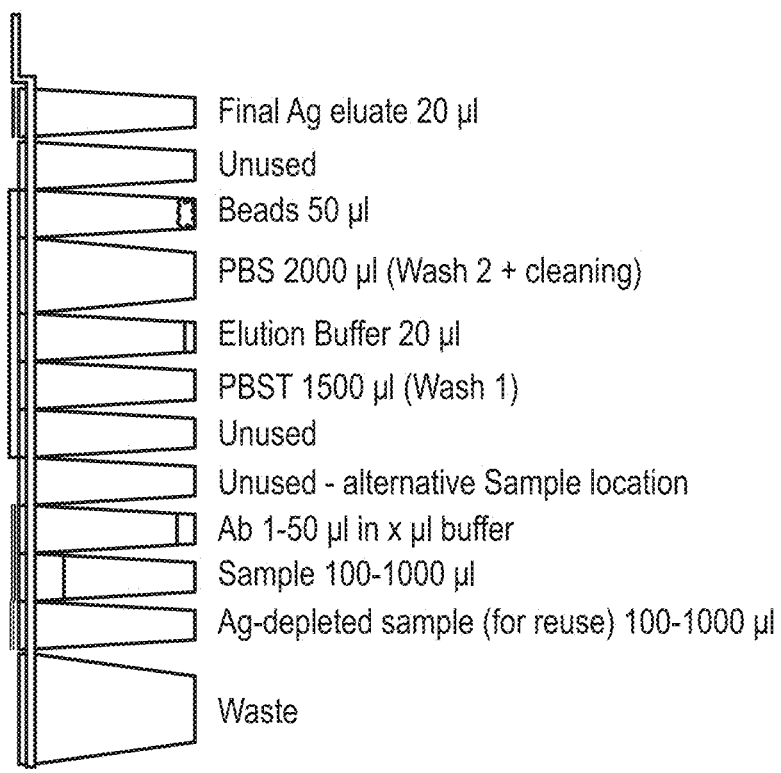

The bioprocessing device, card, and cartridge may also be used for recombinant protein isolation and may be setup as shown in FIG. 14B as follows:

Processing well, solution, and/or volume based on an embodiment:

Waste,
Sample less than or equal to 600 µl,
Elution Buffer 20 µl,
Binding and Washing Buffer 2000 µl,
Magnetic beads in suspension fluid 50 µl,
Final Eluate 20 µl.

Buffers: Binding and Washing Buffer (50 mM Na-phosphate, pH 8.0, 300 mM NaCl, 0.01% Tween-20); Elution Buffer (150 mM Imidazole, 50 mM Na-phosphate, pH 8.0, 300 mM NaCl, 0.01% Tween-20); Low pH Elution Buffer (50 mM Na-acetate, pH 4.5, 300 mM NaCl, 0.01% Tween-20)

Some of the wells may remain empty and/or unused. In some embodiments, some locations on the cartridge may not contain wells.

The processing of the sample may then include the following: The beads are resuspended in the suspension fluid. A magnet is applied to the exterior of the well to attract the beads to collect them and the supernatant is then removed to waste; washing buffer is transferred to the bead well to resuspend the beads and to wash the beads; a magnet is applied to exterior of the well to attract the beads to collect them and the supernatant is then removed to waste; washing buffer is transferred to the bead well to resuspend the beads and to wash the beads; antibody from the antibody well is then transferred to the bead well; the antibodies and the beads are incubated for 2 hours with slow pipetting to mix the beads and the antibodies; a magnet is applied to exterior of the well to attract the beads to collect them and the supernatant is then removed to waste; sample is then transferred to the bead well to resuspend the beads; the beads and the sample are incubated for at least two hours with slow pipetting to mix the beads and the sample; a magnet is applied to exterior of the well to attract the beads to collect them and the supernatant is then removed to waste; the beads are washed three times with washing buffer; after each washing a magnet is applied to exterior of the well to attract the beads to collect them and the supernatant is then removed to waste; after the beads have been washed TE buffer is transferred from the TE buffer well to the bead well to resuspend the beads; the TE buffer and beads are incubated for 4 minutes with slow pipetting to mix the beads and the TE buffer; the beads are then transferred to a the heating well; a magnet is applied to exterior of the well to attract the beads to collect them and the supernatant is then removed to waste; elution buffer is transferred to the beads in the heating well to resuspend the beads; the bead/elution buffer solution is heated at 70 degrees C. for 3 min.; a magnet is applied to exterior of the well to attract the beads to collect them; the final eluate is then transferred to the a collection well for the eluate; elution buffer is transferred to the heating well once more to resuspend the beads a second time; the beads and elution buffer are heated at 70 degrees C. for 3 min.

Protein isolation may also be performed using a modified His-tag purification protocol as follows with following different buffer:

Elution Buffer: 50 mM Na-phosphate, pH 8.0, 300 mM NaCl, 0.01% Tween-20, 300 mM Imidazol.

The processing of the sample may then include the following: The sample is prepared using binding and washing buffer for a total volume up to 700 µl. The magnetic beads (for example purposes only, Dynabeads®, Invitrogen Dynal AS) are resuspended. Approximately 50 µl (2 mg) of the resuspended magnetic particles are then transferred to a microcentrifuge tube or well on the fluidics cartridge. A magnet is applied to the exterior of the well to attract and collect the particles and the supernatant removed and transferred to waste. The particles/beads are resuspended using approximately 300 µl of binding and washing buffer and mixed. A magnetic assembly is applied to the exterior wall of the tube or well to attract and collect the particles and the supernatant is then removed to waste. The sample is then added to the particles and the particles resuspended in the sample. The particles and sample are then incubated on a roller (or other continuous mixing device) for 10 minutes at room temperature (or cold if the protein is unstable at room temperature). A magnetic assembly is applied to the well containing the magnetic particles to attract and collect the particles and the supernatant removed and discarded to waste. The particles are then resuspended and washed 4 times with 300 µl binding and washing buffer. The particles are resuspended between each washing step and a magnetic assembly is applied to the exterior surface to attract and collect the magnetic particles and the supernatant discarded to waste between each wash.

If the protein is to be eluted, 100 µl of elution buffer is added to the particles. The suspension is then mixed for 5 minutes using a roller or other method of mixing (slow pipetting) at room temperature (or cold if the protein is unstable at room temperature). A magnetic assembly is applied to the well containing the magnetic particles to attract and collect the particles and the supernatant containing the eluted protein, such as a histidine-tagged protein, is transferred to a collection tube.

Alternatively, if the protein is to remain bound to the particles, the particles are resuspended in binding and washing buffer or another suitable buffer for the desired application.

Chromatin Immunoprecipitation

In some embodiments, the device, card, and cartridge may be used to perform chromatin immunoprecipitation. In some embodiments, the wells and volumes of the fluidics cartridge may be setup as shown in FIG. 14C as follows:

Processing well, solution, and/or volume:
Waste
Ab 1-50 µl in buffer,
Sample 100 µl
Restriction Enzyme less than 1500 µl
TE Buffer 100 µl
Elution Buffer and Proteinase K 300 µl
Washing Buffer (RIPA) 1600 µl
Magnetic beads 10 µl in suspension fluid,
Heating position 150 µl,
Final Eluate 300 µl.

Buffers: Washing Buffer (RIPA) (TE pH 7.5, 140 mM NaCl, 1 mM EDTA, 0.5 mM EGTA, 0.1% Na-Deoxycholate, 0.1% SDS, 1% Triton x100); Elution Buffer and Proteinase K (20 mM Tris-HCL, pH 7.5, 5 mM EDTA, 20 mM sodium butyrate, 50 mM NaCl, 1% SDS, 50 µg Proteinase K); TE Buffer (10 mM Tris-HCL, pH 7.5, 1 mM EDTA).

Some of the wells may remain empty and/or unused. In some embodiments, some locations on the cartridge may not contain wells.

The processing of the sample may then include the following: The beads in the bead well are suspended in the suspension fluid. The beads in the bead well are collected using a magnet and the supernatant from the bead well removed to waste. The beads are then washed and resuspended using washing buffer transferred from the washing buffer well to the bead well. A magnetic assembly is then applied to the outside of the bead well to collect the beads and the supernatant is removed to waste. The beads are then resuspended and washed a second time. Antibodies are then transferred to the bead well and incubated with the beads for 2 hours with slow pipetting to mix the beads with the antibodies. A magnetic assembly is then applied to the outside of the bead well to collect the beads and the supernatant is removed to waste. The sample is then transferred to the bead well and the beads resuspended in the sample. The sample and beads are incubated for two or more hours with slow pipetting to mix the beads and sample. A magnetic assembly is then applied to the outside of the bead well to collect the beads and the supernatant is removed to waste. The beads are then washed three times with washing buffer, the beads are then collected using a magnetic assembly and the supernatant is removed to waste. TE elution buffer is then transferred to the bead well to resuspend the beads. The beads and TE elution buffer are incubated for four minutes with slow pipetting to mix the beads and the TE buffer. The beads are then transferred to a heating well. A magnetic assembly is then applied to the outside of the bead well to collect the beads and the supernatant is removed to waste. Elution buffer is then added to the beads in the heating well to resuspend the beads. The heating well is then heated at 68 degrees C. for two hours. A magnetic assembly is then applied to the outside of the bead well to collect the beads and the eluate is then transferred to a collection well and/or tube. Elution buffer is added to the bead well one more time to resuspend the beads in the heating well. The heating well is again heated to 68 degrees C. for two hours. A magnetic assembly is then applied to the outside of the bead well to collect the beads and the eluate collected in the collection well and/or tube.

An alternative protocol for a chromatin precipitation using a fluidics cartridge as shown in FIG. 14C may occur as follows:

Processing well, solution, and/or volume:
Waste,
Ab 1-50 µl in buffer,
Sample 10-200 µl,
TE Buffer 100-1500 µl,
TE Buffer high pH 100-1500 ul,
Elution Buffer 100-1500 ul,
Proteinase K 2-20 µl,
Washing Buffer (RIPA) 100-1500 µl,
Washing Buffer other 100-1500 ul,
DNA Purification Buffer 100-1500 ul,
De-Crosslinking buffer 50-1500 ul,
Beads A 10-50 µl in suspension fluid, Beads B 10-50 ul in suspension fluid, Elution position.

Potential Buffers: Washing Buffer (RIPA) (TE pH 7.5, 140 mM NaCl, 1 mM EDTA, 0.5 mM EGTA, 0.1% Na-Deoxycholate, 0.1% SDS, 1% Triton x100); Elution Buffer and Proteinase K (20 mM Tris-HCL, pH 7.5, 5 mM EDTA, 20 mM sodium butyrate, 50 mM NaCl, 1% SDS, 50 µg Proteinase K); TE Buffer (10 mM Tris-HCL, pH 7.5, 1 mM EDTA).

Some of the wells may remain empty and/or unused. In some embodiments, some locations on the cartridge may not contain wells.

The processing of the sample includes the following: The beads in the bead well are collected using a magnet assembly and the supernatant from the bead well removed to waste. The beads may then be washed and resuspended using washing buffer transferred from the washing buffer well to the bead well. A magnetic assembly is then applied to the outside of the bead well to collect the beads and the supernatant is removed to waste. Antibodies are then transferred to the bead well and incubated with the beads for approximately 10 min to 24 approximately hours with slow pipetting to mix the beads with the antibodies. A magnetic assembly is then applied to the outside of the bead well to collect the beads and the supernatant is removed to waste. The sample is then transferred to the bead well and the beads resuspended in the sample. The sample and beads are incubated anywhere from 10 min to two or more hours, with slow pipetting to mix the beads and sample. A magnetic assembly is then applied to the outside of the bead well to collect the beads and the supernatant is removed to waste. The beads are then washed three times with washing buffer, with the bead being collected using a magnetic assembly and the supernatant removed to waste between each wash. The beads are then washed two times with a second washing buffer, with the beads being collected using a magnetic assembly and the supernatant is removed to waste between washes. A de-crosslinking buffer is then transferred to the Proteinase K well and the solution transferred to the bead well to resuspend the beads. The beads and de-crosslinking buffer are incubated for 15 minutes at 55° C. with slow pipetting to mix the beads and the buffer. The supernatant is then transferred to a second heating well and heated at 95° C. for 15 minutes. The supernatant is then cooled to room temperature. Buffer is transferred to the remaining beads and the beads are then transferred to waste. Bead are the transferred to reaction well. A magnetic assembly is then applied to the outside of the bead well to collect the beads and the supernatant is removed to waste. The supernatant above is then transferred to the bead. DNA purification buffer is transferred to the beads and mixed for 5-15 minutes. A magnetic assembly is then applied to the outside of the bead well to collect the beads and the supernatant is removed to waste. Washing buffer is then transferred to the bead and mixed. A magnetic assembly is then applied to the outside of the bead well to collect the beads and the supernatant is removed to waste. The beads are washed one more time and the supernatant removed to waste. Elution buffer is then added to the beads in the heating well to resuspend the beads. The heating well is again heated to 55 degrees C. for 5 minutes. A magnetic assembly is then applied to the outside of the bead well to collect the beads and the eluate collected in the collection well and/or tube.

Nucleic Acid Isolation

Figure 14D:
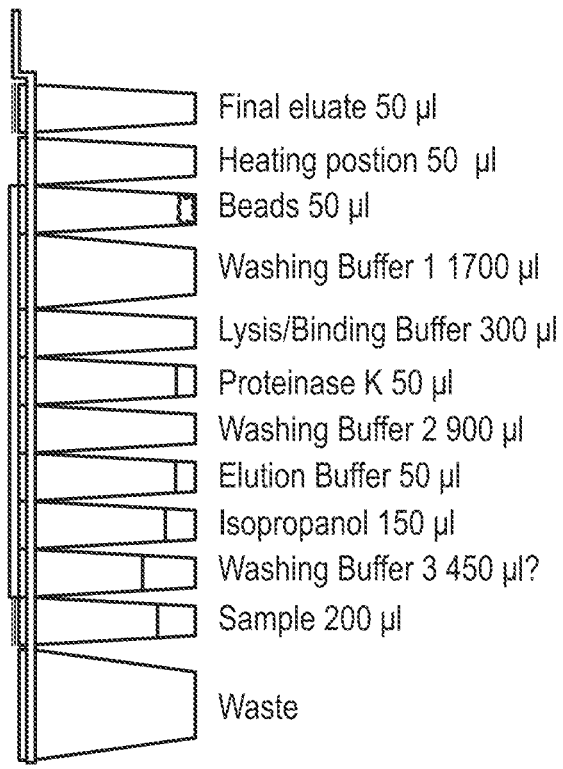
Figure 14C:
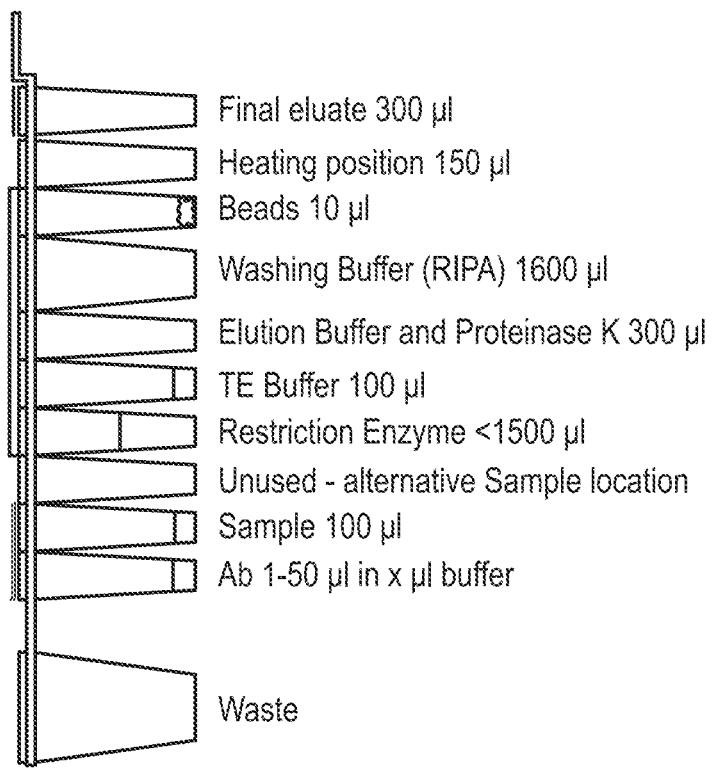

In some embodiments, the device, card, and cartridge may be used to perform nucleic acid isolation, such as SLANE nucleic acid isolation using, for example, a fluidics cartridge set-up as shown in FIG. 14D cartridge as follows:

Processing well, solution, and/or volume: Waste
Sample 200 µl
Washing buffer 3 450 µl
Isopropanol 150 µl
Elution Buffer 50 µl
Washing Buffer 2 900 µl
Proteinase K 50 µl
Lysis/Binding Buffer 300 µl
Washing Buffer 1 1700 µl
Beads 50 µl in suspension fluid
Heating position 50 µl
Final Eluate 50 µl.

Buffers: Lysis/Binding Buffer (5 M guanidine thiocyanate, 50 mM Tris-HCl, pH 6.5, 20% Triton X-100); Washing Buffer 1 (5 M guanidine thiocyanate, 50 mM Tris-HCL, pH 6.5, 1M $MgCl_2$); Washing Buffer 2: 70% Ethanol; Washing Buffer 3: any suitable buffer, same or different from washing buffer 2; Elution Buffer: 10 mM Tris-HCL, pH 8.0

Some of the wells may remain empty and/or unused. In some embodiments, some locations on the cartridge may not contain wells.

The processing of the sample may then include the following: Proteinase K is transferred to the sample in the sample well. Lysis/binding buffer is then transferred to the sample well. The sample/Proteinase K/lysis/buffer solution is then incubated for 10 minutes with slow mixing. The beads in the bead well are resuspended. A magnetic assembly is then applied to the outside of the bead well to collect the beads and the supernatant is removed to waste. The sample solution is then transferred to the bead well. Isopropanol is then transferred to the bead well and the sample solution, isopropanol, and beads are incubated for 10 minutes with slow pipetting to ensure mixing. A magnetic assembly is then applied to the outside of the bead well to collect the beads and the supernatant is removed to waste. Washing buffer 1 is then added to the bead well to resuspend the beads. A magnetic assembly is then applied to the outside of the bead well to collect the beads and the supernatant is removed to waste. Washing buffer 1 is again added to the bead well to resuspend the beads. A magnetic assembly is then applied to the outside of the bead well to collect the beads and the supernatant is removed to waste. The beads are then resuspended/washed two times with washing buffer 2. A magnetic assembly is then applied to the outside of the bead well to collect the beads and the supernatant is removed to waste. Washing buffer 3 is then added to the bead well to resuspend the beads. The beads and buffer are then transferred to a heating well. A magnetic assembly is then applied to the outside of the bead well to collect the beads and the supernatant is removed to waste. Elution buffer is then added to the beads in the heating well to resuspend the beads. The bead solution is heated for 3 minutes at 70 degrees C. A magnetic assembly is then applied to the outside of the bead well to collect the beads and the supernatant is removed to a collection tube/well.

V. Examples

Materials and Methods

Cell Culture: Daudi cells were purchased from American Type Culture Collection (ATCC, Manassas, Va.), cultured on T-150 flasks (BD Biosciences, Bedford, Mass.), and maintained in RPMI-1640 medium (ATCC) supplemented with 2 mM L-glutamine, 10 mM HEPES, 1 mM sodium pyruvate, 4500 mg/L glucose, 1500 mg/L sodium bicarbonate, 1% penicillin/streptomycin, and 10% fetal bovine serum (Invitrogen, Carlsbad, Calif.). All cell cultures were kept in a humidified 5% $CO_2$-95% air incubator at 3° C.

Protein Isolation and Immunoprecipitation:

Prior to cell lysate collection, Daudi cells were spun down and washed with ice-cold PBS three times. The cells were lysed with cell extraction buffer (Invitrogen) containing 1 mM PMSF and a protease inhibitors cocktail [4-(2-aminoethyl) benzenesulfonyl fluoride (AEBSF), E-64, bestatin, leupeptin, aprotinin, and sodium EDTA] from Sigma (St. Louis, Mo.) at a concentration of ~2.5×10^6 cells per mL of extraction buffer. The whole cell lysate was collected from the supernatant after centrifugation at 13,000 rpm for 10 minutes at 4° C.

The following is a protocol for an exogenous protein purification model system for Dynalbeads immunoprecipitation (IP). The protocol utilizes prepared Daudi cell lysate, exogenous human serum albumin (HSA) (Sigma Aldrich), goat-anti-HSA (Bethyl Laboratories (Montgomery, Tex.)), and the Dynalbeads Protein G Immunoprecipitation kit (Invitrogen) to immunoprecipitate and purify the added HSA (target antigen) from the Daudi cell lysate. The amount of exogenous HSA added ranges from 0.25 to 2 μg while the Daudi cell lysate volume is kept at 1-mL. The amount of goat-anti-HSA used was optimized at 5-μg for antibody binding to the beads. The following protocol describes the manual workflow for Dynalbeads Immunoprecipitation Binding of Antibody (Ab)
1. Completely resuspend Dynalbeads by pipetting or rotating on a roller (5 min).
2. Transfer 50 μl Dynabeads to a tube, place on magnet and remove supernatant.
3. Remove tube from magnet and resuspend the Dynabeads in 200 μl Ab Binding & Washing Buffer containing your Ab of choice. (Typically 1-10 μg Ab, the optimal amount needed will depend on the individual Ab used).
4. Incubate 10 minutes with rotation at room temperature.
5. Place tube on magnet and remove supernatant.
6. Remove tube from magnet and wash the Dynabeads-Ab complex by resuspending in 200 μl Ab Binding & Washing Buffer.

Immunoprecipitation of Antigen (Ag)
7. Place tube on magnet and remove supernatant
8. Add your Ag-containing sample (typically 100-1,000 μl) to the Dynabeads-Ab complex and gently resuspend by pipetting.
9. Incubate 10 minutes at room temperature with rotation.
10. Place tube on magnet, transfer supernatant to a clean tube.
11. Wash the Dynabeads-Ab-Ag complex 3 times, using 200 μl Washing Buffer for each wash. Mix gently by pipetting.
12. Resuspend the Dynabeads-Ab-Ag complex in 100 μl Washing Buffer and transfer the suspension to a clean tube. Place tube on magnet and remove supernatant.

Elution of Ab/Aq complex (alternatives A: denaturing or B: non-denaturing)
A. Gently resuspend the Dynabeads-Ab-Ag complex in 20 μl Elution Buffer. Add 10 μl NuPAGE® LDS Sample Buffer/NuPAGE® Reducing Agent mix and incubate 10 minutes at 70° C. Place tube on magnet and load supernatant/sample onto a gel. (Alternatively, the Dynabeads-Ab-Ag complex can be resuspended in the SOS sample buffer of your choice and heated as per your standard protocol prior to gel loading.)
B. Gently resuspend the Dynabeads-Ab-Ag complex in 20 μl Elution Buffer. Incubate 3 minutes at room-temperature. Place tube on magnet and transfer supernatant/sample to a clean tube.

The eluted Ab-Ag complex in elution buffers can be saved at −80° C. for further analysis or used right away to evaluate IP results. The denatured eluted samples (30 μl in volume) or non-denatured eluted samples (20-μl in volume, need to be reduced with NuPAGE® LDS Sample Buffer/NuPAGE® Reducing Agent mix at 70° C. for 10-min) were loaded onto a NuPAGE 4~12% Bis-Tris mini-gel (Invitrogen), run at 200 mV for 1~1.5 hr, and stained with Simply Blue Safestain (Invitrogen). The gel was then read chromogenically.

Figure 15:
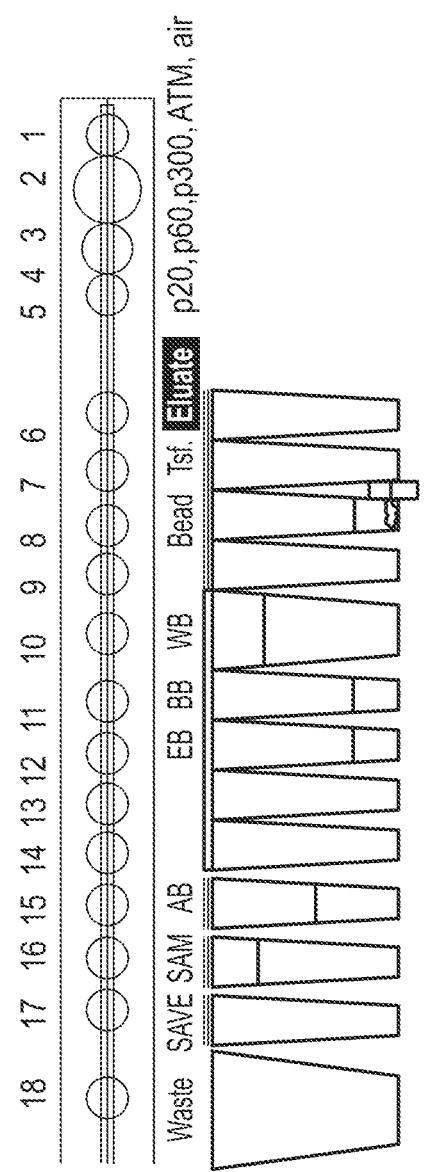
FIG. 15 shows an embodiment of a fluidics cartridge with the fluidics card localized above and the magnetic assembly next to it.

The manifolds, cards, and cartridges were designed to accommodate several applications such as: immunoprecipitation (IP) and chromatin-immunoprecipitation (ChIP) and isolation of histidine tagged proteins or polypeptides. FIG. 15 shows the cartridge layout for the IP application, where #1: vac (atmospheric pressure); pressure (20 PSI pressurized), #2, 3, 4, 5 are atmospheric valve, p300, p60, and p20 pumps, #6 is final eluate, #7 and 8 are the transferred bead well and original bead well, #10 and 11 are washing buffer and Ab binding buffer, #12 is elution buffer, #15, 16, 17 are antibody, sample, and antigen-depleted/saved sample, and #18 is waste. The flow rates for the pumps are as follows: P300: flow rate=0.025 SCFH→each cycle is 15 sec, P60: flow rate=0.35 SCFH→each cycle is 3 sec, P20: flow rate=0.2 SCFH→each cycle is 4 sec.

The IP protocol was written using the PC-software "DYNAL-DESIGNER-V1.1.0.0.exe." The setup of the fluidics cartridge used for each of the examples below is shown in FIG. 15.

Automated Method for Collecting Denatured and Non-Denatured Protein

For the manual IP protocol, there are two possible methods that may be used for elution: denaturing and non-denaturing methods. The denaturing method exposes the beads/antibody/antigen complex to elution buffer at 70° C. for 10-min while the non-denaturing method exposed the beads/antibody/antigen complex to elution buffer at room temperature for 2-min. High heat (70° C.) ensured that all proteins were eluated off the beads and that a majority of the protein structures were denatured. The elution buffer was buffered at pH 2.8 to ensure effective elution of the antigen/antibody off the beads even at room temperature for non-denaturing method.

For the automated platform, ~20-μl of elution buffer (pH 2.8) was transferred from the elution buffer lane into a bead/antibody/antigen complex lane. The protein purified using the manual method and the automated method was compared as shown in FIG. 16A where the numbered lanes correspond to: #1: manual IP: eluted with standard EB (pH 2.8); #2: resuspended beads from #1; #3: automated IP: eluted with standard EB (pH 2.8); #4: resuspended beads from #3; #5: automated IP: eluted with standard EB (pH 2.8); #6: resuspended beads from #5; #7: automated IP: eluted with low-pH EB (pH 2.68); #8: resuspended beads from #8; #9: automated IP: eluted with low-pH EB (pH 2.68); #10: resuspended beads from #9. As seen from lanes #3 and #5, standard pH elution buffer was somewhat diluted using the automated card. There was more protein left on the beads (#4 and #6) compared to all other samples. Lower-pH elution buffer (2.68) elutes protein more efficiently. Lanes #7 and #9 containing purified samples using the device described herein showed amount of purified protein similar to the amount collected using the manual method as seen in lane #1.

The results shown in FIGS. 16B & 16C show the results obtained using the device described herein to run a denaturing method for both the manual and automated protocols. The protein of interest is indicated in the figures by the arrow. Referring to FIG. 16B, the lanes of the gel represent: #1: non-denaturing method (pH 2.8 EB at room temp. for 3-min); #2: resuspended beads from #1; #3: non-denaturing method (pH 2.8 EB at room temp. for 3-min); #4: resuspended beads from #3; #5: denaturing method (pH 2.8 EB at 70° C. for 10-min); #6: denaturing method (pH 2.8 EB at 70° C. for 10-min). As seen in lanes #1 and #3, the amount of protein collected using the non-denaturing elution method was less since the non-denaturing elution method was not able to elute all the proteins off the beads and hence some protein was left on the beads (as shown in lanes #2 and #4). As shown in lanes #5 and #6, the automated denaturing elution method isolated more protein than the and was able to pull down more proteins compared to the amount of protein purified using the manual and automated methods of lanes #1 and #3.

The effect of heating the beads using the device provided herein is shown in FIG. 16C. The lanes of the gel shown are as follows: #1: Manual elution method (heated at 70° C. for 10-min); #2: resuspended beads from #1; #3: Automated elution method (heated at 70° C. for 10-min); #4: resuspended beads from #3; #5: Manual elution method (eluted at room temp for 3-min); #6: resuspended beads from #5; #7: Automated elution method (eluted at room temp for 3-min); #8: resuspended beads from #7. The arrow indicates the protein of interest. With respect to lanes #1, #3, #5, and #7, heating the beads at 70° C. seemed to increase the amount of proteins eluted off the beads. As shown in FIG. 16C, more proteins were left on the beads (as shown in lanes #6 and #8) when no heat was provided. For the automated protocol, denaturing elution method using low-pH elution buffer (2.68) gave very similar protein elution yields as the manual protocol using the same condition.

Automated Small Volume Transfer

The automated platform was able to perform almost all liquid transferring/resuspending processes as efficiently as those in the manual protocol except the final eluate transfer step. During the final eluate transfer step, the ideal was to transfer the 20 μL final eluate from the bead/antibody/antigen tube to a clean tube, without any bead carryover, and without any volume loss.

Figure 18:
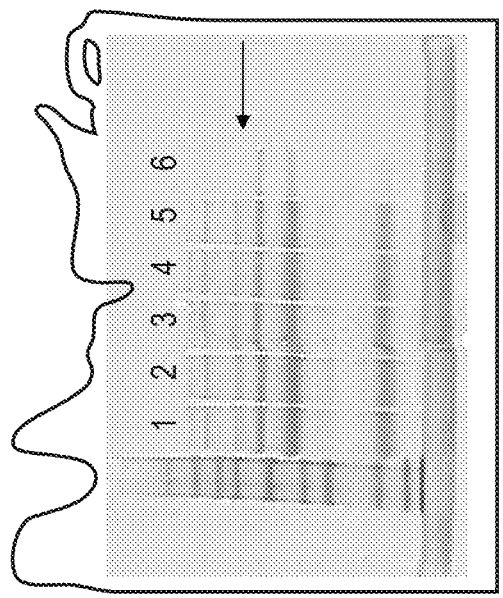
FIG. 18 shows the results generated using the device.
Figure 17:
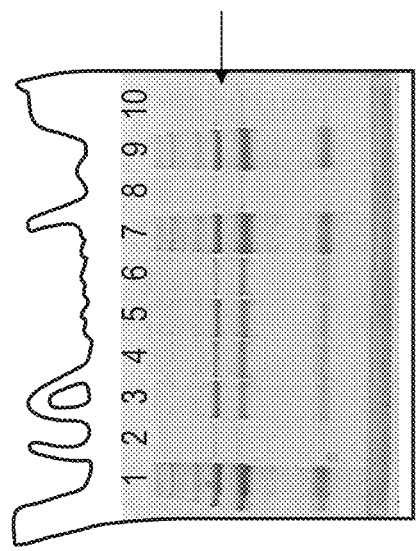
FIG. 17 shows the results generated using the device.

The pump that was used for small-volume transfer has a pump size of 20 μl, with the diaphragm made of silicone membrane. One design was to put an integrated pump between two adjacent pipette tips. However, there was ~5 μl of fluid loss during transfer. A solution to this was to use the a pipette tip to aspirate 20-μl of final eluate from the last processing lane containing the bead/antibody/antigen, removing the pipette tip from the processing lane by either lifting the card and pipette tip out of the lane or by lowering the lane away from the card and pipette tip. The card was then moved horizontally by hand and the pipette tip containing the final sample lowered into the clean tube/lane, and the same pipette tip used to dispense the 20-μl final eluate. This method involves no liquid going into the processing channel or the valves/pumps. Experimental testing, the results of which are shown in FIG. 18, show that this small-volume transfer method reduced the liquid loss to 2~4-μl. The arrow indicates the protein of interest. FIG. 17 shows the amount of protein collected using the small volume transfer method, in which the lanes contain the following: #1: manual IP: eluted with standard EB (pH 2.8); #2: resuspended beads from #1; #3: automated IP: eluted with standard EB (pH 2.8) "Hand-transferred"; #4: resuspended beads from #3; #5: automated IP: eluted with standard EB (pH 2.8) "Transferred automatically with the same tip"; #6: resuspended beads from #5; #7: automated IP: eluted with low-pH EB (pH 2.68). "Hand-transferred"; #8: resuspended beads from #8; #9: automated IP: eluted with low-pH EB (pH 2.68). "Transferred automatically with the same tip"; #10: resuspended beads from #9. As shown previously in FIG. 16A, pH 2.8 elution buffer does not work lane in eluting protein off the beads in the automated platform. Comparing the amount of protein in lanes #3 and #5, hand-transferred and automatic transfer with the same tip gave comparable result. Referring to lanes #7 and #9, respectively, the hand-transferred sample and the automatic transferred sample using the same pipette tip gave comparable results. With automatic transfer, we started with 22.5-μl final eluate and 20.5-μl was collected at the end.

Automated Protein Collection

The instrument allows the card to move vertically, providing two different liquid dispensing positions. It also incorporates a magnet ON/OFF control. However, the instrument could not move the card horizontally so the automatic transfer of the final eluate using the same tip could not be precisely tested.

The testing confirmed that the instrument performed majority of the liquid transferring/resuspending steps compared to the manual protocol (FIG. 18). The arrow indicates the protein of interest collected during the runs. Referring to FIG. 18, the amount of protein collected corresponds to lane: #1: manual IP; #2: manual IP; #3: automated IP on alpha-instrument: hand-collected final eluate; #4: automated IP on alpha-instrument: hand-collected final eluate; #5: automated IP on alpha-instrument: hand-collected final eluate; #6: automated IP on alpha-instrument: automatically-transferred. As shown, lanes #3, #4, #5 show the amount of protein collected using the alpha-instrument with hand-collected final eluate. The yields were slightly lower than the manual results (as shown in lanes #1 and #2).

VI. Systems

Figure 22:
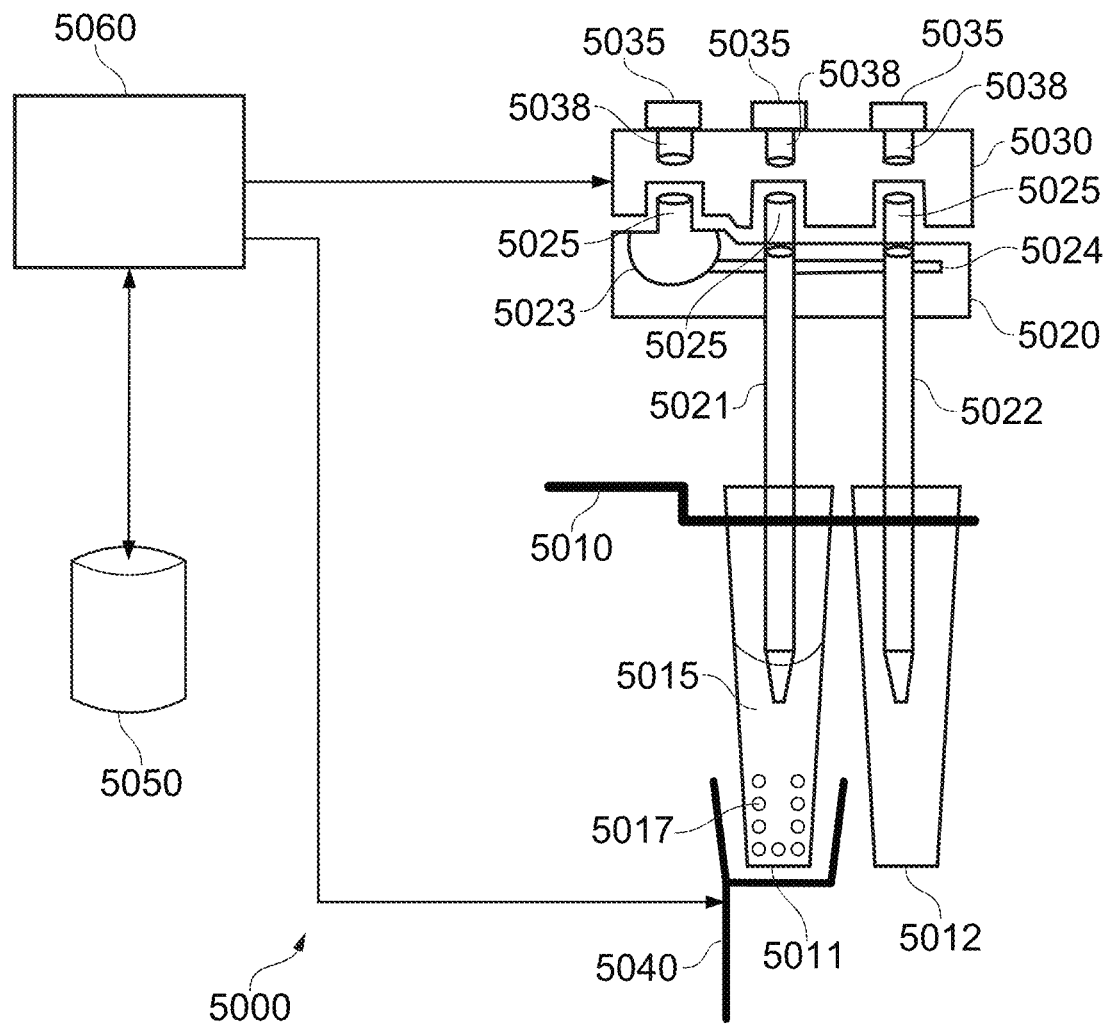
FIG. 22 is a schematic diagram of a system for sample bioprocessing, in accordance with various embodiments.

FIG. 22 is a schematic diagram of a system 5000 for sample bioprocessing, in accordance with various embodiments. System 5000 includes fluidics cartridge 5010, bioprocessing card 5020, manifold 5030, magnetic assembly 5040, memory 5050, and processor 5060.

Fluidics cartridge 5010 includes first well 5011 and second well 5012. First well 5011 holds fluid sample 5015 that includes one or more magnetic particles 5017. Fluid sample 5015 is, for example, a sample that is ready for separation or isolation processing. One or more magnetic particles 5017 can include, but are not limited to including, one or more magnetic beads.

Figure 23:
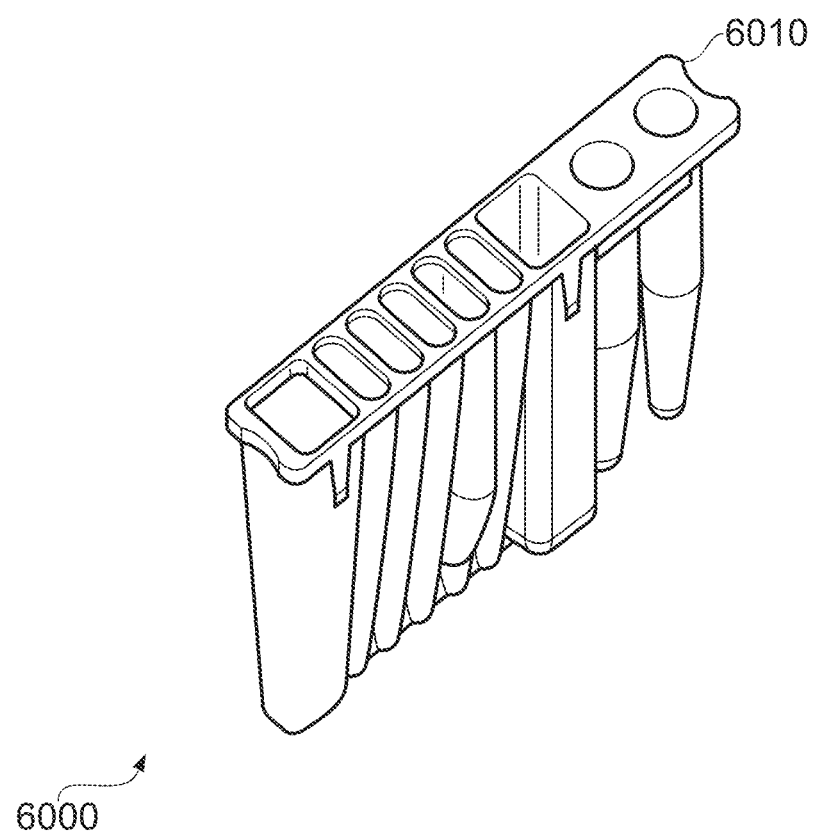
FIG. 23 is a schematic diagram of a perspective view of a fluidics cartridge, in accordance with various embodiments.

In various embodiments, a fluidics cartridge can include three or more wells. FIG. 23 is a schematic diagram of a perspective view 6000 of a fluidics cartridge 6010, in accordance with various embodiments. Fluidics cartridge 6010 includes nine wells.

Returning to FIG. 22, bioprocessing card 5020 includes first pipette tip 5021, second pipette tip 5022, pump 5023, and card valves 5025. First pipette tip 5021, second pipette tip 5022, and pump 5023 are in fluid communication along a processing channel 5024. Card valves 5025 control the access of first pipette tip 5021, second pipette tip 5022, and pump 5023 to processing channel 5024. Bioprocessing card 5020 is placed in proximity to fluidics cartridge 5010 so that first pipette tip 5021 is in fluid communication with first well 5011 and second pipette tip 5022 is in fluid communication with second well 5012. Bioprocessing card 5020 is placed in proximity to fluidics cartridge 5010 using a bioprocessing device housing (not shown), for example.

Figure 24:
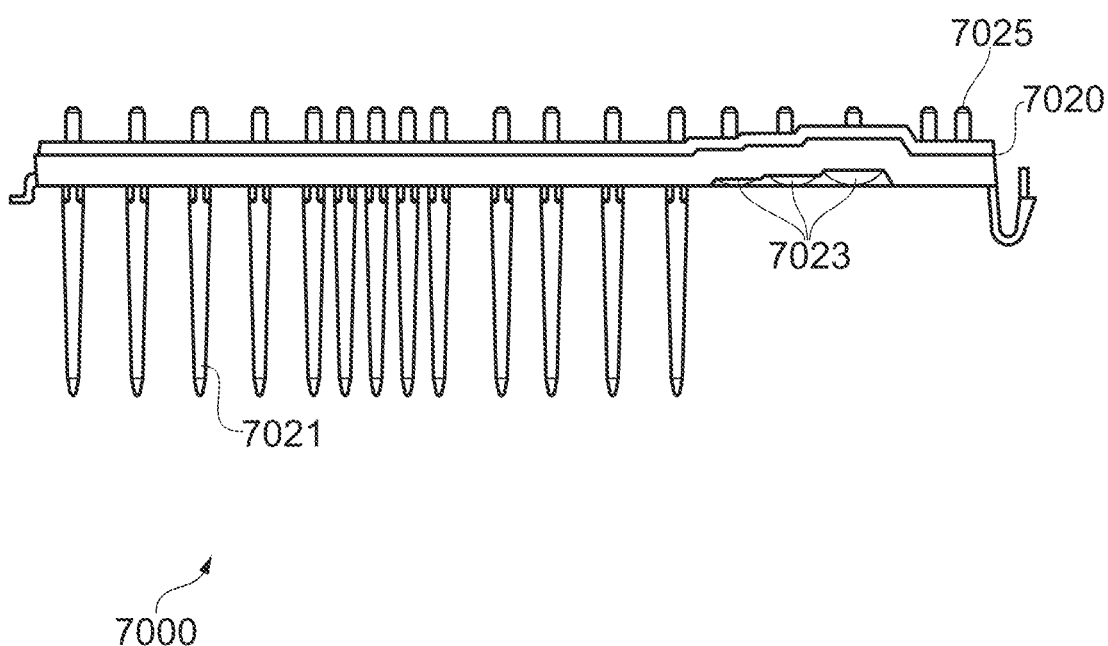
FIG. 24 is a schematic diagram of a side view of a bioprocessing card, in accordance with various embodiments.

In various embodiments a bioprocessing card can include three or more pipette tips and two or more pumps. FIG. 24 is a schematic diagram of a side view 7000 of a bioprocessing card 7020, in accordance with various embodiments. Bioprocessing card 7020 includes 13 pipette tips 7021, three pumps 7023 that have three different volume capacities, and 18 card valves 7025.

Returning again to FIG. 22, manifold 5030 is placed in physical communication with bioprocessing card 5020. Manifold 5030 can also be placed in physical communication with bioprocessing card 5020 using a bioprocessing device housing, for example. Manifold 5030 includes manifold valves 5035 and air channels 5038. Manifold valves 5035 can be, but are not limited to, electronically controlled valves and are located along manifold 5030 and positioned above an area in physical communication with bioprocessing card 5020, for example. Manifold valves 5035 are in further communication with air channels 5038. Air channels 5038 can have valves to supply air, pressure, and/or vacuum to card valves 5025.

Magnetic assembly 5040 is placed in proximity to first well 5011. Magnetic assembly 5040 can also be placed in proximity to first well 5011 using a bioprocessing device housing, for example. In various embodiments, a magnetic assembly can be placed in proximity to two or more wells of a fluidics cartridge. Magnetic assembly 5040 can include, but is not limited to including, a permanent magnet, an electromagnet, or any other suitable mechanism for creating a magnetic field. In various embodiments a magnetic assembly can modulate the magnetic field incident on a fluidics cartridge well by turning on and off an electromagnet or by moving a permanent magnetic with respect to the fluidics cartridge well using a mechanical actuator, for example.

Memory 5050 is any storage device capable of storing instructions, data, or control signals. Memory 5050 can be a standalone storage device or a component of a computer or microcontroller, for example.

Processor 5060 can be, but is not limited to, a computer, computer control system, microcontroller, microprocessor, or any device capable of processing, sending, or, receiving instructions, data, or control signals. Processor 5060 is in electronic communication with manifold 5030, magnetic assembly 5040, and memory 5050. Electronic communication can include, but is not limited to including, a wired connection, a wireless connection, or an optical connection.

Processor 5060 can perform one or more steps of a bioprocessing protocol. For example, Processor 5060 can perform a separation or isolation step. Processor 5060 reads one or more protocol instructions from memory 5050. According to the one or more protocol instructions, processor 5060 activates magnetic assembly 5040 to apply a magnetic field to first well 5011 so that at least one magnetic particle of one or more magnetic particles 5017 of fluid sample 5015 is attracted. Processor 5060 then signals manifold 5030 to apply pressure and/or vacuum to bioprocessing card 5020 activating card valves 5025 of first pipette tip 5021, second pipette tip 5022, and pump 5023 to move a portion of fluid sample 5015 from first well 5011 through processing channel 5024, to second well 5012 producing a bioprocessed, separated, or isolated sample in first well 5011.

VII. Other Processing Devices

In various embodiments, system 5000 can include one or more heating/cooling blocks (not shown) for heating and/or cooling a fluid contained fluidics cartridge 5010. The one or more heating/cooling blocks are placed in proximity to fluidics cartridge 5010. The one or more heating/cooling blocks can also be placed in proximity to fluidics cartridge 5010 using a bioprocessing device housing, for example. The one or more heating/cooling blocks are in electronic communication with processor 5060. The one or more heating/cooling blocks receive a signal from processor 5060 to heat or cool one or more wells of fluidics cartridge 5010, according to instructions read by processor 5060 from memory 5050. The one or more heating/cooling blocks can include one or more Peltier elements, for example.

In various embodiments, system 5000 can include a card actuator (not shown) to move bioprocessing card 5020 with respect to fluidics cartridge 5010 so that first pipette tip 5021 and second pipette tip 5022 of bioprocessing card 5020 can be moved to different depths in first well 5011 and second well 5012 of fluidics cartridge 5010, respectively. The card actuator is in electronic communication with processor 5060. The card actuator receives a signal from processor 5060 to move bioprocessing card 5020 according to instructions read by processor 5060 from memory 5050. In various embodiments, the card actuator can completely remove a pipette tip of a bioprocessing card from a well of a fluidics cartridge. In various embodiments, the card actuator can move manifold 5030 in conjunction with bioprocessing card 5020.

In various embodiments, system 5000 can include a cartridge actuator (not shown) to move fluidics cartridge 5010 with respect to bioprocessing card 5020 so that first pipette tip 5021 of bioprocessing card 5020 can be moved from first well 5011 to second well 5012 of fluidics cartridge 5010. The cartridge actuator is in electronic communication with processor 5060. The cartridge actuator receives a signal from processor 5060 to move fluidics cartridge 5010 according to instructions read by processor 5060 from memory 5050.

In various embodiments, processor 5060 uses the cartridge actuator in concert with card actuator to move fluid from first well 5011 to second well 5012 within a pipette tip. For example, processor 5060 can signal manifold 5030 to apply pressure and/or vacuum to bioprocessing card 5020 so that fluid is drawn into first pipette tip 5021 but not processing channel 5024. Processor 5060 can signal the card actuator to move bioprocessing card 5020 with respect to fluidics cartridge 5010 so that first pipette tip 5021 is lifted out of first well 5011. Processor 5060 can signal the cartridge actuator to move fluidics cartridge 5010 with respect to bioprocessing card 5020 so that second well 5012 is move to a location under first pipette tip 5021. Processor 5060 can then again signal the card actuator to move bioprocessing card 5020 with respect to fluidics cartridge 5010, but this time so that first pipette tip 5021 is lowered into second well 5012. Finally, processor 5060 completes the fluid transfer by signalling manifold 5030 to apply pressure and/or vacuum to bioprocessing card 5020 so that fluid is expelled from first pipette tip 5021 but not processing channel 5024.

VIII. Input/Output Device

In various embodiments, system 5000 can include an input/output (I/O) device (not shown) that is in electronic communication with processor 5060. The I/O device can be, but is not limited to, a universal serial bus (USB) port. A memory device or memory stick can be connected to the I/O device. In various embodiments, processor 5060 reads directly from the memory device or transfers instructions, data, or control signals from the memory device to memory 5050. The instructions, data, or control signals can include bioprocessing protocol instructions, operating system updates, or diagnostics. In various embodiments, processor 5060 can determine from the memory device if the memory device includes maintenance code or run-time instructions.

IX. Card Check

In various embodiments, system 5000 can include more than one bioprocessing card. To accommodate more than one bioprocessing card, manifold 5030 can include a slot for each bioprocessing card.

In various embodiments, processor 5060 can determine if a bioprocessing card is missing from a slot of manifold 5030. Each bioprocessing card includes a check valve (not shown) and manifold 5030 can detect a pressure at the check value valve. Processor 5060 can signal manifold 5030 to apply pressure and/or vacuum to a bioprocessing card to close the check valve and open all other card valves of the bioprocessing card. Processor 5060 signals manifold 5030 to increase the pressure of the bioprocessing card to a system pressure. Processor 5060 then signals manifold 5030 to open the check valve. Finally, if processor 5060 receives a system pressure from manifold 5030 at the check valve, then processor 5060 determines that the bioprocessing card is present. If processor 5060 does not receive a system pressure from manifold 5030 within a certain period of time, then processor 5060 determines that the bioprocessing card is not present.

X. User Interface

In various embodiments, system 5000 can include a user interface (UI) device (not shown) that is in electronic communication with processor 5060. The UI device can include a graphical interface. Processor 5060 displays one or more bioprocessing protocols on the UI device. Processor 5060 receives a protocol selection from the UI device that indicates a selection by a user. Processor 5060 can also display on the UI device one or more protocol parameters for the protocol selection and receive from the UI device one or more protocol parameters that indicate parameters selected by a user for a selected protocol. A protocol parameter can include, but is not limited to including, a time or a temperature value. Processor 5060 can also display an indication of a current processing step in the UI device, including an indication of the completion of processing. In various embodiments, processor 5060 can begin a bioprocessing protocol after receiving a single protocol selection from the UI device. The single protocol selection can be a single touch from a user, for example.

XI. Scripting Language

As described above, processor 5060 reads one, or more protocol instructions from memory 5050. In various embodiments, the one or more protocol instructions stored in memory 5050 are provided in a scripting language format. This scripting language format allows scientists to develop protocols without needing to understand the underlying details of the system's devices.

In various embodiments, the scripting language format includes a list of bioprocessing sequences. For example, a sequence can be a transfer of a volume of liquid from one well to another well. Each sequence can also include one or more steps. A transfer sequence can have, for example, separate steps to control two pipette tips and a pump. Processor 5060 reads a script for a bioprocessing protocol from memory 5050, parses the script, and translates the sequences and steps into lower level commands for manifold 5030, and magnetic assembly 5040, or other processing devices, for example. The lower level commands for a step can include processing device control signals, for example.

XII. Smart Manifold

Manifold 5030 applies pressure and/or vacuum to bioprocessing card 5020 by activating one or more manifold valves 5035. In various embodiments, manifold 5030 can include a matrix of address lines connected to manifold valves 5035 so that processor 5060 can control manifold valves 5035 individually and in parallel. As described above, system 5000 can include more than one bioprocessing card and fluidics cartridge combination. As a result, processor 5060 can execute the same protocol on multiple samples at substantially the same time. A matrix of address lines allows processor 5060 to execute the same control function across multiple bioprocessing cards using a single signal sent to manifold 5030.

Figure 25:
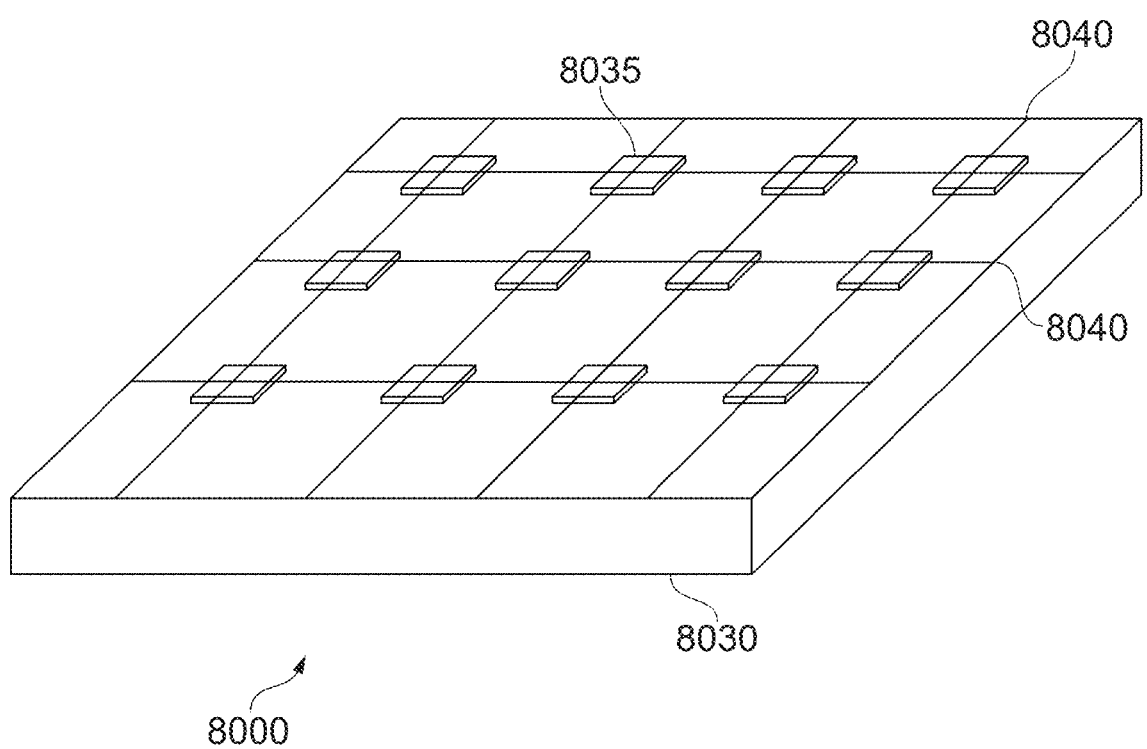
FIG. 25 is a schematic diagram of a perspective view of a manifold that includes a matrix of address lines, in accordance with various embodiments.

FIG. 25 is a schematic diagram of a perspective view 8000 of a manifold 8030 that includes a matrix of address lines 8040, in accordance with various embodiments. Manifold 8030 includes 12 manifold valves 8035 and 7 address lines 8040. Manifold 8030, therefore, includes a 4×3 matrix of address lines. Manifold 8030 can, for example, apply pressure and/or vacuum to four bioprocessing cards that each have three card valves. A processor can control any one of the 12 manifold valves by using two of the seven address lines 8040. A processor can also perform parallel commands on two or more bioprocessing cards by selecting the address lines of the two or more cards and then selecting an address line of a particular card valve.

XIII. Methods

Figure 26:
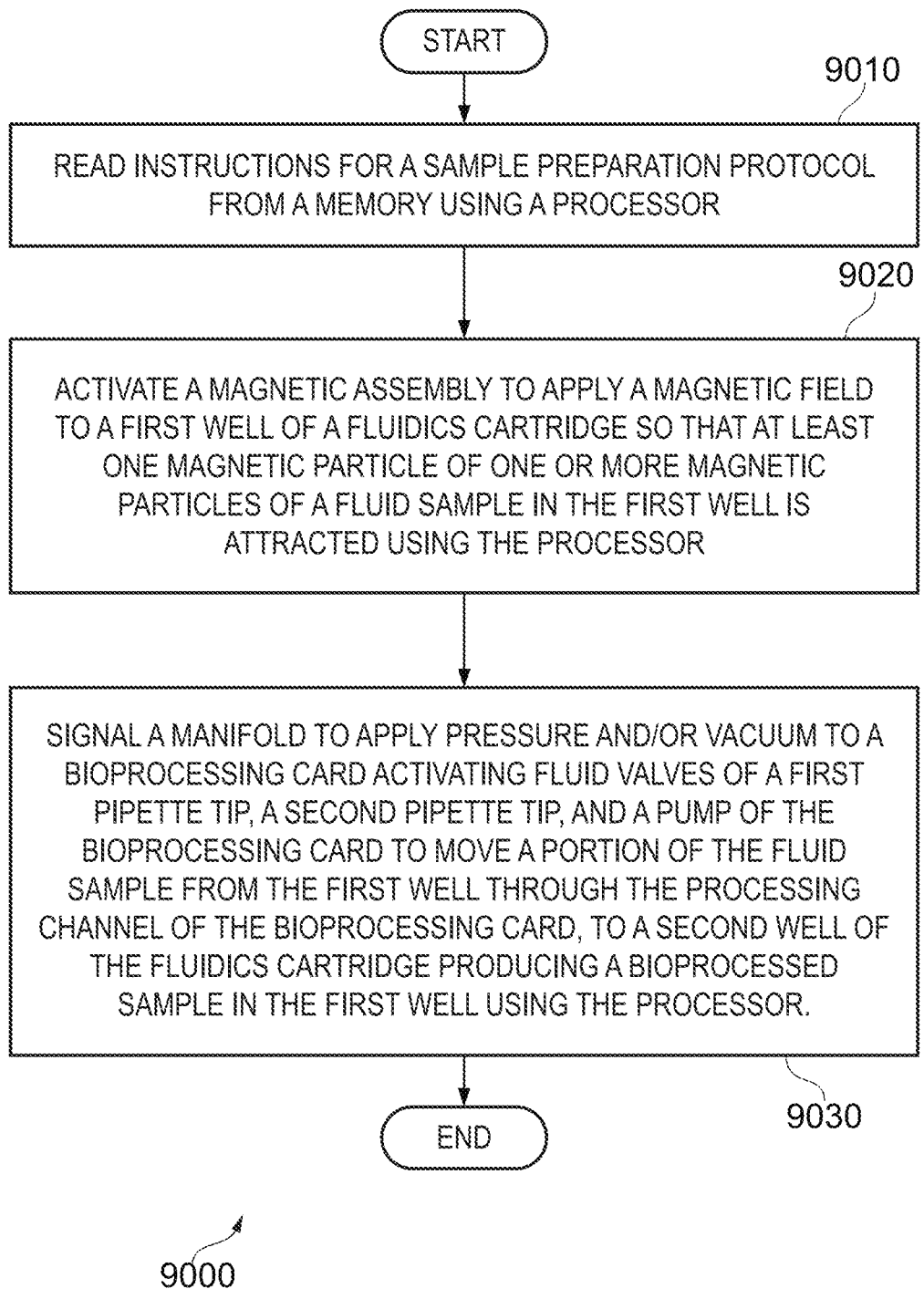
FIG. 26 is a flowchart showing a method for sample bioprocessing, in accordance with various embodiments.

FIG. 26 is a flowchart showing a method 9000 for sample bioprocessing, in accordance with various embodiments.

In step 9010 of method 9000, instructions are read for a sample preparation protocol from a memory using a processor.

In step 9020, a magnetic assembly is activated to apply a magnetic field to a first well of a fluidics cartridge so that at least one magnetic particle of one or more magnetic particles of a fluid sample is attracted using a processor. The fluidics cartridge includes the first well and a second well. The first well holds the fluid sample that includes the one or more magnetic particles. The magnetic assembly is in proximity to the fluidics cartridge.

In step 9030, a manifold is signaled to apply pressure and/or vacuum to a bioprocessing card activating fluid valves of a first pipette tip, a second pipette tip, and a pump to move a portion of the fluid sample from the first well through the processing channel, to the second well producing a bioprocessed sample in the first well using the processor. The bioprocessing card includes the first pipette tip, the second pipette tip, and the pump that are in fluid communication along a processing channel of the bioprocessing card. The bioprocessing card is in proximity to the fluidics cartridge so that the first pipette tip is in fluid communication with the first well and the second pipette tip is in fluid communication with the second well. The manifold is in physical communication with the bioprocessing card.

XIV. Computer Program Product

In certain embodiments, a computer program product includes a tangible computer-readable storage medium whose contents include a program with instructions being executed on a processor so as to perform a method for sample bioprocessing. This method is performed by a system of distinct software modules.

Figure 27:
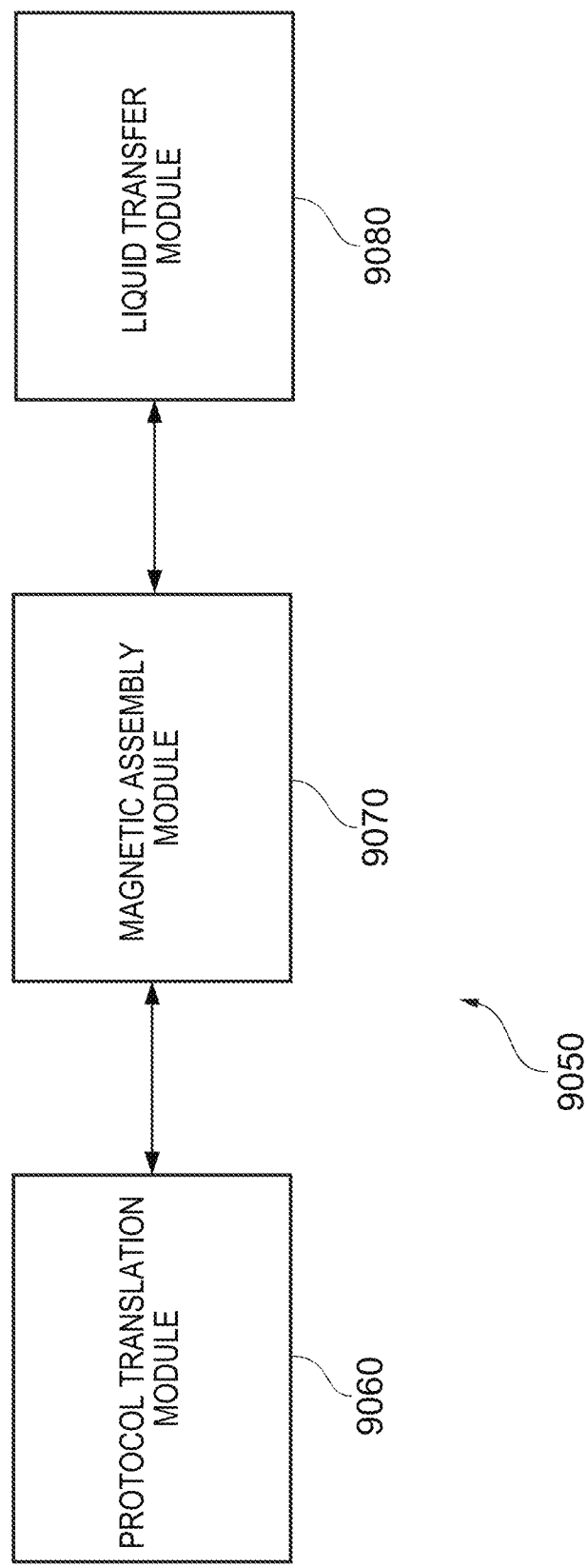
FIG. 27 is a schematic diagram of a system of distinct software modules that perform a method for sample bioprocessing, in accordance with certain embodiments.

FIG. 27 is a schematic diagram of a system 9050 of distinct software modules that perform a method for sample bioprocessing, in accordance with certain embodiments. System 9050 includes protocol translation module 9060, magnetic assembly module 9070, and liquid transfer module 9080.

Protocol translation module 9060 reads instructions for a sample preparation protocol. Magnetic assembly module 9070 activates a magnetic assembly to apply a magnetic field to a first well of a fluidics cartridge so that at least one magnetic particle of one or more magnetic particles of a fluid sample is attracted. The fluidics cartridge includes the first well and a second well. The first well holds the fluid sample that includes the one or more magnetic particles. The magnetic assembly is in proximity to the fluidics cartridge.

Liquid transfer module 9080 signals a manifold to apply pressure and/or vacuum to a bioprocessing card activating fluid valves of a first pipette tip, a second pipette tip, and a pump to move a portion of the fluid sample from the first well through the processing channel, to the second well producing a bioprocessed sample in the first well. The bioprocessing card includes the first pipette tip, the second pipette tip, and the pump that are in fluid communication along a processing channel of the bioprocessing card. The bioprocessing card is in proximity to the fluidics cartridge so that the first pipette tip is in fluid communication with the first well and the second pipette tip is in fluid communication with the second well. The manifold is in physical communication with the bioprocessing card.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A system for sample bioprocessing, comprising:
   a. a fluidics cartridge that includes a first well and a second well, wherein the first well holds a fluid sample that includes one or more magnetic particles;
   b. a bioprocessing card that includes a first pipette tip, a second pipette tip, and a pump that are in fluid communication along a processing channel and that is placed in proximity to the fluidics cartridge so that the first pipette tip is in fluid communication with the first well and the second pipette tip is in fluid communication with the second well wherein the processing channel is a mesoscale channel or a microscale channel, the first pipette tip and second pipette tip include individual valves;
   c. a manifold that is in physical communication with the bioprocessing card;
   d. a magnetic assembly including at least one electromagnet or permanent magnet that is placed in proximity to the fluidics cartridge;
   e. a memory that includes instructions for a sample preparation protocol; and
   f. a processor that is in electronic communication with the manifold, the magnetic assembly, and the memory, that reads the instructions from the memory, and that according to the instructions
      i. activates the magnetic assembly to apply a magnetic field to the first well so that at least one magnetic particle of the one or more magnetic particles of the fluid sample is attracted and
      ii. signals the manifold to apply pressure and/or vacuum to the bioprocessing card activating the fluid valves of the first pipette tip, the second pipette tip, and the pump to move a portion of the fluid sample from the first well though the processing channel, to the second well producing a bioprocessed sample in the first well;
   g. a housing containing the fluidics cartridge, the bioprocessing card, the manifold, the magnetic assembly, the memory and the processor, wherein at least one vent is located on a portion of the housing configured to provide heat dispersion.

2. The system of claim 1, further comprising a heat/cooling block that is placed in proximity to the fluidics cartridge, that is in electronic communication with the processor, and that receives a signal from the processor to heat or cool of the fluidics cartridge according to the instructions.

3. The system of claim 1, further comprising an input/output device from which the processor can also read the instructions, wherein the input/output device is in electronic communication with the processor.

4. The system of claim 3, further comprising a user interface device from which the processor receives a protocol selection from a user, wherein the input/output device is in electronic communication with the processor.

5. The system of claim 4, wherein the processor receives a protocol parameter from the user interface device that indicates a parameter selected by the user.

6. The system of claim 4 or 5, wherein the processor sends a system status to the user interface device.

7. The system of claim 1, wherein the instructions comprise a scripting language format.

8. The system of claim 7, wherein the scripting language format comprises a bioprocessing sequence.

9. The system of claim 8, wherein the bioprocessing sequence comprises a step.

10. The system of claim 9, wherein the processor translates the step into a processing device signal.

11. The system of claim 1, wherein the manifold applies pressure and/or vacuum to the bioprocessing card by activating one or more manifold valves of a plurality of manifold valves on the manifold.

12. The system of claim 11, wherein the manifold activates the one or more manifold valves using a matrix of address lines to allow more than one bioprocessing card to perform the sample preparation protocol at substantially the same time.

13. The system of claim 12, wherein each manifold valve of the plurality of manifold valves can be addressed using two address lines of the matrix of address lines.

14. The system of claim 1, wherein the bioprocess card comprises:
   a plurality of pipette tips in addition to the first and second pipette tip;
   at least one pump in fluid communication with the plurality of pipette tips; and
   a plurality of valves, wherein the plurality of pipette tips and the at least one pump are in fluid communication through the processing channel.

15. The system of claim 14, wherein the bioprocess card further comprises a plurality of control fluid connectors, wherein the control fluid connector is configured to be in communication with the pipette tips and wherein a control fluid connector is configured to be in communication with the at least one pump.

16. The system of claim 15, wherein the bioprocessing card further comprising a membrane.

17. The system of claim 16, wherein the bioprocessing card further comprises a sealing foil.

18. The system of claim 1, wherein the fluidics cartridge includes an opening configured to receive a container configured to contain and confine a liquid.

19. A method for sample bioprocessing, comprising:
   a. reading instructions for a sample preparation protocol from a memory using a processor;
   b. activating a magnetic assembly to apply a magnetic field to a first well of a fluidics cartridge so that at least one magnetic particle of one or more magnetic particles of a fluid sample is attracted using the processor, wherein the fluidics cartridge includes the first well and a second well, wherein the first well holds the fluid sample that includes the one or more magnetic particles, and wherein the magnetic assembly includes at least one electromagnet or permanent magnet that is placed in proximity to the fluidics cartridge; and
   c. signaling a manifold to apply pressure and/or vacuum to a bioprocessing card activating fluid valves of a first pipette tip, a second pipette tip, and a pump to move a portion of the fluid sample from the first well through a processing channel wherein the processing channel is a mesoscale channel or a microscale channel, to the second well producing a bioprocessed sample in the first well using the processor, wherein the bioprocessing card includes the first pipette tip, the second pipette tip, and the pump that are in fluid communication along the processing channel, wherein the bioprocessing card is in proximity to the fluidics cartridge so that the first pipette tip is in fluid communication with the first well and the second pipette tip is in fluid communication with the second well, and wherein the manifold is in physical communication with the bioprocessing card
   d. dispersing heat generated from executing the sample preparation protocol through at least one vent is in a housing, the housing containing the fluidics cartridge, the bioprocessing card, the manifold, the magnetic assembly, the memory and the processor.

* * * * *